US010792287B2

(12) United States Patent
Cortopassi et al.

(10) Patent No.: US 10,792,287 B2
(45) Date of Patent: Oct. 6, 2020

(54) METHODS FOR TREATING MITOCHONDRIAL DISEASES

(71) Applicant: The Regents of the University of California, Oakland, CA (US)

(72) Inventors: Gino Cortopassi, Davis, CA (US); Sandipan Datta, Davis, CA (US); Alfred Yu, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/993,237

(22) Filed: May 30, 2018

(65) Prior Publication Data

US 2018/0369246 A1    Dec. 27, 2018

Related U.S. Application Data

(63) Continuation of application No. PCT/US2016/064779, filed on Dec. 2, 2016.

(60) Provisional application No. 62/262,792, filed on Dec. 3, 2015.

(51) Int. Cl.

| *A61K 31/52* | (2006.01) |
| *A61K 31/122* | (2006.01) |
| *A61K 31/155* | (2006.01) |
| *A61P 27/02* | (2006.01) |
| *A61K 31/53* | (2006.01) |
| *A61K 31/437* | (2006.01) |
| *A61K 31/472* | (2006.01) |
| *A61K 31/137* | (2006.01) |
| *A61K 31/436* | (2006.01) |
| *A61K 47/10* | (2017.01) |

(52) U.S. Cl.
CPC ............ *A61K 31/52* (2013.01); *A61K 31/122* (2013.01); *A61K 31/137* (2013.01); *A61K 31/155* (2013.01); *A61K 31/436* (2013.01); *A61K 31/437* (2013.01); *A61K 31/472* (2013.01); *A61K 31/53* (2013.01); *A61P 27/02* (2018.01); *A61K 47/10* (2013.01)

(58) Field of Classification Search
CPC .... A61K 31/52; A61K 31/155; A61K 31/436; A61K 31/122; A61K 47/10; A61P 27/02
USPC ......................................................... 514/49
See application file for complete search history.

(56) References Cited

U.S. PATENT DOCUMENTS

| 2014/0031432 A1 | 1/2014 | Jankowski et al. |
| 2014/0256786 A1 | 9/2014 | Liu et al. |

FOREIGN PATENT DOCUMENTS

| WO | 2007/019345 | 2/2007 |
| WO | 2015/155231 | 10/2015 |
| WO | 2017/096270 | 1/2017 |

OTHER PUBLICATIONS

Glossary of medical education terms, Institute of International Medical Education. http://www.iime.org/glossary.htm Accessed in Mar. 2013. (Year: 2013).*
Daniele et al. Zolpidem in Progressive Supranuclear Palsy. The New England Journal of Medicine 341(7):543-544, Aug. 12, 1999. (Year: 1999).*
Scarpelli et al. Current Options in the Treatment of Mitochondrial Diseases. Recent Patents on CNS Drug Discovery 5:203-209, 2010. (Year: 2010).*
Golbe Li. Progressive Supranuclear Palsy. Sennin Neurol 34:151-159, 2014. (Year: 2014).*
Clauss et al., "Transient Improvement of Spinocerebellar Ataxia with Zolpidem," The New England Journal of Medicine, vol. 351, Jul. 29, 2004, pp. 511-512.
Cornelius et al., "Oxidative stress and mitochondrial dysfunction in spinocerebellar ataxia type 2 (SCA2)," CAG Triplet Repeat Disorders, Gordon Research Conference, May 2015, 3 pages.
Heitz et al., "Idebenone Protects Against Retinal Damage and Loss of Vision in a Mouse Model of Leber's Hereditary Optic Neuropathy," PLoS One, vol. 7, No. 9, Sep. 2012, pp. 1-11.
Iyer , "Novel Therapeutic Approaches for Leber's Hereditary Optic Neuropathy," Discover Medicine, vol. 15, No. 82, Mar. 2013, pp. 1-8.
Maust et al., "Use of Methotrexate in Sarcoid-associated Optic Neuropathy," Ophthalmology, vol. 110, No. 3, Mar. 2003, pp. 559-563.
Simon et al., "Mitochondrial Complex I Gene Variant Associated with Early Age at Onset in Spinocerebellar Ataxia Type 2,", Arch Neurol., vol. 64, No. 7, Jul. 2007, pp. 1042-1044.
Yu et al., "Mitochondrial complex deficiency leads to inflammation and retinal ganglion cell death in the Ndufs4 mouse," Human Molecular Genetics, vol. 24, No. 10, May 15, 2015, pp. 2848-2860.

* cited by examiner

*Primary Examiner* — Yih-Horng Shiao
(74) *Attorney, Agent, or Firm* — Kilpatrick Townsend & Stockton LLP

(57) ABSTRACT

The present invention provides pharmaceutical compounds and methods for preventing, ameliorating, or treating a mitochondrial disease by administering such compounds to a subject in need thereof. In some cases, the subject suffers from a mitochondrial disease or is predisposed to having a mitochondrial disease. The mitochondrial disease includes those associated with impairments to mitochondrial oxidative phosphorylation that can lead to vision loss or blindness.

15 Claims, 24 Drawing Sheets

Specification includes a Sequence Listing.

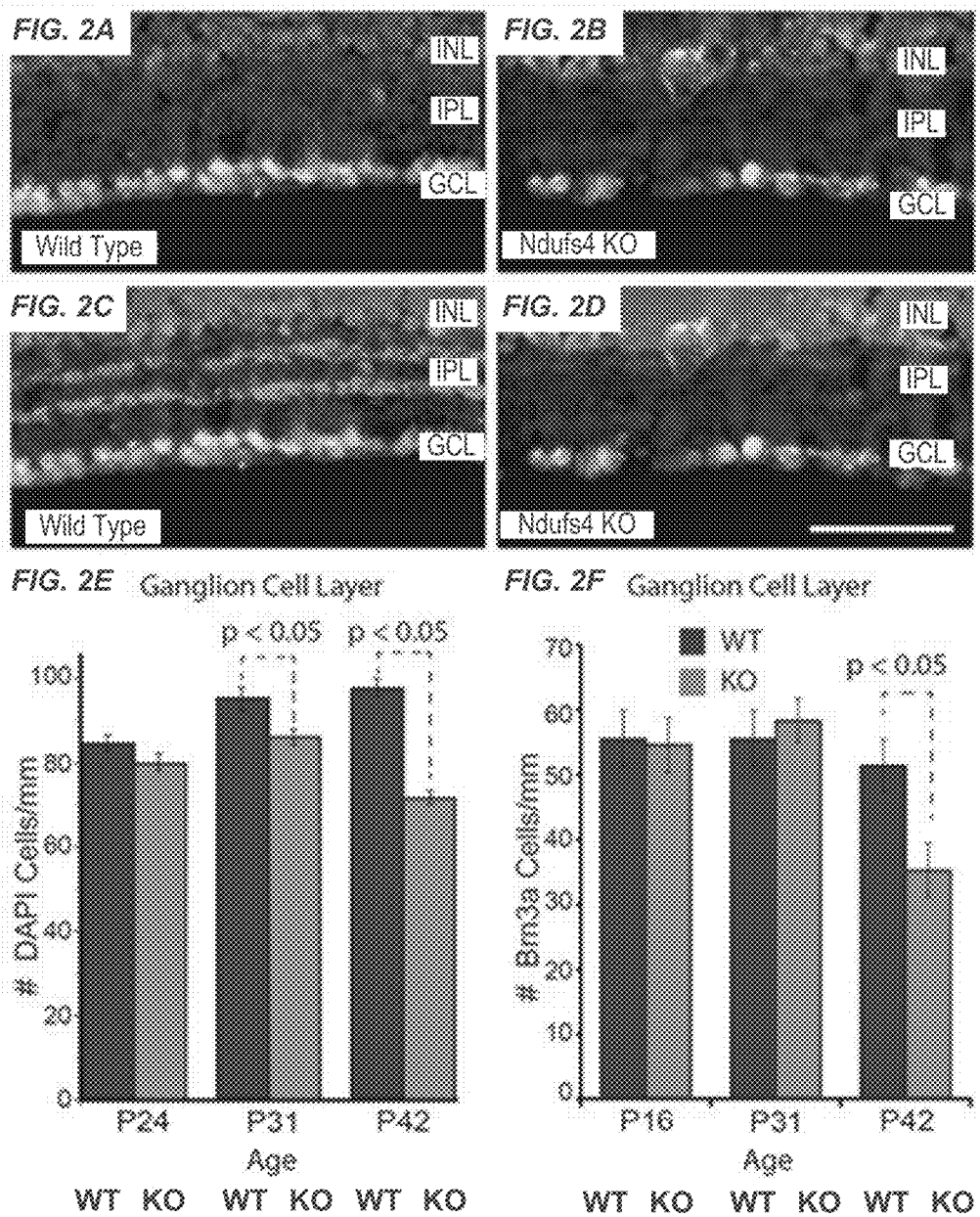

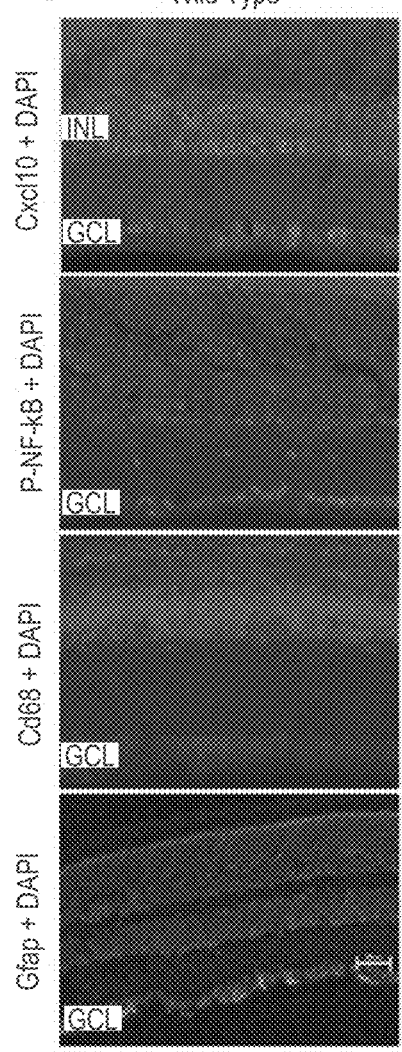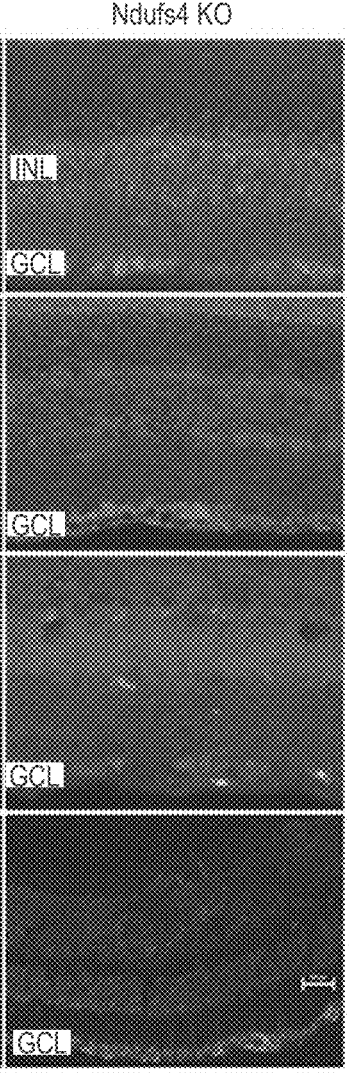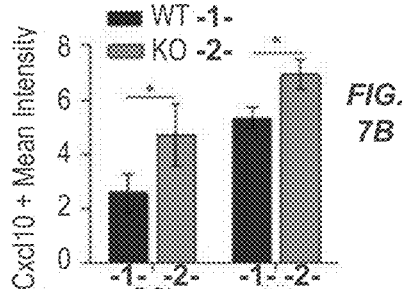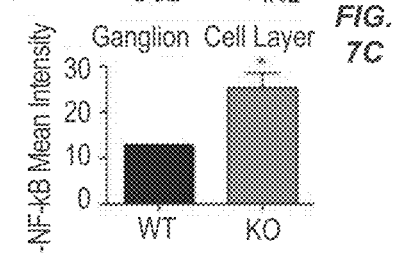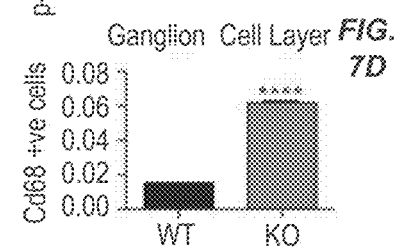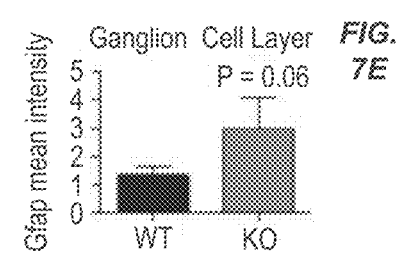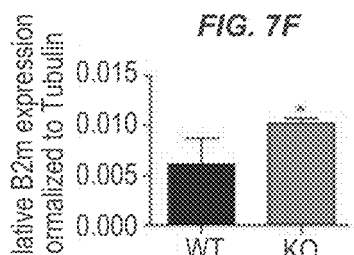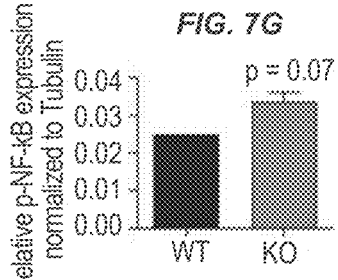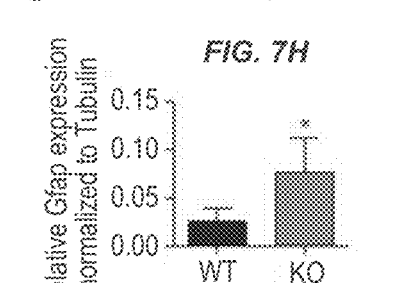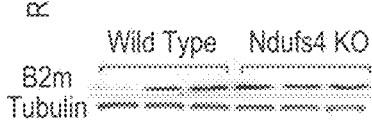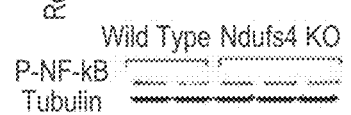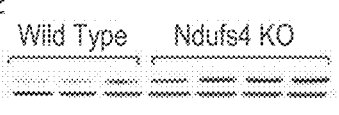

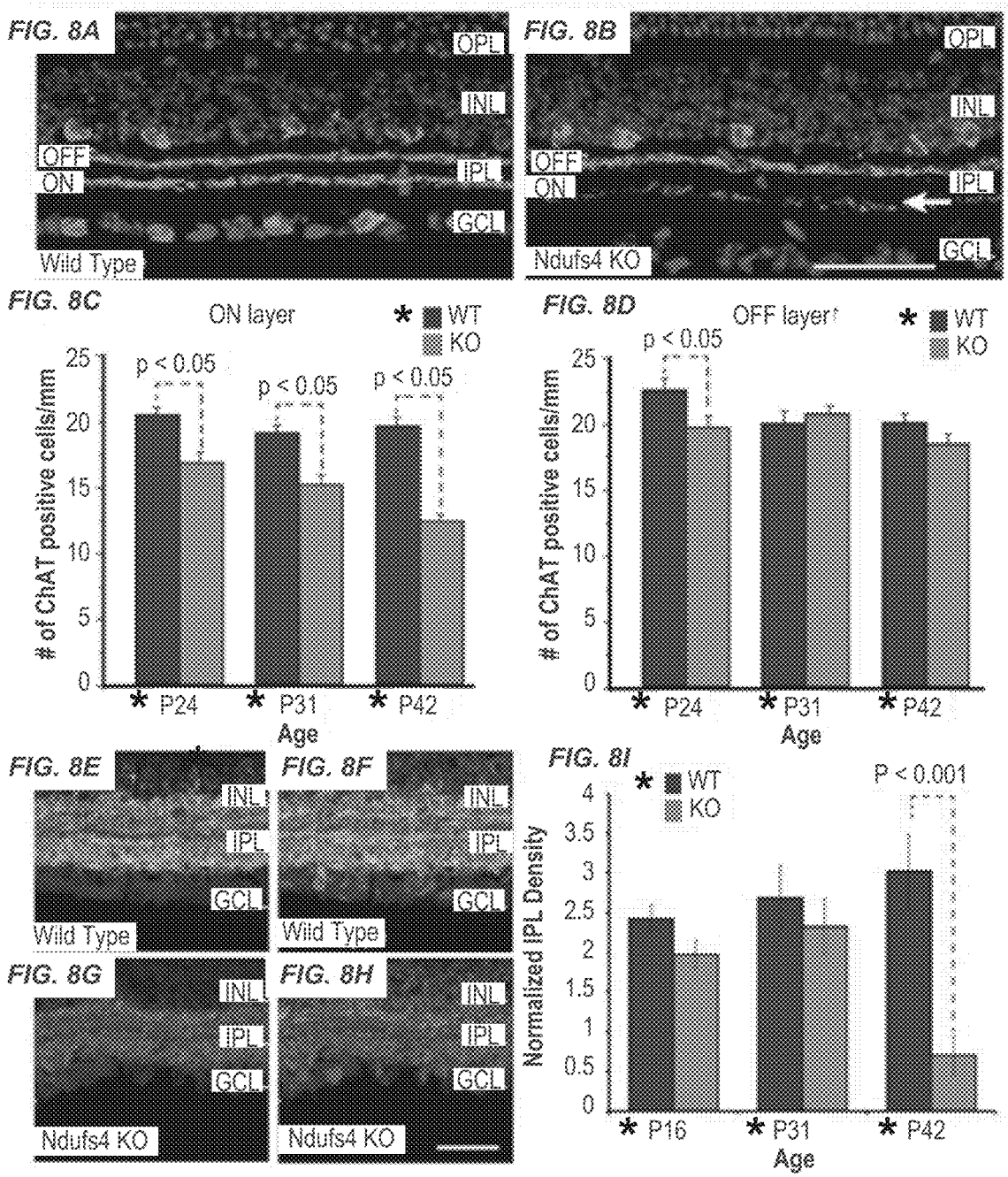

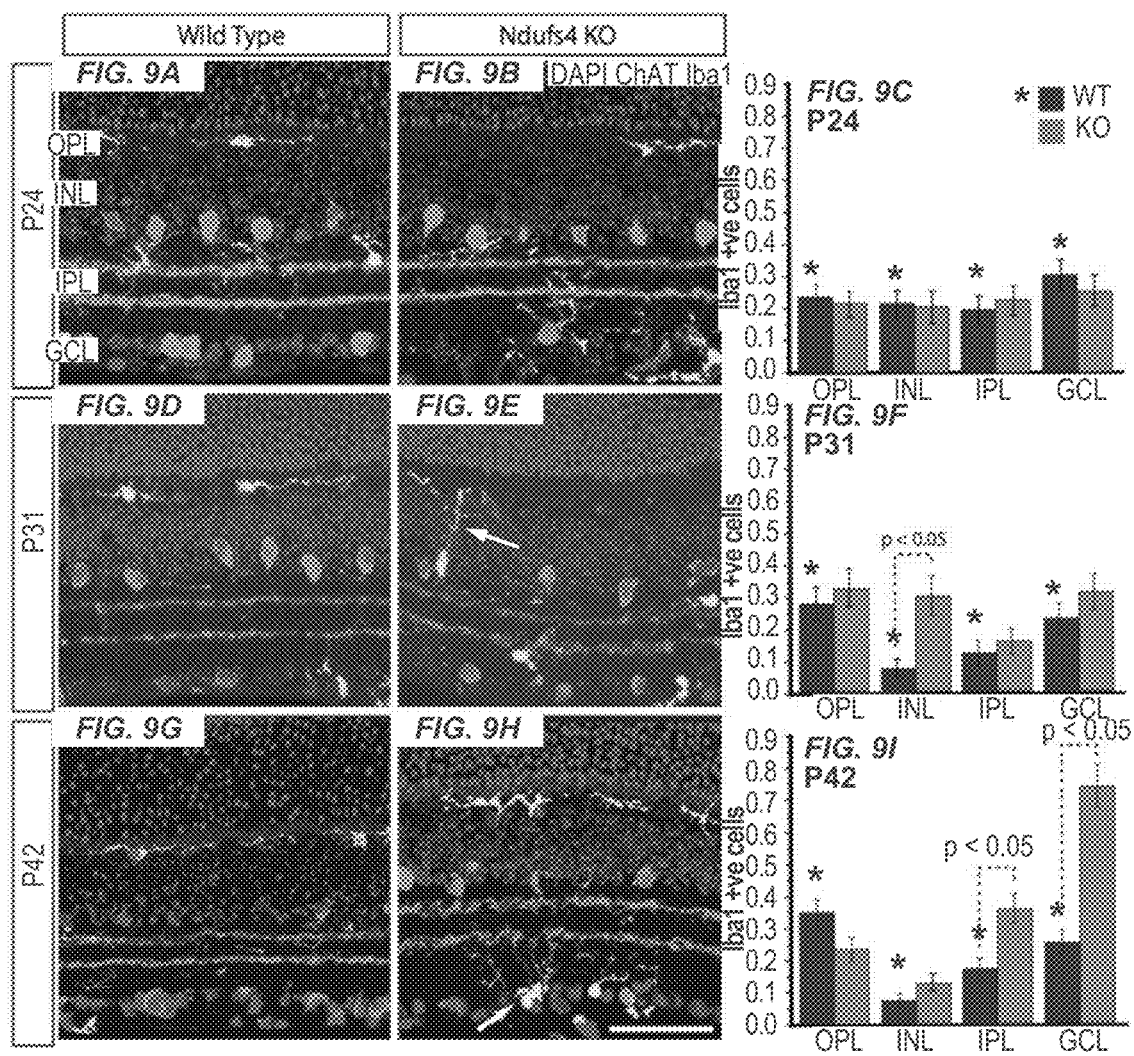

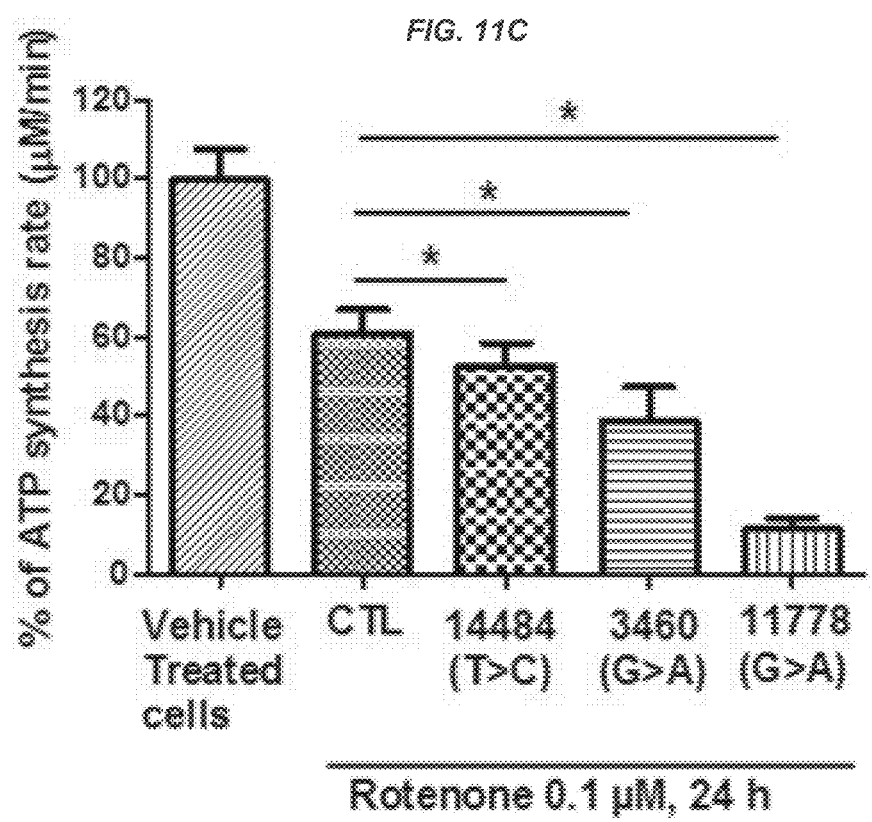

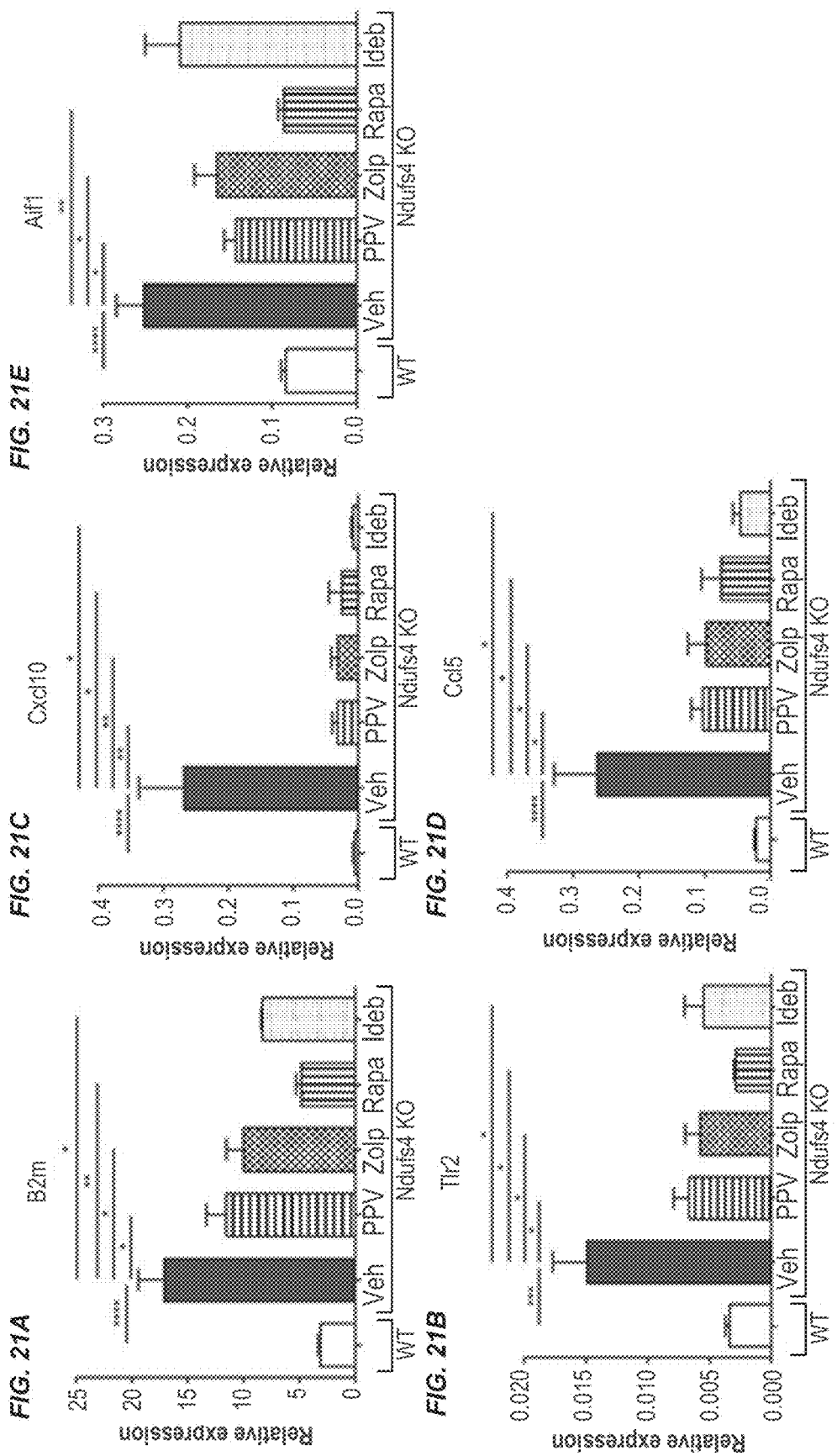

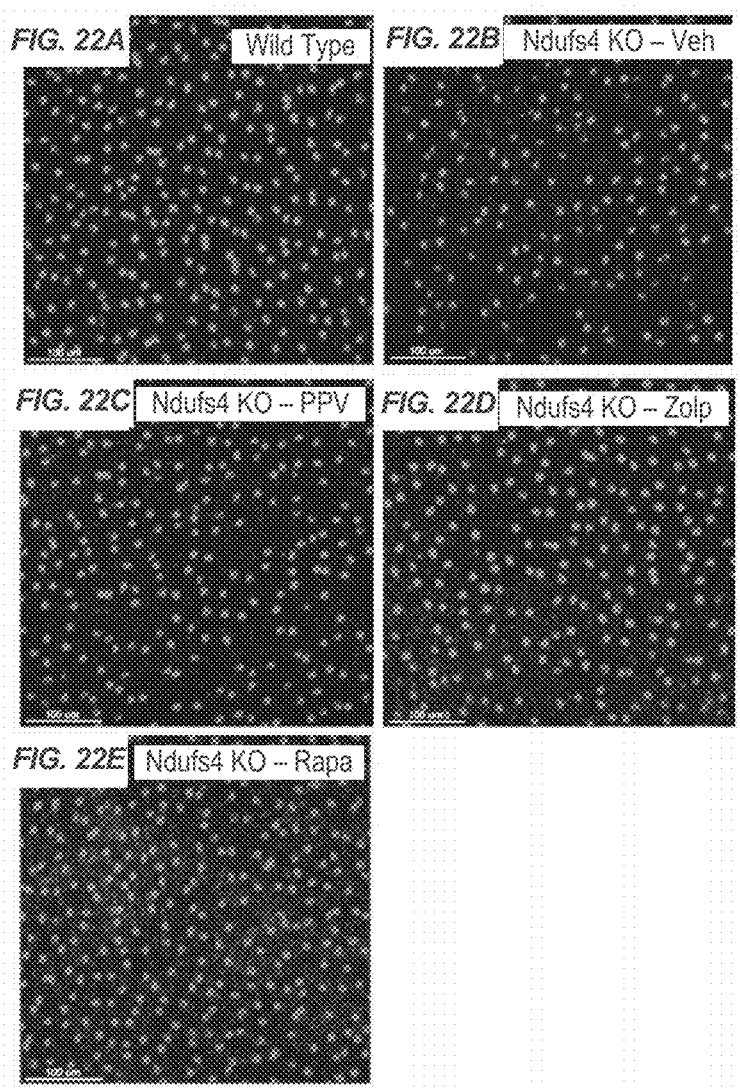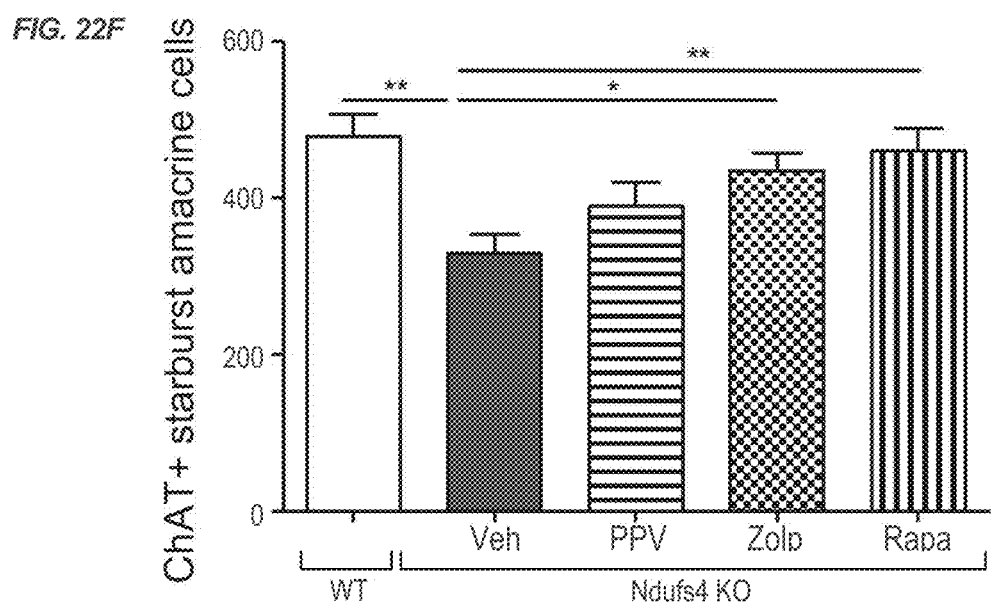

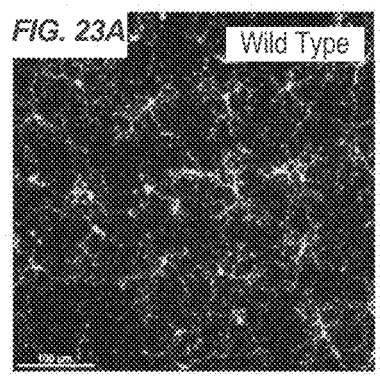
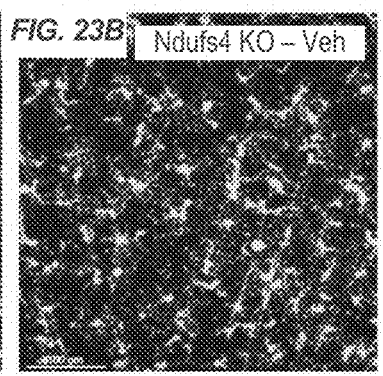
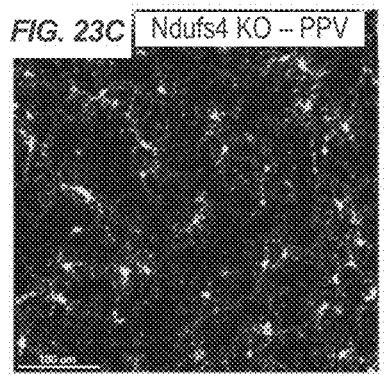
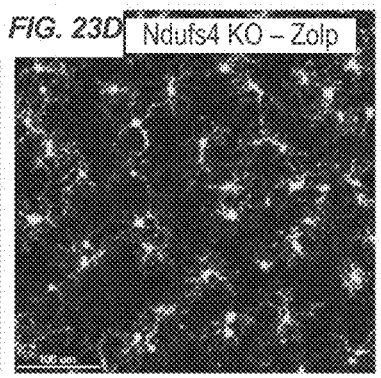
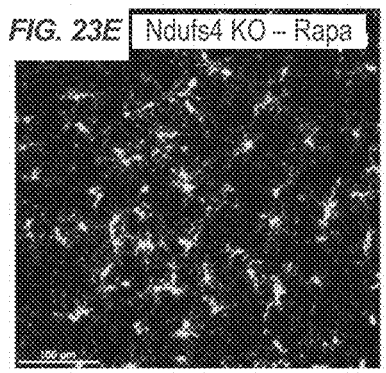
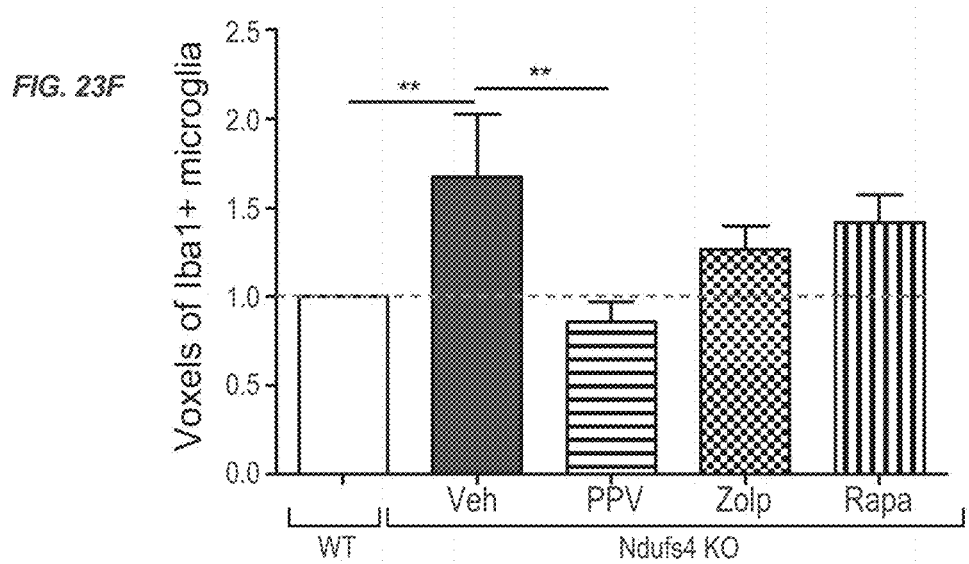

SEQUENCE LISTING

<160> NUMBER OF SEQ ID NOS: 52

<210> SEQ ID NO 1
<211> LENGTH: 20
<212> TYPE: DNA
<213> ORGANISM: Artificial Sequence
<220> FEATURE:
<223> OTHER INFORMATION: Synthetic forward primer for Actb

<400> SEQUENCE: 1

-continued atgtggatca gcaagcagga                                          20

<210> SEQ ID NO 2
<211> LENGTH: 23
<212> TYPE: DNA
<213> ORGANISM: Artificial Sequence
<220> FEATURE:
<223> OTHER INFORMATION: Synthetic forward primer for Aif1

<400> SEQUENCE: 2
atcaacaagc aattcctcga tga                                      23

<210> SEQ ID NO 3
<211> LENGTH: 21
<212> TYPE: DNA
<213> ORGANISM: Artificial Sequence
<220> FEATURE:
<223> OTHER INFORMATION: Synthetic forward primer for B2m

<400> SEQUENCE: 3
cactgaattc accccactg a                                         21

<210> SEQ ID NO 4
<211> LENGTH: 20
<212> TYPE: DNA
<213> ORGANISM: Artificial Sequence
<220> FEATURE:
<223> OTHER INFORMATION: Synthetic forward primer for C1qa

<400> SEQUENCE: 4
acaatggcat ggtgggcata                                          20

<210> SEQ ID NO 5
<211> LENGTH: 20
<212> TYPE: DNA
<213> ORGANISM: Artificial Sequence
<220> FEATURE:
<223> OTHER INFORMATION: Synthetic forward primer for C1ra

<400> SEQUENCE: 5
ggagagctga ggacccaaaa                                          20

<210> SEQ ID NO 6
<211> LENGTH: 20
<212> TYPE: DNA
<213> ORGANISM: Artificial Sequence
<220> FEATURE:
<223> OTHER INFORMATION: Synthetic forward primer for Ccl2

<400> SEQUENCE: 6
ggctggagag ctacaagagg                                          20

<210> SEQ ID NO 7
<211> LENGTH: 19
<212> TYPE: DNA
<213> ORGANISM: Artificial Sequence
<220> FEATURE:
<223> OTHER INFORMATION: Synthetic forward primer for Ccl5

<400> SEQUENCE: 7
tttgcctacc tctccctcg                                           19

<210> SEQ ID NO 8
<211> LENGTH: 23
<212> TYPE: DNA

```
<213> ORGANISM: Artificial Sequence
<220> FEATURE:
<223> OTHER INFORMATION: Synthetic forward primer for Ccl12

<400> SEQUENCE: 8
atttccacac ttctatgcct cct                                          23

<210> SEQ ID NO 9
<211> LENGTH: 21
<212> TYPE: DNA
<213> ORGANISM: Artificial Sequence
<220> FEATURE:
<223> OTHER INFORMATION: Synthetic forward primer for Cd68

<400> SEQUENCE: 9
tgtctgatct tgctaggacc g                                            21

<210> SEQ ID NO 10
<211> LENGTH: 20
<212> TYPE: DNA
<213> ORGANISM: Artificial Sequence
<220> FEATURE:
<223> OTHER INFORMATION: Synthetic forward primer for Cd86

<400> SEQUENCE: 10
cacaagaagc cgaatcagcc                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic forward primer for Cxcl9

<400> SEQUENCE: 11
ccaagcccca attgcaacaa                                              20

<210> SEQ ID NO 12
<211> LENGTH: 21
<212> TYPE: DNA
<213> ORGANISM: Artificial Sequence
<220> FEATURE:
<223> OTHER INFORMATION: Synthetic forward primer for Cxcl10

<400> SEQUENCE: 12
ccaagtgctg ccgtcatttt c                                            21

<210> SEQ ID NO 13
<211> LENGTH: 20
<212> TYPE: DNA
<213> ORGANISM: Artificial Sequence
<220> FEATURE:
<223> OTHER INFORMATION: Synthetic forward primer for Cx3cr1

<400> SEQUENCE: 13
gtcttcacgt tcggtctggt                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic forward primer for Fas

<400> SEQUENCE: 14
agcccgttgg agtgattcaa                                              20
```

<210> SEQ ID NO 15
<211> LENGTH: 19
<212> TYPE: DNA
<213> ORGANISM: Artificial Sequence
<220> FEATURE:
<223> OTHER INFORMATION: Synthetic forward primer for Gapdh

<400> SEQUENCE: 15
tgcaccacca actgcttag					19

<210> SEQ ID NO 16
<211> LENGTH: 21
<212> TYPE: DNA
<213> ORGANISM: Artificial Sequence
<220> FEATURE:
<223> OTHER INFORMATION: Synthetic forward primer for Gfap

<400> SEQUENCE: 16
agaaggggaa ggccaaaaag t					21

<210> SEQ ID NO 17
<211> LENGTH: 20
<212> TYPE: DNA
<213> ORGANISM: Artificial Sequence
<220> FEATURE:
<223> OTHER INFORMATION: Synthetic forward primer for Icam1

<400> SEQUENCE: 17
ttctcatgcc gcacagaact					20

<210> SEQ ID NO 18
<211> LENGTH: 20
<212> TYPE: DNA
<213> ORGANISM: Artificial Sequence
<220> FEATURE:
<223> OTHER INFORMATION: Synthetic forward primer for Mapk1

<400> SEQUENCE: 18
cgcctactca agcacctgaa					20

<210> SEQ ID NO 19
<211> LENGTH: 20
<212> TYPE: DNA
<213> ORGANISM: Artificial Sequence
<220> FEATURE:
<223> OTHER INFORMATION: Synthetic forward primer for Mmp9

<400> SEQUENCE: 19
ctctaagcct gacccaaggc					20

<210> SEQ ID NO 20
<211> LENGTH: 21
<212> TYPE: DNA
<213> ORGANISM: Artificial Sequence
<220> FEATURE:
<223> OTHER INFORMATION: Synthetic forward primer for Mmp12

<400> SEQUENCE: 20
tggtacacta gcccatgctt t					21

<210> SEQ ID NO 21
<211> LENGTH: 20
<212> TYPE: DNA
<213> ORGANISM: Artificial Sequence
<220> FEATURE:

```
<223> OTHER INFORMATION: Synthetic forward primer for Ndufs4

<400> SEQUENCE: 21
gagcacatcc acttggaagc                                           20

<210> SEQ ID NO 22
<211> LENGTH: 20
<212> TYPE: DNA
<213> ORGANISM: Artificial Sequence
<220> FEATURE:
<223> OTHER INFORMATION: Synthetic forward primer for Nes

<400> SEQUENCE: 22
agaggaccca aggcatttcg                                           20

<210> SEQ ID NO 23
<211> LENGTH: 20
<212> TYPE: DNA
<213> ORGANISM: Artificial Sequence
<220> FEATURE:
<223> OTHER INFORMATION: Synthetic forward primer for Opa1

<400> SEQUENCE: 23
cccagctcag aagaccttgc                                           20

<210> SEQ ID NO 24
<211> LENGTH: 20
<212> TYPE: DNA
<213> ORGANISM: Artificial Sequence
<220> FEATURE:
<223> OTHER INFORMATION: Synthetic forward primer for Tlr2

<400> SEQUENCE: 24
cagtggccag aaaagatgcg                                           20

<210> SEQ ID NO 25
<211> LENGTH: 21
<212> TYPE: DNA
<213> ORGANISM: Artificial Sequence
<220> FEATURE:
<223> OTHER INFORMATION: Synthetic forward primer for Tlr3

<400> SEQUENCE: 25
gagccacagt gatagatggc a                                         21

<210> SEQ ID NO 26
<211> LENGTH: 20
<212> TYPE: DNA
<213> ORGANISM: Artificial Sequence
<220> FEATURE:
<223> OTHER INFORMATION: Synthetic forward primer for Tlr4

<400> SEQUENCE: 26
ctctggggag gcacatcttc                                           20

<210> SEQ ID NO 27
<211> LENGTH: 20
<212> TYPE: DNA
<213> ORGANISM: Artificial Sequence
<220> FEATURE:
<223> OTHER INFORMATION: Synthetic reverse primer for Actb

<400> SEQUENCE: 27
gggtgtaaaa cgcagctcag                                           20
```

```
<210> SEQ ID NO 28
<211> LENGTH: 22
<212> TYPE: DNA
<213> ORGANISM: Artificial Sequence
<220> FEATURE:
<223> OTHER INFORMATION: Synthetic reverse primer for Aif1

<400> SEQUENCE: 28
cagcattcgc ttcaaggaca ta                                              22

<210> SEQ ID NO 29
<211> LENGTH: 20
<212> TYPE: DNA
<213> ORGANISM: Artificial Sequence
<220> FEATURE:
<223> OTHER INFORMATION: Synthetic reverse primer for B2m

<400> SEQUENCE: 29
tctcgatccc agtagacggt                                                 20

<210> SEQ ID NO 30
<211> LENGTH: 20
<212> TYPE: DNA
<213> ORGANISM: Artificial Sequence
<220> FEATURE:
<223> OTHER INFORMATION: Synthetic reverse primer for C1qa

<400> SEQUENCE: 30
gccgttctag tcgggaaaca                                                 20

<210> SEQ ID NO 31
<211> LENGTH: 20
<212> TYPE: DNA
<213> ORGANISM: Artificial Sequence
<220> FEATURE:
<223> OTHER INFORMATION: Synthetic reverse primer for C1ra

<400> SEQUENCE: 31
ccaccccata gaacagggtc                                                 20

<210> SEQ ID NO 32
<211> LENGTH: 20
<212> TYPE: DNA
<213> ORGANISM: Artificial Sequence
<220> FEATURE:
<223> OTHER INFORMATION: Synthetic reverse primer for Ccl2

<400> SEQUENCE: 32
ggtcagcaca gacctctctc                                                 20

<210> SEQ ID NO 33
<211> LENGTH: 21
<212> TYPE: DNA
<213> ORGANISM: Artificial Sequence
<220> FEATURE:
<223> OTHER INFORMATION: Synthetic reverse primer for Ccl5

<400> SEQUENCE: 33
cgactgcaag attggagcac t                                               21

<210> SEQ ID NO 34
<211> LENGTH: 23
<212> TYPE: DNA
<213> ORGANISM: Artificial Sequence
<220> FEATURE:
<223> OTHER INFORMATION: Synthetic reverse primer for Ccl12
```

```
<400> SEQUENCE: 34
atccagtatg gtcctgaaga tca                                           23

<210> SEQ ID NO 35
<211> LENGTH: 22
<212> TYPE: DNA
<213> ORGANISM: Artificial Sequence
<220> FEATURE:
<223> OTHER INFORMATION: Synthetic reverse primer for Cd68

<400> SEQUENCE: 35
gagagtaacg gccttttgt ga                                             22

<210> SEQ ID NO 36
<211> LENGTH: 20
<212> TYPE: DNA
<213> ORGANISM: Artificial Sequence
<220> FEATURE:
<223> OTHER INFORMATION: Synthetic reverse primer for Cd86

<400> SEQUENCE: 36
tgtcagcgtt actatcccgc                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic reverse primer for Cxcl9

<400> SEQUENCE: 37
agtccggatc taggcaggtt                                               20

<210> SEQ ID NO 38
<211> LENGTH: 21
<212> TYPE: DNA
<213> ORGANISM: Artificial Sequence
<220> FEATURE:
<223> OTHER INFORMATION: Synthetic reverse primer for Cxcl10

<400> SEQUENCE: 38
ggctcgcagg gatgatttca a                                             21

<210> SEQ ID NO 39
<211> LENGTH: 20
<212> TYPE: DNA
<213> ORGANISM: Artificial Sequence
<220> FEATURE:
<223> OTHER INFORMATION: Synthetic reverse primer for Cx3cr1

<400> SEQUENCE: 39
gtcagtgatg ctcttgggct                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic reverse primer for Fas

<400> SEQUENCE: 40 cccctgcaa tttccgtttg                                                20

<210> SEQ ID NO 41
<211> LENGTH: 18
```

```
<212> TYPE: DNA
<213> ORGANISM: Artificial Sequence
<220> FEATURE:
<223> OTHER INFORMATION: Synthetic reverse primer for Gapdh

<400> SEQUENCE: 41
gatgcaggga tgatgttc                                                     18

<210> SEQ ID NO 42
<211> LENGTH: 21
<212> TYPE: DNA
<213> ORGANISM: Artificial Sequence
<220> FEATURE:
<223> OTHER INFORMATION: Synthetic reverse primer for Gfap

<400> SEQUENCE: 42
ggcagggctc cattttcaat c                                                 21

<210> SEQ ID NO 43
<211> LENGTH: 20
<212> TYPE: DNA
<213> ORGANISM: Artificial Sequence
<220> FEATURE:
<223> OTHER INFORMATION: Synthetic reverse primer for Icam1

<400> SEQUENCE: 43
tcctggcctc ggagacatta                                                   20

<210> SEQ ID NO 44
<211> LENGTH: 20
<212> TYPE: DNA
<213> ORGANISM: Artificial Sequence
<220> FEATURE:
<223> OTHER INFORMATION: Synthetic reverse primer for Mapk1

<400> SEQUENCE: 44
cacgaggtac acttcgctga                                                   20

<210> SEQ ID NO 45
<211> LENGTH: 20
<212> TYPE: DNA
<213> ORGANISM: Artificial Sequence
<220> FEATURE:
<223> OTHER INFORMATION: Synthetic reverse primer for Mmp9

<400> SEQUENCE: 45
ccgtgggagg tatagtggga                                                   20

<210> SEQ ID NO 46
<211> LENGTH: 21
<212> TYPE: DNA
<213> ORGANISM: Artificial Sequence
<220> FEATURE:
<223> OTHER INFORMATION: Synthetic reverse primer for MMp12

<400> SEQUENCE: 46
agtccacgtt tctgcctcat c                                                 21

<210> SEQ ID NO 47
<211> LENGTH: 21
<212> TYPE: DNA
<213> ORGANISM: Artificial Sequence
<220> FEATURE:
<223> OTHER INFORMATION: Synthetic reverse primer for Ndufs4

<400> SEQUENCE: 47
```

```
gatgtgctct tctggaacac c                                              21

<210> SEQ ID NO 48
<211> LENGTH: 20
<212> TYPE: DNA
<213> ORGANISM: Artificial Sequence
<220> FEATURE:
<223> OTHER INFORMATION: Synthetic reverse primer for Nes

<400> SEQUENCE: 48
tgccttcaca ctttcctccc                                                20

<210> SEQ ID NO 49
<211> LENGTH: 21
<212> TYPE: DNA
<213> ORGANISM: Artificial Sequence
<220> FEATURE:
<223> OTHER INFORMATION: Synthetic reverse primer for Opa1

<400> SEQUENCE: 49
ccaatttggg acctgcagtg a                                              21

<210> SEQ ID NO 50
<211> LENGTH: 20
<212> TYPE: DNA
<213> ORGANISM: Artificial Sequence
<220> FEATURE:
<223> OTHER INFORMATION: Synthetic reverse primer for Tlr2

<400> SEQUENCE: 50
cctccagcgt ctgaggaatg                                                20

<210> SEQ ID NO 51
<211> LENGTH: 21
<212> TYPE: DNA
<213> ORGANISM: Artificial Sequence
<220> FEATURE:
<223> OTHER INFORMATION: Synthetic reverse primer for Tlr3

<400> SEQUENCE: 51
tccagcagaa gagacacaac a                                              21

<210> SEQ ID NO 52
<211> LENGTH: 20
<212> TYPE: DNA
<213> ORGANISM: Artificial Sequence
<220> FEATURE:
<223> OTHER INFORMATION: Synthetic reverse primer for Tlr4

<400> SEQUENCE: 52
tgctcaggat tcgaggcttt                                                20
```

METHODS FOR TREATING MITOCHONDRIAL DISEASES

CROSS-REFERENCES TO RELATED APPLICATIONS

This application is a continuation of International Patent Application No. PCT/US2016/064779 filed Dec. 2, 2016, which claims the benefit of and priority to U.S. Provisional Application No. 62/262,792, filed Dec. 3, 2015, the disclosures of which are herein incorporated by reference in their entirety for all purposes.

REFERENCE TO SUBMISSION OF A SEQUENCE LISTING AS A TEXT FILE

The Sequence Listing written in file SEQ_070772-222310US-1089574.txt created on Sep. 13, 2018, 11,146 bytes, machine format IBM-PC, MS-Windows operating system, is hereby incorporated by reference in its entirety for all purposes.

BACKGROUND OF THE INVENTION

Mitochondrial diseases are a clinically heterogeneous group of disorders of mitochondrial metabolism that can arise from a genetic mutation in nuclear or mitochondrial DNA. These genetic mutations may be maternally inherited, inherited as conventional Mendelian disorders, or acquired as new somatic mutations. The mutation may affect mitochondrial DNA replication, transcription, the transport of macromolecules into or out of mitochondria, or the function of macromolecules at their site of action within mitochondria.

Inherited forms of mitochondrial diseases have a high mortality and morbidity. The most severe forms, such as Leigh syndrome (e.g., subacute sclerosing encephalopathy) have a mortality of up to 50% a year after diagnosis. The epidemiology of the inherited forms of mitochondrial diseases is largely unknown. It has been estimated that between 1 in 4000 and 1 in 1000 live births in the U.S. will be diagnosed with a mitochondrial disease before the age of 10 years.

Mitochondria generate energy in the form of adenosine triphosphate (ATP) via oxidative phosphorylation using carbohydrates, proteins, and fatty acids as an energy source. The oxidative phosphorylation system consists of five multimeric protein complexes: complex I-IV form the respiratory chain and complex V is ATP synthetase. Electron carriers of the system are co-enzyme $Q_{10}$ and cytochrome C. Reduced cofactors generated from the intermediate metabolism of carbohydrates, proteins, and fatty acids donate electrons to complexes I and II. Electrons are transferred from electron donors to acceptors in redox reactions which are linked to the expulsion of protons from the mitochondrial matrix to the intermembrane space by complexes III and IV. This forms an electrochemical gradient that is used by complex V to synthesize ATP. Some key proteins of the respiration chain are encoded by mitochondrial DNA (mtDNA) which also encodes 24 RNA genes that are necessary for intra-mitochondrial protein synthesis. However, the majority of components of the oxidative phosphorylation system and proteins required for synthesis, expression and regulation of the mitochondrial genes are encoded by nuclear DNA. Therefore, a mitochondrial disease may be caused by genetic mutations in nuclear DNA or mtDNA.

There remains a need in the art for pharmaceutically effective drugs to treat mitochondrial diseases. The present invention satisfies this need and provides additional advantages.

BRIEF SUMMARY OF THE INVENTION

In one aspect, provided herein is a method for preventing, alleviating (e.g., one or more symptoms of), attenuating the progression of, or treating a mitochondrial disease in a subject in need thereof. The method comprises administering to the subject a therapeutically effective amount of a drug selected from the group consisting of papaverine, zolpidem, a nucleotide metabolism inhibitor, methoxamine, methenamine, pharmaceutically acceptable salts thereof, analogs thereof, and combinations thereof. In some embodiments, the nucleotide metabolism inhibitor is selected from the group consisting of methotrexate, azathioprine, fluorouracil, zidovudine, pharmaceutically acceptable salts thereof, analogs thereof, and combinations thereof. In some embodiments, the drug is administered orally (e.g., via pill or tablet dosage form), ocularly (e.g., via eye drops or intravitreally), topically, systemically, intravenously (e.g., via injectable dosage form), subcutaneously, intraperitoneally, intramuscularly, transdermally, or transmucosally (e.g., via aerosol).

In some instances, the therapeutically effective amount of the drug is an amount sufficient to stimulate mitochondrial ATP synthesis and/or to inhibit the induction of one or more inflammatory genes.

In some embodiments, the method also comprises administering a therapeutically effective amount of rapamycin, a pharmaceutically acceptable salt thereof, or an analog thereof. In some instances, rapamycin is administered orally, ocularly, topically, systemically, intravenously, subcutaneously, intraperitoneally, intramuscularly, transdermally, or transmucosally. In some instances, the therapeutically effective amount of rapamycin is an amount sufficient to inhibit the induction of one or more inflammatory genes.

In other embodiments, the method also comprises administering a therapeutically effective amount of idebenone, a pharmaceutically acceptable salt thereof, or an analog thereof. In some instances, idebenone is administered orally, ocularly, topically, systemically, intravenously, subcutaneously, intraperitoneally, intramuscularly, transdermally, or transmucosally. In some instances, the therapeutically effective amount of idebenone is an amount sufficient to stimulate mitochondrial ATP synthesis and/or to inhibit the induction of one or more inflammatory genes.

In some embodiments, the mitochondrial disease leads to vision loss or blindness. In particular embodiments, the mitochondrial disease is selected from the group consisting of Leigh syndrome; Leber's hereditary optic neuropathy (LHON); Alpers-Huttenlocher syndrome; ataxia neuropathy syndromes (ANS); chronic progressive external opthalmoplegia (CPEO); diabetes mellitus and deafness (DAD); dominant optic atrophy (DOA); Friedreich's ataxia (FRDA); infantile myopathy and lactic acidosis; Kearns-Sayre Syndrome (KSS); myoclonic epilepsy with ragged red fibers (MERRF); mitochondrial myopathy, encephalomyopathy, lactic acidosis, stroke (MELAS); myoclonic epilespy myopathy sensory ataxia (MEMSA); mitochondrial neurogastrointestinal encephalopathy (MNGIE); neuropathy, ataxia, retinitis pigmentosa, and ptosis (NARP); Pearson syndrome; and Sengers syndrome.

In some embodiments, the subject has a likelihood of having or developing the mitochondrial disease. In some instances, the subject has at least one genetic mutation associated with the mitochondrial disease.

In some embodiments, the subject is clinically asymptomatic. In other embodiments, the subject has at least one clinical symptom of the mitochondrial disease, such as, e.g., vision loss or blindness.

In another aspect, provided herein is a method for preventing, alleviating (e.g., one or more symptoms of), attenuating the progression of, or treating a mitochondrial disease in a subject in need thereof. In some embodiments, the method comprises administering to the subject a therapeutically effective amount of rapamycin, a pharmaceutically acceptable salt thereof, or an analog thereof. In particular embodiments, the mitochondrial disease is selected from the group consisting of Leber's hereditary optic neuropathy (LHON); Alpers-Huttenlocher syndrome; ataxia neuropathy syndromes (ANS); chronic progressive external opthalmoplegia (CPEO); diabetes mellitus and deafness (DAD); dominant optic atrophy (DOA); Friedreich's ataxia (FRDA); infantile myopathy and lactic acidosis; Kearns-Sayre Syndrome (KSS); myoclonic epilepsy with ragged red fibers (MERRF); mitochondrial myopathy, encephalomyopathy, lactic acidosis, stroke (MELAS); myoclonic epilepsy myopathy sensory ataxia (MEMSA); mitochondrial neurogastrointestinal encephalopathy (MNGIE); neuropathy, ataxia, retinitis pigmentosa, and ptosis (NARP); Pearson syndrome; and Sengers syndrome. In certain embodiments, the mitochondrial disease is not Leigh syndrome.

In some instances, rapamycin is administered orally, ocularly, topically, systemically, intravenously, subcutaneously, intraperitoneally, intramuscularly, transdermally, or transmucosally. In other instances, the therapeutically effective amount of rapamycin is an amount sufficient to inhibit the induction of one or more inflammatory genes.

In some embodiments, the method further comprises administering a therapeutically effective amount of a drug selected from the group consisting of papaverine, zolpidem, a nucleotide metabolism inhibitor, methoxamine, methenamine, idebenone, pharmaceutically acceptable salts thereof, analogs thereof, and combinations thereof. In some instances, the nucleotide metabolism inhibitor is selected from the group consisting of methotrexate, azathioprine, fluorouracil, zidovudine, pharmaceutically acceptable salts thereof, and analogs thereof. In some embodiments, the drug is administered orally, ocularly, topically, systemically, intravenously, subcutaneously, intraperitoneally, intramuscularly, transdermally, or transmucosally. In some cases, the therapeutically effective amount of the drug is an amount sufficient to stimulate mitochondrial ATP synthesis and/or to inhibit the induction of one or more inflammatory genes.

In some embodiments, the subject has a likelihood of having or developing the mitochondrial disease. In some instances, the subject has at least one genetic mutation associated with the mitochondrial disease.

In some embodiments, the subject is clinically asymptomatic. In other embodiments, the subject has at least one clinical symptom of the mitochondrial disease, such as, e.g., vision loss or blindness.

Other objects, features, and advantages of the present invention will be apparent to one of skill in the art from the following detailed description and figures.

BRIEF DESCRIPTION OF THE DRAWINGS

FIG. 1A shows decreased firing of RGC neurons from Ndufs4 KO mice begins at P32. MEA recording of Ndufs4 KO mice at P16, P25, P32, P35, P37, P45. Representative ERG of wild type control (FIG. 1B) and Ndufs4 KO mouse at P34 (FIG. 1C). Statistical significance determined Kruskal-Wallis ANOVA test. * $P<0.05$.

FIGS. 2A-2F show cell loss in the RGC layer of Ndufs4 mice measured by DAPI staining and Brn3a immunofluorescent labeling. Representative images of immunofluorescent labeling for Brn3a (green; marker for retinal ganglion cells) in transverse retinal sections from P42 wild type (FIGS. 2A and 2C) and littermate Ndufs4 KO (FIGS. 2B and 2D) animals. FIGS. 2C and 2D show ChAT (red; marker for starburst amacrine cells) immunolabeling with DAPI cell staining (blue) overlaid on the images from FIGS. 2A and 2B, respectively. FIG. 2E provides a bar graph showing counts of DAPI positive, ChAT negative cells in the GCL of wild type and Ndufs4 KO mice at P24, P31 and P42. FIG. 2F depicts a bar graph showing counts of Brn3a positive, ChAT negative cells in the GCL of P16, P31 and P42 wild type and Ndufs4 KO mice. Statistical comparisons were performed using 2 tailed students t test. Scale bar=100 mm. Statistical significance determined by student's t test.

FIGS. 7A-7H provide confirmation of astrocyte activation, microgliosis, and inflammation through protein expression. Immunofluorescent staining of Ndufs4 KO and wild type retina at P30 of Cxcl10, p-NF-kB, Cd68, and Gfap along with DAPI (FIG. 7A). Bar graph of Cxcl10 mean staining intensity of the GCL and INL minus background mean intensity (FIG. 7B). Bar graph of p-NF-kB mean staining intensity of the GCL minus background mean intensity (FIG. 7C). Bar graph of Cd68 positive cells normalized to total DAPI cell count (FIG. 7D). Bar graph of Gfap mean staining intensity of the GCL minus background mean intensity (FIG. 7E). Graphical western blot analysis of B2M normalized to tubulin with western blot image below (FIG. 7F). Graphical western blot analysis of p-NF-kB normalized to tubulin with western blot image below (FIG. 7G). Graphical western blot analysis of Gfap normalized to tubulin with western blot image below (FIG. 7H). Statistical significance determined by student's t test. * P<0.05, **** P<0.0001. Scale bar=100 mm.

FIGS. 8A-8I show Starburst Amacrine cell loss in Ndufs4 KO retinas. Representative images of immunofluorescent labeling for ChAT (red), a marker of starburst Amacrine cells in transverse retinal sections from P42 wild type (FIG. 8A) and Ndufs4 KO (FIG. 8B) mice. The two strong bands of ChAT immunolabeling within the IPL correspond to terminal arbors originating from OFF starburst amacrine cells residing in the innermost region of the INL or ON starburst amacrine cells residing in the GCL (so-called displaced amacrine cells). DAPI cell staining (blue) highlights cell lamina within the retina. Arrow depicts loss of synaptic processes in the ON layer of ChAT labeled amacrine cells. Bar graphs showing cell counts of ChAT labelled neurons within the GCL (FIG. 8C, ON) or INL (FIG. 8D, OFF) in wild type or Ndufs4 KO mice at P24, P31 and P42. Representative images of immunolabeling for GAD67 (green) in transverse retinal sections from P42 wild type (FIGS. 8E and 8G) and littermate Ndufs4 KO mice (FIGS. 8F and 8H). Overlaid images of immunolabeling for ChAT (red) and cell staining for DAPI (blue) on the same sections demarcate retinal lamina as well as the starburst amacrine cell terminal zones in the IPL. FIG. 8I shows a bar graph showing normalized intensity levels of GAD67 immunoreactivity within the IPL of wild type and Ndufs4 KO mice at P16, P24 and P42. Scale bar=50 mm. Statistical significance determined by student's t test.

FIGS. 9A-9I show representative images and graphical representation of counts within the retina from P24 (FIGS. 9A, 9B, and 9C), P31 (FIGS. 9D, 9E, and 9F) and P42 (FIGS. 9G, 9H, and 9I) depicting the migration of Iba1 positive microglia in Ndufs4 KO retina over time. Immunofluorescently labeled retina from wild type (FIGS. 9A, 9D, 9G) and littermate Ndufs4 KO (FIGS. 9B, 9E, and 9H) for Iba1 (green) a marker of microglia and ChAT (red) a starburst amacrine cell marker. DAPI (blue) stained nuclei identify lamina within the retina. Bar graphs (FIGS. 9C, 9F, and 9I) showing cell counts of Iba1 positive microglia with a nucleus in defined lamina of the retina at P24 (FIG. 9C), P31 (FIG. 9F) and P42 (FIG. 9I). Statistical comparisons were performed using 2 tailed student's t-test. Scale bar=50 mm.

FIGS. 11A-11C shows the concentration-dependent effect of a mitochondrial complex I inhibitor on LHON mutant cells. Effect of rotenone on (FIG. 11A) control and 11778 (G>A) mutant cytoplasmic hybrids; and (FIG. 11B) control and 11778 (G>A) mutant lymphoblast's. Rotenone sensitivity of ATP synthesis is correlated with severity of disease mutation (FIG. 11C). Cells were treated with different concentrations of rotenone for 24 h and mitochondrial complex I-driven ATP synthesis was measured. The data is presented as average+standard deviation from three independent experiments and single asterisk signifies the statistical significance (P<0.05) between the control and LHON mutant cells.

In FIG. 13A, the x-axis displays mean fold change from plate median in bins of size 0.1 (duplicate) and the y-axis shows the number of drugs. Drugs that increased or decreased luciferase signal than plate median±two Median absolute deviations were considered preliminary 'hits'. The activators zolpidem and papaverine are shown above the respective bin corresponding to the response for the drug (FIG. 13B). In FIG. 13B the x-axis represents the drugs screened and the y-axis shows fold-change in ATP synthesis rate over the plate median.

FIG. 15A shows the concentration-dependent rotenone de-sensitization effect of papaverine on LHON mutant [11778 (G>A)] cells. Cells were treated with different concentrations of papaverine for 22 h and subsequently with rotenone (0.03 µM) for 2 h. Cells were permeabilized with streptolysin O and mitochondrial complex I-driven ATP synthesis was measured in presence of complex I substrates (malate/pyruvate). The data is presented as fold change over rotenone-treated cells±standard deviation from three independent experiments. FIG. 15B shows the concentration-dependent rotenone de-sensitization effect of zolpidem on LHON mutant (11778 G>A) cells. Cells were treated with different concentrations of zolpidem for 22 h and subsequently with rotenone (0.03 µM) for 2 h. Cells were permeabilized with streptolysin O and mitochondrial complex I-driven ATP synthesis was measured in presence of complex I substrates (malate/pyruvate). The data is presented as fold change over rotenone-treated cells±standard deviation from three independent experiments.

FIG. 16A shows a reversal of concentration-dependent rotenone de-sensitization effect of zolpidem on LHON mutant (11778 G>A) cells by PKA inhibitor H89. Cells were treated with either vehicle, Zolpidem (30 µM) or Zolpidem (30 µM) and H89 (3 µM) for 22 h and subsequently with rotenone (0.03 µM) for 2 h. Cells were permeabilized with streptolysin O and mitochondrial complex I-driven ATP synthesis was measured in presence of complex I substrates (malate/pyruvate). The data is presented as fold change over rotenone-treated cells±standard deviation from three independent experiments. FIG. 16B illustrates no effect of a GABAA receptor antagonist, bicuculline, on rotenone de-sensitization effect of zolpidem in LHON mutant (11778 G>A) cells. Cells were treated with either vehicle, zolpidem (30 μM) alone, or zolpidem (30 μM) and bicuculline (30 μM) for 22 h and subsequently with rotenone (0.03 μM) for 2 h. Cells were permeabilized with streptolysin O and mitochondrial complex I-driven ATP synthesis was measured in presence of complex I substrates (malate/pyruvate). The data is presented as fold change over rotenone-treated cells±standard deviation from one representative experiment

FIG. 18A shows no effect on rotenone de-sensitization effect of papaverine in LHON mutant (11778 G>A) cells by PKA inhibitor H89. Cells were treated with either vehicle, papaverine (30 μM) or papaverine (30 μM) and H89 (3 μM) for 22 h and subsequently with rotenone (0.03 μM) for 2 h. Cells were permeabilized with streptolysin O and mitochondrial complex I-driven ATP synthesis was measured in presence of complex I substrates (malate/pyruvate). The data is presented as fold change over rotenone-treated cells±standard deviation from one representative experiment. FIG. 18B illustrates the differential effect of papaverine on rotenone-induced ATP synthesis inhibition in intact and permeabilized LHON mutant (11778 G>A) cells. Intact cells were treated with different concentrations of papaverine and rotenone (0.03 μM) for 2 h. Intact cells were permeabilized with streptolysin O and mitochondrial complex I-driven ATP synthesis was measured in presence of complex I substrates (malate/pyruvate). Untreated LHON mutant cells were permeabilized by streptolysin O and treated with vehicle or different concentrations of papaverine and rotenone (0.03 μM). The data is presented as fold change over rotenone-treated cells±standard deviation from one representative experiment.

FIG. 19A depicts response to papaverine in control cybrids. FIG. 19B depicts response to papaverine in mutant cybrids.

FIGS. 21A-21E show that gene expression of innate immune and inflammatory markers are suppressed/inhibited with drug treatment. The graphs represent RNA expression of B2m (FIG. 21A), Tlr2 (FIG. 21B), Cxcl10 (FIG. 21C), Ccl5 (FIG. 21D), and Aif1 (FIG. 21E) in the wild type and Ndufs4 knockout retina. Bars represent mean delta Ct values normalized to housekeeping genes, Actb and Mapk1. Error bars represent standard error of the mean. Statistical significance was determined by two-tailed student's t test. * P<0.05,  P<0.01, ** P<0.0001.

FIGS. 22A-22F show that the Ndufs4 knockout (KO) mouse presents with a significant loss of starburst amacrine cells starting at postnatal 24 days. After two weeks (P21-P35) of intraperitoneal injections of rapamycin (Rapa) and zolpidem (Zolp), there was a significant protection of startburst amacrine cells from apoptosis. Additionally, papaverine (PPV) treatment showed less cell loss than vehicle (Veh) treated Ndufs4. 20× confocal images of whole retina stained with ChAT (marker of starburst amacrine cells) from wild type (FIG. 22A), Ndusf4 KO vehicle treated (FIG. 22B), Ndufs4 KO papaverine treated (FIG. 22C), Ndufs4 KO zolpidem treated (FIG. 22D), and Ndufs4 KO rapamycin treated (FIG. 22E) are shown. Median cell count of starburst amacrine cells from each group are summarized in FIG. 22F.

FIGS. 23A-23F show that the Ndufs4 knockout (KO) mice have an elevated innate immune and inflammatory response at P30. Shown is an increase in microglia activation at P35 by Iba1 staining of whole mount retinas. After two weeks (P21-P35) of intraperitoneal treatment with papaverine (PPV), there was a significant inhibition of microglia activation. Additionally, zolpidem (Zolp) treatment showed a decrease in microglia activation. 20× confocal images of whole retinas stained with Iba1 (marker of microglial activation) in wild type (FIG. 23A), Ndusf4 KO vehicle treated (FIG. 23B), Ndufs4 KO papaverine treated (FIG. 23C), Ndufs4 KO zolpidem treated (FIG. 23D), and Ndufs4 KO rapamycin treated (FIG. 23E) are shown. Median microglia volume (measured in voxels) for each group is summarized in FIG. 23F.

DETAILED DESCRIPTION OF THE INVENTION

I. Introduction

Figure 1A:
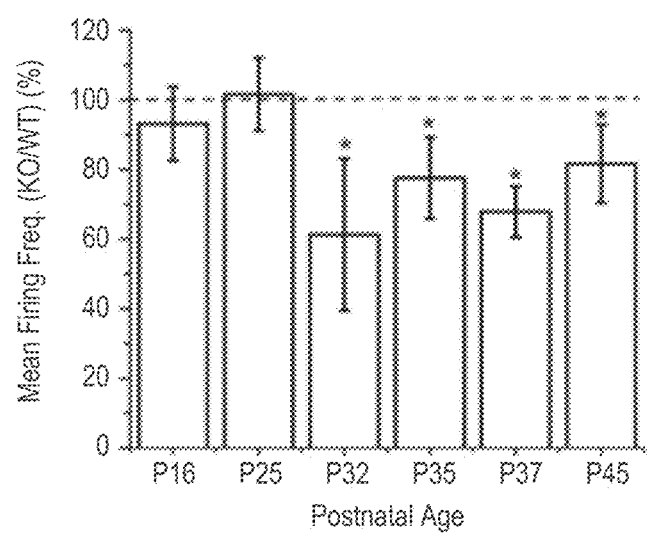
FIGS. 1A-1C show that complex I defects results in decreased retinal ganglion cell (RGC) function in Ndufs4 KO mice.

Provided herein are FDA-approved drugs that are useful for treating a mitochondrial disease in a patient in need thereof. Also provided are pharmaceutically effective drugs that can protect a patient from acquiring or developing the disease or one or more symptoms thereof. In some instances, the drugs disclosed herein can slow down or arrest the progression of a mitochondrial disease.

II. Definitions

As used herein, the following terms have the meanings ascribed to them unless specified otherwise.

As used herein, the terms "treat," "therapeutic," "prevent," and "prophylactic" are not intended to be absolute terms. The terms can refer to any delay in onset, reduction in the frequency or severity of adverse symptoms, improvement in patient comfort, etc. The effect of treatment can be compared to an individual or pool of individuals not receiving a given treatment, or to the same patient prior to, or after cessation of, treatment.

The term "treating" or "treatment" refers to the treating or treatment of a disease or medical condition (such as a mitochondrial disease) in a patient, such as a mammal (particularly a human or an animal) which includes: ameliorating the disease or medical condition, i.e., eliminating or causing regression of the disease or medical condition in a patient; suppressing the disease or medical condition, i.e., slowing or arresting the development of the disease or medical condition in a patient; or alleviating one or more symptoms of the disease or medical condition in a patient. The term encompasses the prophylactic treatment of a disease as to prevent or reduce the risk of acquiring or developing a specific disease, or to prevent or reduce the risk of disease recurrence. In some instances, the term can refer to any one of the following: ameliorating one or more symptoms of a mitochondrial disease; preventing the manifestation of such symptoms before they occur; slowing down or completely preventing the progression of the disease (as may be evident by longer periods between reoccurrence episodes, slowing down or prevention of the deterioration of symptoms, etc.); enhancing the onset of a remission period; slowing down the irreversible damage caused in the progressive-chronic stage of the disease (both in the primary and secondary stages); delaying the onset of said progressive stage, or any combination thereof.

The term "administer," "administering," "administration," and derivatives thereof refer to the process by which compounds, compositions, dosage forms and/or combinations disclosed herein are delivered to a subject for treatment or prophylactic purposes. Compounds, compositions, dosage forms and/or combinations disclosed herein are administered in accordance with good medical practices taking into account the subject's clinical condition, the site and method of administration, dosage, subject age, sex, body weight, and other factors known to the physician. For example, the terms "administering" or "administration" include providing, giving, dosing and/or prescribing compounds, compositions, dosage forms and/or combinations disclosed herein by a clinician or other clinical professional. These methods include, but are not limited to parenteral administration (e.g., intravenous, subcutaneous, intraperitoneal, intramuscular, intravascular, intrathecal, intranasal, intravitreal, infusion and local injection), transmucosal injection, oral administration, administration as a suppository, ocular administration, and topical administration.

Administration is by any route, including parenteral and transmucosal (e.g., buccal, sublingual, palatal, gingival, nasal, vaginal, rectal, transdermal or ocular). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. One skilled in the art will know of additional methods for administering a therapeutically effective amount of a compound of the present invention for preventing or relieving one or more symptoms associated with a disease.

The term "alleviation," "alleviating" or equivalents thereof, refers to both therapeutic treatment and prophylactic or preventative measures, wherein the object is to ameliorate, prevent, slow down (lessen), decrease, or inhibit a disease or condition such as one or more symptoms thereof. Those in need of treatment include those already with the disease or condition as well as those prone to having the disease or condition or those in whom the disease or condition is to be prevented.

The term "therapeutically effective amount," as used herein, refers to the amount or dose of a therapeutic agent sufficient to ameliorate the targeted condition or one or more symptoms of the targeted condition. A therapeutically effective amount can be a dose that produces a therapeutic effect for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins).

The term "analog" or "drug analog," in the context of a pharmaceutical drug refers to an analogous drug that either has (a) chemical or pharmacological similarities to the designated drug, or (b) only structural similarities to the designated drug, or (c) a different chemical structure but displaying similar pharmacological properties to the designated drug.

The term "pharmaceutically acceptable salt" include salts of the active compounds which are prepared with relatively nontoxic acids or bases, depending on the particular substituents found on the compounds described herein. The term refers to a salt that is pharmaceutically acceptable and has the desired pharmacokinetic properties. By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in Berge et al., J. Pharmaceutical Sciences, 1977, 66: 1. Particularly suitable salts include acid addition salts formed with inorganic acids (e.g., hydrochloride and hydrobromic acids) and organic acids (e.g., acetic acid, citric acid, maleic acid, and the alkane- and arene-sulfonic acids such as methanesulfonic acid and benzenesulfonic acid).

When drug compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds described herein contain relatively basic functionalities, acid addition salts can be obtained by contacting the neutral form of such compounds with a sufficient amount of the desired acid, either neat or in a suitable inert solvent. Examples of pharmaceutically-acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", Journal of Pharmaceutical Science, 1977, 66, 1-19). Compounds may contain both basic and acidic functionalities that allow the compounds to be converted into either base or acid addition salts.

The term "pharmaceutically acceptable carrier" refers to a carrier or a diluent that does not cause significant irritation to an organism and does not abrogate the biological activity and properties of the administered compound.

The term "nucleotide metabolism inhibitor" refers to a drug that can inactivate, inhibit, block, or reduce nucleotide, nucleoside or nucleic acid metabolism (e.g., a process of nucleic acid synthesis and degradation).

The term "an amount sufficient to stimulate mitochondrial ATP synthesis" refers to a therapeutically effective amount of a drug that when administered to a subject in need thereof can stimulate, activate, promote, induce or increase ATP synthesis by mitochondria in cells of the subject. In some cases, the amount can increase the rate of ATP synthesis.

The term "an amount sufficient to inhibit the induction of one or more inflammatory genes" refers to a therapeutically effective amount or dose of a drug that when administered to a subject in need thereof can inhibit, prevent, or block the induction or activity of one or more inflammatory or immune response genes in the subject. The term also includes an amount or dose of a pharmaceutical drug that inhibits, prevents or blocks the activity of an inflammatory gene product.

The terms "symptom," "clinical symptom" and "clinical feature," are used interchangeably to refer to subjective or objective evidence of a disease, disorder or condition experienced by a patient.

The term "subject," "individual" or "patient" typically refers to humans, but also to other animals including, e.g., other primates, rodents, canines, felines, equines, ovines, porcines, and the like.

III. Detailed Descriptions of Embodiments

A. Mitochondrial Diseases

The drugs disclosed herein can be administered to a subject having or suspected of having a mitochondrial disease. Non-limiting examples of mitochondrial diseases include Alpers-Huttenlocher syndrome; aminoglycoside-induced nonsyndromic deafness; ataxia neuropathy syndromes (ANS); autosomal progressive external ophthalmoplegia; Barth syndrome; beta-oxidation defects; carnitine-acyl-carnitine deficiency; carnitine deficiency; chronic progressive external ophthalmoplegia (CPEO); coenzyme $Q_{10}$ deficiency; complex II deficiency (cardiomyopathy and encephalopathy); complex II deficiency (optic atrophy and ataxia); complex III deficiency (hypokalemia and lactic acidosis); complex IV deficiency (COX deficiency); complex V deficiency; CPT I deficiency; CPT II deficiency; diabetes mellitus and deafness (DAD); dominant optic atrophy (DOA); encephalopathy and liver failure; encephalopathy with complex V deficiency; encephalopathy, liver failure, renal tubulopathy; Friedreich's ataxia (FRDA); hepatopathy and ketoacidosis; hypertropic cardiomyopathy; hypotonia, encephalopathy, renal tubulopathy, lactic acidosis; hypotonia, movement disorder and Leigh syndrome with methylmalonic aciduria; infantile myopathy and lactic acidosis; Kearns-Sayre syndrome (KSS); lactic acidosis; lactic acidosis, developmental failure, and dysmorphism; Leber's hereditary optic neuropathy (LHON); Leigh syndrome and optic atrophy with COX deficiency; Leigh syndrome with complex I deficiency; Leigh syndrome with complex II deficiency; Leigh syndrome, liver failure and lactic acidosis; leukodystrophy and polymicrogyria; leukodystrophy and renal tubulopathy; leukodystrophy with complex II deficiency; leukoencephalopathy with brainstem and spinal cord involvement and lactate elevation (LBSL); long-chain acyl-CoA dehydrogenase deficiency (LCAD); long-chain 3-hydroxyacyl-CoA dehydrogenase deficiency (LCHAD); Luft disease; medium-chain acyl-CoA dehydrogenase deficiency; mitochondrial DNA depletion; mitochondrial encephalopathy; mitochondrial encephalomyopathy with lactacidosis and stroke (MELAS); mitochondrial encephalomyopathy with combined RC deficiency; mitochondrial myopathy; mitochondrial phosphate carrier deficiency; mitochondrial recessive ataxia syndrome (MERAS); multiple acyl-CoA dehydrogenase deficiency (MAD); myoclonic epilepsy myopathy sensory ataxia (MEMSA); myoclonic epilepsy with ragged red fibers (MERRF); mitochondrial neurogastrointestinal encephalopathy (MNGIE); myopathy and sideroblastic anemia; myopathy with cataract and combined RC deficiency; neurogenic weakness with ataxia and retinitis pigmentosa (NARP); nonsyndromic sensorineural deafness; Pearson Syndrome; pyruvate carboxylase deficiency; pyruvate dehydrogenase deficiency; reversible hepatopathy; sensory ataxia neuropathy, dysarthria, ophthalmoplegia (SANDO); Sengers syndrome; short-chain acyl-CoA dehydrogenase deficiency (SCAD or SCHAD); spinal muscular atrophy; spinocerebellar ataxia with epilepsy (MIRAS or SCAE); and very long-chain acyl-CoA dehydrogenase deficiency (VLCAD).

The drugs can be administered to a subject to prevent, alleviate, attenuate the progression of, or treat a mitochondrial disease. In some embodiments, the mitochondrial disease is any mitochondrial disease including Leigh syndrome; Leber's hereditary optic neuropathy (LHON); Alpers-Huttenlocher syndrome; ataxia neuropathy syndromes (ANS); chronic progressive external opthalmoplegia (CPEO); diabetes mellitus and deafness (DAD); dominant optic atrophy (DOA); Friedreich's ataxia (FRDA); infantile myopathy and lactic acidosis; Kearns-Sayre Syndrome (KSS); myoclonic epilepsy with ragged red fibers (MERRF); mitochondrial myopathy, encephalomyopathy, lactic acidosis, stroke (MELAS); myoclonic epilespy myopathy sensory ataxia (MEMSA); mitochondrial neurogastrointestinal encephalopathy (MNGIE); neuropathy, ataxia, retinitis pigmentosa, and ptosis (NARP); Pearson syndrome; and Sengers syndrome.

In other embodiments, the mitochondrial disease is any mitochondrial disease except Leigh syndrome. For example, the mitochondrial disease can be Leber's hereditary optic neuropathy (LHON); Alpers-Huttenlocher syndrome; ataxia neuropathy syndromes (ANS); chronic progressive external opthalmoplegia (CPEO); diabetes mellitus and deafness (DAD); dominant optic atrophy (DOA); Friedreich's ataxia (FRDA); infantile myopathy and lactic acidosis; Kearns-Sayre Syndrome (KSS); myoclonic epilepsy with ragged red fibers (MERRF); mitochondrial myopathy, encephalomyopathy, lactic acidosis, stroke (MELAS); myoclonic epilespy myopathy sensory ataxia (MEMSA); mitochondrial neurogastrointestinal encephalopathy (MNGIE); neuropathy, ataxia, retinitis pigmentosa, and ptosis (NARP); Pearson syndrome; and Sengers syndrome.

In some embodiments, the mitochondrial disease is LHON. In some embodiments, the mitochondrial disease is Alpers-Huttenlocher syndrome. In some embodiments, the mitochondrial disease is an ataxia neuropathy syndrome. In some embodiments, the mitochondrial disease is CPEO. In some embodiments, the mitochondrial disease is DAD. In some embodiments, the mitochondrial disease is DOA. In some embodiments, the mitochondrial disease is FRDA. In some embodiments, the mitochondrial disease is infantile myopathy and lactic acidosis. In some embodiments, the mitochondrial disease is KSS. In some embodiments, the mitochondrial disease is MERRF. In some embodiments, the mitochondrial disease is MELAS. In some embodiments, the mitochondrial disease is MEMSA. In some embodiments, the mitochondrial disease is MNGIE. In some embodiments, the mitochondrial disease is NARP. In some embodiments, the mitochondrial disease is Pearson syndrome. In some embodiments, the mitochondrial disease is Sengers syndrome.

Leigh syndrome or subacute sclerosing encephalopathy usually develops late in the first year of life, although disease onset may occur in adulthood. Symptoms include seizures, altered states of consciousness, hypotonia, fatigue, nystagmus, poor reflexes, eating and swallowing difficulties, breathing difficulties, poor motor function, ataxia, dementia, and ventilator failure. Possible causes of Leigh syndrome include pyruvate dehydrogenase (PDHC) deficiency and respiratory chain enzyme defects (e.g., complex I, complex II, complex IV and complex V defects). The syndrome may be X-linked dominant, autosomal recessive, or maternally inherited. In some instances, Leigh syndrome is a spontaneous disease. Gene mutations associated with Leigh syndrome include, but are not limited to, mutations in genes encoding subunits of complex I (e.g., ND1, ND2, ND3, ND4, ND5, and ND6), genes encoding subunits of complex IV (e.g., COXIII), genes encoding subunits of complex V (e.g., ATPase), tRNA-encoding genes, (e.g., lysine-tRNA, valine-tRNA, and tryptophan-tRNA), and those described in, e.g., Finsterer et al., Pediatric Neurology, 2008, 39:223-235. Detailed descriptions of Leigh syndrome are found in, e.g., OMIM Entry Nos. 256000 and 220111.

Leber's hereditary optic neuropathy (LHON) can result in visual loss beginning in young adulthood (i.e., between on average 25 to about 35 years of age), eye disorder characterized by progressive loss of central vision due to degeneration of the optic nerves and retina. Detailed descriptions of LHON are found in, e.g., OMIM Entry Nos. 535000, 516000, 516001, 5160003, 516005, 516006, 516020, 516030, and 516060.

Alpers-Huttenlocher syndrome is an autosomal recessive disorder that can be characterized by psychomotor retardation, intractable epilepsy and liver failure in infants and young children. Clinical features of the syndrome include, but are not limited to delayed motor development, vomiting, multifocal seizures, status epilepticus, stupor, hypotonia, paralysis, delayed development at infancy, severe microcephaly, progressive encephalopathy, fetal akinesia, refractory neonatal convulsions, swallowing difficulties, liver failure, and optic atrophy. Detailed descriptions of Alpers-Huttenlocher syndrome are found in, e.g., OMIM Entry No. 203700.

Ataxia neuropathy syndromes include sensory ataxic neuropathy, dysarthria, and ophthalmoparesis (SANDO). SANDO is an autosomal recessive systemic disorder characterized mainly by adult onset of sensory ataxic neuropathy, dysarthria, and ophthalmoparesis resulting from mitochondrial dysfunction and associated with mtDNA depletion in skeletal muscle and peripheral nerve tissue. Other clinical features can include cognitive impairment, myopathy, gait and limb ataxia, seizures and hearing loss. Detailed descriptions of Alpers-Huttenlocher syndrome are found in, e.g., OMIM Entry No. 607459.

Chronic progressive external ophthalmoplegia syndrome (CPEO) can be an autosomal dominant disorder characterized by symptoms such as, but not limited to ptosis, paralysis of eye movement, retinal degeneration, visual myopathy, retinitis pigmentosa, dysfunction of the central nervous system, and mitochondrial dysfunction. The syndrome may be caused by one or more mtDNA mutations including an A3243G mtDNA point mutation. Detailed descriptions of CPEO are found in, e.g., OMIM Entry No. 157640.

Maternally inherited diabetes mellitus and deafness (MIDD or DAD) may be a specific manifestation of symptoms resulting from mitochondrial starving of the pancreas, which in turn leads to a diabetic condition, and accompanying deafness. Detailed descriptions of DAD are found in, e.g., OMIM Entry No. 520000.

Dominant optic atrophy (DOA) is a form of optic atrophy that can be caused by a mutation in the OPA1, OPA3, OPA4, or OPA5 gene. The neurologic disorder is characterized by clinical features including visual loss and sensorineural hearing loss in childhood, progressive external ophthalmoplegia, muscle cramps, hyperreflexia, ataxia, ptosis, hearing loss, myopathy and neuropathy. Detailed descriptions of DOA are found in, e.g., OMIM Entry Nos. 125250 and 165500.

Friedreich's ataxia (FRDA) is an autosomal recessive neurodegenerative disorder caused by a mutation in the frataxin gene that encodes for a mitochondrial iron chaperone. Symptoms of FRDA include, but are not limited to, progressive gait and limb ataxia, limb muscle weakness, reduced or absent lower limb reflexes, extensor plantar responses, dysarthria, decreased vibratory sense and proprioception, visual defects, pes cavus, hammertoe, and cardiomyopathy. Detailed descriptions of FRDA are found in, e.g., OMIM Entry No. 229300.

Infantile myopathy and lactic acidosis or infantile mitochondrial myopathy refers to a reversible COX deficiency. It can be characterized by severe hypotonia with onset in infancy, muscle weakness associated with lactic acid acidosis, hyporeflexia, hepatomegaly, macroglossia, waddling gait, a failure to thrive, and severe muscle weakness. Detailed descriptions of infantile myopathy and lactic acidosis are found in, e.g., OMIM Entry No. 500009.

Kearns-Sayre syndrome (KSS) refers to a slowly progressive mitochondrial disease characterized by paralysis of specific eye muscles, degeneration of the retinal caused by abnormal accumulation of pigmented material, and generally, onset before 20 years of age. Additional clinical features include, but are not limited to, cardiac conduction defects, cardiomyopathy, ataxia (incoordination of movements), elevated cerebrospinal fluid protein, deafness, dementia, kidney dysfunction, muscle weakness, growth retardation, short stature, diabetes, and neuropathy. Detailed descriptions of KSS are found in, e.g., OMIM Entry No. 530000.

Myoclonic epilepsy with ragged red fibers (MERRF) is a progressive myoclonic epilepsy that may be caused at least in part by mitochondrial dysfunction. MERRF is associated with ragged red fibers, clumps of diseased mitochondria that accumulate in the subsarcolemmal region of the muscle fiber. The "ragged red fibers" can be observed when muscle is stained with modified Gomori trichrome stain. Clinical features of MERRF include short stature, epileptic seizures, ataxia (impaired motor coordination), myoclonus (brief, sudden, twitching muscle spasms), hearing loss, lactic acidosis in the blood and/or cerebrospinal fluid, dementia, cardiac defects, eye abnormalities, speech impairment, and/or exercise intolerance. MERRF may be sporadic disease or a maternally inherited disease caused by a mtDNA mutation such as an A3844G and/or T8356C mtDNA mutations. Detailed descriptions of MERRF are found in, e.g., OMIM Entry No. 545000.

Myoclonic epilepsy myopathy sensory ataxia (MEMSA) is a type of autosomal recessive disorder caused by a mutation in the polymerase gamma (POLG) gene. Clinical features of the disorder include cerebellar ataxia, coordination defects, migraine, seizures, encephalopathy, myopathy, and exercise intolerance. Subjects with MEMSA do not have ophthalmoplegia.

Mitochondrial myopathy, encephalomyopathy, lactic acidosis, stroke (MELAS) is a mitochondrial disease characterized by symptoms such as but not limited to short statue, developmental delay, learning disabilities, attention-deficit disorder, mental impairment, dementia, recurrent vomiting, seizures, stroke-like episodes with focused neurological deficits, recurrent headaches, cognitive regression, muscle weakness, exercise intolerance, limb weakness, hearing loss, diabetes, loss of motor skills including speech, movement, or eating, loss of body sensations, partial paralysis, partial vision loss, lactic acid accumulation in blood and/or cerebrospinal fluid, peripheral nerve dysfunction, cardiac dysfunctions, kidney dysfunctions, and digestive abnormalities. It is a progressive neurodegenerative disorder with a typical onset between 2-15 years of age, but may occur at infancy or in adulthood. MELAS can be maternally inherited and due to a genetic mutation in mtDNA, such as an A3243G mutation. There are at least 17 different genetic mutations associated with MELAS. Detailed descriptions of MELAS are found in, e.g., OMIM Entry No. 540000.

Mitochondrial neurogastrointestinal encephalopathy (MNGIE) can manifest as symptoms such as, but not limited to, progressive external ophthalmoplegia, gastrointestinal dysmotility (e.g., pseudoobstruction), cachexia, diffuse leukoencephalopathy, cerebral, leukodystrophy, peripheral neuropathy, limb weakness, lactic acidosis, ragged red fibers, and mitochondrial dysfunction. Detailed descriptions of MNGIE are found in, e.g., OMIM Entry No. 603041.

Neuropathy, ataxia, retinitis pigmentosa, and ptosis (NARP) is a disease identified as the progressive set of symptoms associated with neuropathy, ataxia, retinitis pigmentosa, and ptosis, and in some cases dementia. Detailed descriptions of NARP are found in, e.g., OMIM Entry No. 551500.

Pearson syndrome refers to a mitochondrial disease characterized by, but not limited to, bone marrow dysfunction and pancreas dysfunction. Detailed descriptions of Pearson syndrome are found in, e.g., OMIM Entry No. 557000.

Sengers syndrome is also known as cardiomyopathic mitochondrial DNA depletion syndrome-10. The mitochondrial disease can be caused by a mutation in the AGK gene. The disorder is characterized by, but not limited to, congenital cataracts, hypertropuic cardiomyopathy, skeletal myopathy, hypotonia, exercise intolerance, and lactic acidosis. Detailed descriptions of Sengers syndrome are found in, e.g., OMIM Entry No. 212350.

A patient may exhibit one or more clinical features of a mitochondrial disease. Symptoms or clinical features of a mitochondrial disease include, but are not limited to, stroke, cerebellar ataxia, mental retardation, developmental delays, learning disability, cognitive decline, migraine, dementia, cortical blindness, spasticity (epilepsy or seizure), myoclonus, peripheral neuropathy, dementia, ophthalmonplegia externa, muscle weakness, loss of muscle coordination, dystonia, exercise intolerance, chronic fatigue, blepharoptosis, diabetes mellitus, short stature, delayed puberty, hypoparathyroidism, facial and oropharyngeal weakness, respiratory muscle weakness, hypertrophic cardiomyopathy, dilated cardiomyopathy, cardiac arrhythmia, congestive cardiomyopathy, defect in cardiac conduction, renal tubulopathy, sideroblastic anemia, hypertransaminase, neonatal liver failure, hepatic steatohepatitis, cholestatis, chronic liver failure, lipoma, pancreatic achylia, ileus, intestinal psudoobstruction, chronic diarrhea, iterative emesis, pigmentary retinopathy, atrophy of the optic nerve, restricted eye movement, visual deficiency, perceptive deafness (sensori-neural deafness), hearing loss, schizophrenia, behavior disorder, autism, developmental delay, neurological dysfunction, thyroid dysfunction, adrenal dysfunction, autonomic dysfunction, respiratory dysfunction/abnormalities, and any combination thereof.

The mitochondrial disease can affect a subject of any age. A human subject can be a newborn, neonatal infant (e.g. newborn to about 1 month old), infant (e.g., about 1 month old to about 2 years old), child (e.g., about 2 years old to about 10 years old), adolescent (e.g., about 10 years old to about 19 years old), or adult (e.g., older than about 19 years old).

B. Drugs for Mitochondrial Diseases

In one aspect, the drugs provided herein protect or prevent a subject from the onset of mitochondrial disease. The drug may suppress the disease in the subject. In some embodiments, the drug can prevent a subject from developing, exhibiting, or experiencing one or more symptoms of the disease. In some embodiments, the subject does not have a symptom or clinical feature of the disease. In one embodiment, the drug is administered to a subject who has not presented with a symptom of a mitochondrial disease. The drug can be prophylactically administered. The subject may be asymptomic prior receiving the drug. In some cases, the subject may have a likelihood of having the disease. For example, the subject may have a family history of a mitochondrial disease, and/or have a genetic mutation associated with a specific mitochondrial disease.

In another aspect, the drugs provided herein are used to treat a mitochondrial disease, ameliorate a mitochondrial disease, ameliorate or attenuate disease severity, and/or attenuate clinical progression of a mitochondrial disease. In some embodiments, any of the drugs provided herein can be used to treat, attenuate or ameliorate one or more symptoms of a mitochondrial disease.

In some embodiments, the drug stimulates or promotes mitochondrial ATP synthesis or production. The drug may reduce ATP hydrolysis and/or increase ATP synthesis on mitochondria. In some instances, the drug increases the rate of ATP synthesis.

In other embodiments, the drug inhibits the induction of one or more inflammatory or immune response gene. Non-limiting examples of such genes include Fas, Tlr4, Ccl5, Ccl2, C1ra, Tlr3, Mmp12, ICAM1, Cxcl9, Aif1, Tlr2, CD68, Ccl12, C1qc, B2M and Cxcl10. Administration of a drug provided herein may increase the expression level (e.g., RNA level or protein level) or activity of an inflammatory or immune response gene or gene product.

In some embodiments, a subject is administered papaverine, zolpidem, methoxamine, methenamine, methotrexate, azathioprine, fluorouracil, zidovudine, a pharmaceutically acceptable salt thereof, analog thereof, or derivative thereof. In other embodiments, a subject is administered papaverine, zolpidem, methoxamine, methenamine, methotrexate, azathioprine, fluorouracil, zidovudine, a pharmaceutically acceptable salt thereof, analog thereof, or derivative thereof in combination with rapamycin and/or idebenone, a pharmaceutically acceptable salt thereof, analog thereof, or derivative thereof.

In other embodiments, a subject is administered rapamycin, a pharmaceutically acceptable salt thereof, analog thereof, or derivative thereof. In yet other embodiments, a subject is administered rapamycin, a pharmaceutically acceptable salt thereof, analog thereof, or derivative thereof in combination with zolpidem, methoxamine, methenamine, methotrexate, azathioprine, fluorouracil, zidovudine, idebenone, a pharmaceutically acceptable salt thereof, analog thereof, or derivative thereof.

In some embodiments, the drug is papaverine, papaverine hydrochloride, papaverine codecaroxylate, papaverine adenylate, papaverine teprosylate, papaverine carbanion, or papaverine monopyridoxal phosphate. In other cases, the drug is papaverine or a pharmaceutically acceptable salt thereof including a hydrobromide salt, hydroiodide salt, methyliodide salt, acid sulphate salt, acid oxalate salt, succinate salt, salicylate salt, picrate salt, picrolonate salt, cromesilate salt, camsylate salt, nicotinate salt, phenyglycolate salt, and the like. A drug containing papaverine can contain up to about 5% or more by weight papaverine or papaverine salt. A drug containing papaverine can be administered as an oral dose of about 150 mg to about 300 mg. For injection administration, a dose of ranging from about 2.5 mg-120 mg can be provided to a subject. In some cases, papaverine is in a 30 mg/ml solution for injection.

In some embodiments, the drug is zolpidem or a pharmaceutically acceptable salt thereof including, but not limited to, zolpidem tartate, zolpidem hemitartate, zolpidem hydrogentartrate, zolpidem hydrochloride, zolpidem mesylate, zolpidem tosylate, and zolpidem sulfate. The zolpidem salt can be any described, for example, in U.S. Pat. Nos. 6,242,460 and 8,916,583. In some cases, the salt is selected from the group consisting of hydrochloride, hydrobromide, maleate, fumarate, tartrate, sulfate and sulfonates. A zolpidem drug can be in a solid form, an aqueous solution, or any form or composition described, for example, in U.S. Pat. Nos. 6,514,531; 7,632,517; 8,034,371; 8,148,393; 88,846,084; 8,916,583. The dose of zolpidem administered can range from about 1 mg to 10 mg or more, e.g., about 1 mg, 2 mg, 3 mg, 4 mg, 5 mg, 6 mg, 7 mg, 8 mg, 9 mg, 10 mg or more.

In some embodiments, the drug is methoxamine (2-amino-1-(2,5-dimethoxyphenyl)-1-propanol) or a pharmaceutically acceptable salt thereof including but not limited to methoxamine hydrochloride. In some cases, the pharmaceutically acceptable salts of methoxamine are formed with acids and quaternary ammonium derivatives. The acids may be inorganic acids such as hydrochloric acid, hydrobromic acid, sulfuric acid, nitric acid or phosphoric acid; as well as the salts formed with organic acids such as acetic acid, propionic acid, glycolic acid, lactic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and hydroxybenzenesulfonic acids. Methoxamine can be administered by injection such as intravenous injection and intramuscular injection. In some cases, methoxamine is administered as an inhalant as described in, for example, U.S. Pat. No. 5,116,878. The dose can range from about 1 mg to about 50 mg or more, e.g., 1 mg, 2 mg, 3 mg, 4 mg, 5 mg, 6 mg, 7 mg, 8 mg, 9 mg, 10 mg, 15 mg, 20 mg, 25 mg, 30 mg, 35 mg, 40 mg, 45 mg, 50 mg, or more.

In some embodiments, the drug is methenamine or a pharmaceutically acceptable salt thereof including, but not limited to, methenamine mandelate, methenamine undecylenate, methenamine hippurate and methenamine sulfosalicylate. Methenamine may be administered orally in, for example, a tablet, capsule, granules, powder, pellets, or suspension form, parenterally, or nonparenterally. In some cases, the drug is administered by injection, for example, intravenously or intramuscularly. The dose administered can range from about 0.5 g to about 2 g, e.g., 0.5 g, 1 g, 1.5 g or 2 g.

In some embodiments, the drug is rapamycin, a pharmaceutically acceptable salt thereof, e.g., rapamycin carbamate or an analog thereof. Useful rapamycin analogs include 17,18-dihydrorapamycin, 19,20-dihydrorapamycin, 17,18, 19,20-tetrahydrorapamycin, and others described in, e.g., U.S. Pat. No. 5,489,680 and International Patent Application Publication Nos. WO 1994/005300 and WO 2011/034816. Rapamycin can be administered orally, topically, transdermally, transmucosally or parenterally in a formulation as described in, for example, U.S. Pat. Nos. 5,145,684; 5,516, 770; 5,530,006; 5,989,591 and 5,985,325. Formulation of rapamycin and analogs thereof are set forth in, e.g., U.S. Patent Publication No. 20120022095, and U.S. Pat. Nos. 5,286,731 and 5,530,006. In some cases, rapamycin is produced by a method known in the art such as those described in International Patent Application Publication Nos. WO 2013/153554 and WO 2014/072984.

In other embodiments, the drug administered to a subject with a mitochondrial disease or at risk of having a mitochondrial disease is a nucleotide metabolism inhibitor, such as a purine metabolism inhibitor or a pyrimidine metabolism inhibitor. Non-limiting examples of a nucleotide metabolism inhibitor include azathioprine, fluorouracil, methotrexate, zidovudine, and those described in, e.g., U.S. Pat. Nos. 6,228,847; 6,492,347; and 7,109,331.

Azathioprine is a nucleoside analog reverse-transcriptase inhibitor. Azathioprine, analogs thereof, and derivative thereof may be administered orally, rectally, topically, transdermally, transmucosally or parenterally. Azathioprine compositions, analogs thereof, and derivatives thereof are disclosed in, e.g., U.S. Pat. Nos. 5,691,343; 5,733,915; 5,905, 081; 6,432,967; 7,323,471; and U.S. Patent Application Publication No. 20140371242. In some instances, the dose administered ranges from about 50 mg to about 500 mg or more, e.g., 50 mg, 100 mg, 150 mg, 200 mg, 250 mg, 300 mg, 350 mg, 400 mg, 450 mg, 500 mg, or more.

Fluorouracil or 5-fluorouracil is a pyrimidine analog that is useful to treat cancers, actinic keratosis, and Bowen's disease. Fluorouracil compositions, analogs thereof, and derivatives thereof are disclosed in, e.g., U.S. Pat. Nos. 3,971,784; 5,089,503 and 6,6670,335. The drug can be administered intravenously at a dose of up to about 1 g; topically in an about 0.5% to 5% cream or solution, or orally at a dose of about 1 mg/m$^2$.

Methotrexate is an antimetabolite and antifolate drug that has been used to treat Crohn's disease, rheumatoid arthritis, psoriasis, acute lymphoblastic, breast cancer, gestational trophoblastic disease, head and neck cancer, lung cancer, mycosis fungoides, non-Hodgkin lymphoma, and osteosarcoma. Pharmaceutically acceptable salts of the drug can be methotrexate sodium and methotrexate hydrate. Methotrexate compositions, analogs thereof, and derivatives thereof are disclosed in, e.g., U.S. Pat. Nos. 5,166,149; 5,382,582; and 6,485,740; and U.S. Application Publication Nos.

20050101605; 20080268045, 20100239646; 20120107246, and 20130178476. In some cases, the dose ranges from about 2.5 mg to about 25 mg, e.g., about 2.5 mg, about 5 mg, about 10 mg, about 15 mg, about 20 mg, about 25 mg or more. The drug can be administered intravenously or orally in a dose of about 100 mg to 600 mg.

Zidovudine is a dideoxynucleoside compound in which the 3'-hydroxy group on the sugar moiety has been replaced by an azido group. The compound acts as a nucleoside analog reverse transcriptase inhibitor. Pharmaceutically acceptable salts of zidovudine include zidovudine sodium salts, zidovudine monophosphate, zidovudine triphosphate, and the like. Zidovudine compositions, analogs thereof, and derivatives thereof are disclosed in, e.g., U.S. Pat. Nos. 4,780,453; 4,917,900; 4,983,586; and 4,983,586.

C. Pharmaceutical Compositions

In some aspects, the present invention provides a pharmaceutical composition, including an FDA-approved drug compound and a pharmaceutically acceptable excipient, for administration to a patient in need thereof.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. Topical preparations include those applied to the eye such as eye drops, the ear such as ear drops, and directly to the skin such as creams, foams, gels, lotions, ointments, powders, pastes, tinctures, and transdermal patches. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of the present invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and either a drug compound of the present invention, or a pharmaceutically acceptable salt of a drug compound disclosed herein.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa., 1990.

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% or 10% to 70% of the active compound.

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of a ligand of the present invention or a combination thereof, with the remainder consisting of suitable pharmaceutical carrier and/or excipients. Appropriate excipients can be tailored to the particular composition and route of administration by methods well known in the art, e.g., *Remington's Pharmaceutical Sciences*, supra.

Suitable solid excipients include, but are not limited to, magnesium carbonate; magnesium stearate; calcium phosphate; calcium silicate; talc; pectin; dextran, dextrin, and cyclodextrin inclusion complexes; a low melting wax; cocoa butter; carbohydrates; sugars including, but not limited to, lactose, dextrose, sucrose, mannitol, or sorbitol; starches including, but not limited to, starch from corn, wheat, rice, potato, or other plants; cellulose such as methyl cellulose, hydroxypropylmethyl-cellulose, or sodium carboxymethyl-cellulose; and gums including arabic, tragacanth, and acacia; as well as proteins including, but not limited to, gelatin, collagen; microcrystalline cellulose, water, saline, syrup, ethylcellulose, and polyacrylic acids such as Carbopols, e.g., Carbopol 941, Carbopol 980, Carbopol 981, etc.; lubricating agents; mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents; biodegradable polymer beads. If desired, disintegrating or solubilizing agents may be added, such as the cross-linked polyvinyl pyrrolidone, agar, alginic acid, alginates, or a salt thereof, such as sodium alginate.

A pharmaceutically acceptable carrier may include physiologically acceptable compounds that act, for example, to stabilize the compounds or modulate their absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the compounds of the present invention and on the particular physiochemical characteristics of the compounds of the present invention.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

D. Administration of Drugs

Administration of the compounds presented herein with a suitable pharmaceutical excipient as necessary can be carried out via any of the accepted modes of administration. Thus, administration can be, for example, oral, topical, ocular, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, or by inhalation. Suitable sites of administration include, but are not limited to, skin, muscle, gastrointestinal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

The pharmaceutical preparation is preferably in unit dosage form. The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of the drug compound. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Methods for preparing such dosage forms are known to those skilled in the art (see, for example, *Remington's Pharmaceutical Sciences*, 18TH ED., Mack Publishing Co., Easton, Pa. (1990)). The composition to be administered contains a quantity of the ligand or combination of ligands in a pharmaceutically effective amount for relief of a condition being treated (e.g. osteoporosis) when administered in accordance with the teachings of this invention. In addition, pharmaceutically acceptable salts of the ligands of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, 4$^{th}$ Ed. (New York: Wiley-Interscience, 1992).

For oral administration, the compositions can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the ligands or combination of ligands, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The ligands can also be formulated into a suppository disposed, for example, in a polyethylene glycol (PEG) carrier.

Liquid compositions can be prepared by dissolving or dispersing a ligand or a combination of ligands and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The ligands of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

The pharmaceutical compositions of the present invention can be prepared for administration by a variety of different routes. In general, the type of carrier is selected based on the mode of administration. Pharmaceutical compositions can be formulated for any appropriate manner of administration, including, for example, ocular, topical, oral, nasal, intrathecal, sublingual or parenteral administration, including subcutaneous, intravenous, and intramuscular injection or infusion. A pharmaceutical composition (e.g., for oral administration or delivery by injection) can be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

Some slow release embodiments include polymeric substances that are biodegradable and/or dissolve slowly. Such polymeric substances include polyvinylpyrrolidone, low and medium molecular weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi- and trisubstituted glycerides. Slow release agents may also be prepared as generally described in International Patent Application Publication No. WO 94/06416.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

E. Dosages

The compounds utilized in the methods of the present invention are effective over a wide dosage range for the treatment of a mitochondrial disease, for example, LHON. It is understood that the amount of the compound actually administered may be determined by a physician, in the light of the relevant circumstances including the choice of compound to be administered, the chosen route of administration, the age, weight, and response of the individual patient, and the severity of the patient's symptoms, and therefore the above dosage ranges are not intended to limit the scope of the invention in any way.

In some embodiments, the therapeutic dose administered to a subject in need thereof is effective in, for example, suppressing the progression of a mitochondrial disease;

suppressing mitochondrial defects in a tissue affected by disease; reducing or ameliorating one or more symptoms of disease; reducing the relapse rate or rate of disease progression; reducing or inhibiting the induction of one or more inflammatory genes; or stimulating or increasing mitochondrial ATP synthesis.

For the compounds provided herein, a therapeutically effective amount or dose can be estimated initially from activity assays in animals including animal models of specific mitochondrial diseases (e.g., Ndufs4 knockout mice). The Ndufs4 knockout mouse model is a model of Leigh syndrome (Johnson et al., *Science*, 2013, 342: 1524) and human Leber's hereditary optic neuropathy (LHON; Yu et al., *Human Molecular Genetics*, 2015, 24(10): 2848-2860). Both these mitochondrial diseases involve a mitochondrial complex I deficiency. In some instances, a dose can be formulated in animal models to achieve a circulating concentration range that includes the $IC_{50}$ as determined by activity assays. Such information can be used to more accurately determine useful doses in humans.

Toxicity and therapeutic efficacy of the compounds described herein can be determined by standard pharmaceutical procedures in experimental animals, e.g., by determining the $IC_{50}$ and the $LD_{50}$ (lethal dose causing death in 50% of the tested animals) for a subject compound. The data obtained from these activity assays and animal studies can be used in formulating a range of dosage for use in human.

The dosage may vary depending upon the dosage form employed and the route of administration utilized. The exact formulation, route of administration and dosage can be chosen by the individual physician in view of the patient's condition. Dosage amount and interval may be adjusted individually to provide plasma levels of the active moiety which are sufficient to maintain the modulating effects. The minimal effective concentration of the compound will vary for each preparation, but can be estimated from in vitro data. Dosages necessary to achieve the minimal effective concentration will depend on individual characteristics and route of administration. HPLC assays or bioassays can be used to determine plasma concentrations of the compounds described herein.

In some instances, dosage intervals can be determined using the minimal effective concentration value. Preparations should be administered using a regimen, which maintains plasma levels above the minimal effective concentration for 10-90% of the time, e.g., between 30-90% or 50-90% of the time.

In some embodiments, a unit dosage form comprises about 0.5 to about 2000 mg, about 0.5 to about 1000 mg, about 0.5 to about 500 mg, about 0.5 to about 300 mg, about 0.5 to about 200 mg, about 0.5 to about 100 mg, about 0.5 to about 90 mg, about 0.5 to about 85 mg, about 0.5 to about 80 mg, about 0.5 to about 75 mg, about 0.5 to about 70 mg, about 5 to about 100 mg, about 25 to about 100 mg, or about 75 to about 100 mg.

In some embodiments, a unit dosage form comprises about 0.5 mg/day to about 2000 mg/day, about 0.5 mg/day to about 1500 mg/day, about 0.5 mg/day to about 1000 mg/day, about 0.5 mg/day to about 900 mg/day, about 0.5 mg/day to about 800 mg/day, about 0.5 mg/day to about 700 mg/day, about 0.5 mg/day to about 600 mg/day, about 0.5 mg/day to about 500 mg/day, about 0.5 mg/day to about 400 mg/day, about 0.5 mg/day to about 300 mg/day, about 0.5 mg/day to about 200 mg/day, about 0.5 mg/day to about 100 mg/day, about 0.5 mg/day to about 90 mg/day, about 0.5 mg/day to about 80 mg/day, about 0.5 mg/day to about 70 mg/day, about 0.5 mg/day to about 60 mg/day, about 0.5 mg/day to about 50 mg/day, about 0.5 mg/day to about 40 mg/day, about 0.5 mg/day to about 30 mg/day, about 0.5 mg/day to about 20 mg/day, or about 0.5 mg/day to about 10 mg/day.

In other embodiments, a unit dosage form comprises about 0.5 mg/day to about 500 mg/day, about 0.5 mg/day to about 200 mg/day, about 0.5 mg/day to about 100 mg/day, about 1 mg/day to about 100 mg/day, about 1 mg/day to about 85 mg/day, about 1 mg/day to about 75 mg/day, about 1.5 mg/day to about 100 mg/day, about 1.5 mg/day to about 90 mg/day, about 1.5 mg/day to about 85 mg/day, about 1.5 mg/day to about 75 mg/day, about 1.5 mg/day to about 70 mg/day, about 5 mg/day to about 100 mg/day, about 5 mg/day to about 85 mg/day, about 5 mg/day to about 75 mg/day, about 10 mg/day to about 100 mg/day, about 10 mg/day to about 90 mg/day, about 10 mg/day to about 85 mg/day, about 10 mg/day to about 75 mg/day, about 10 mg/day to about 70 mg/day, about 25 mg/day to about 100 mg/day, about 25 mg/day to about 85 mg/day, about 25 mg/day to about 75 mg/day, about 50 mg/day to about 100 mg/day, about 50 mg/day to about 90 mg/day, about 50 mg/day to about 85 mg/day, about 50 mg/day to about 75 mg/day, about 50 mg/day to about 70 mg/day, about 70 mg/day to about 100 mg/day, about 70 mg/day to about 90 mg/day, about 70 mg/day to about 85 mg/day, or about 65 mg/day to about 90 mg/day. Daily dosages may be achieved by once a day, twice a day or three times or more daily administration, preferably once a day administration.

In some embodiments, an effective dosage may be in the range of about 0.01 to about 25 mg/kg body weight, in particular, about 0.01 to about 25 mg/kg body weight, about 0.01 to about 20 mg/kg body weight, about 0.01 to about 15 mg/kg body weight, about 0.01 to about 10 mg/kg body weight, about 0.01 to about 5 mg/kg body weight, about 0.2 to about 5 mg/kg body weight, or about 0.1 to about 2.0 mg/kg body weight, more particularly about 0.1 to about 1.5 mg/kg body weight, and most particularly about 0.5 to about 2 mg/kg body weight, about 0.5 to about 1.5 mg/kg body weight, about 1.0 to about 2.0 mg/kg body weight, about 1.0 to about 3.0 mg/kg body weight, about 1.0 to about 4.0 mg/kg body weight, about 1.0 to about 5.0 mg/kg body weight, about 1.0 to about 6.0 mg/kg body weight, about 1.0 to about 7.0 mg/kg body weight, about 1.0 to about 8.0 mg/kg body weight, about 1.0 to about 9.0 mg/kg body weight, about 1.0 to about 10.0 mg/kg body weight, about 1.0 to about 11.0 mg/kg body weight or about 1 to about 12.0 mg/kg body weight, about 1.0 to about 13.0 mg/kg body weight, about 1.0 to about 14.0 mg/kg body weight, about 1.0 to about 15.0 mg/kg body weight, about 1.0 to about 16.0 mg/kg body weight, about 1.0 to about 17.0 mg/kg body weight, about 1.0 to about 18.0 mg/kg body weight, about 1.0 to about 19.0 mg/kg body weight, about 1.0 to about 20.0 mg/kg body weight, about 1.0 to about 21.0 mg/kg body weight, about 1 to about 22.0 mg/kg body weight, about 1 to about 23.0 mg/kg body weight, about 1.0 to about 24.0 mg/kg body weight, or about 1.0 to about 25.0 mg/kg body weight.

The duration of treatment can be adapted to the conditions of the patient. A subject may be treated with a compound disclosed herein, composition, dosage form or formulation thereof on substantially any desired schedule. A compound disclosed herein, composition, dosage form or formulation may be administered one or more times per day, e.g., 1, 2, 3, 4, 5, or more times per day. In some embodiments, the compound is administered 1 or 2 times per day, once per week, once a month or continuously. However, a subject may be treated less frequently, such as every other day or once a week, or more frequently. A compound, composition, dosage form or formulation provided herein may be administered to a subject for about or at least about 2 days, 3 days, 4 days, 5 days, 1 week, 2 weeks to 4 weeks, 1 week to 10 weeks, 1 week to 20 weeks, 1 week to 24 weeks, 1 week to 48 weeks, 2 weeks to 6 weeks, 2 weeks to 8 weeks, 2 weeks to 10 weeks, 2 weeks to 12 weeks, 2 weeks to 14 weeks, 2 weeks to 15 weeks, 2 weeks to 16 weeks, 2 weeks to 20 weeks, 2 weeks to 24 weeks, 2 weeks to 48 weeks, 2 weeks to 18 months, or 2 weeks to 24 months periodically, consecutively or continuously. The duration of treatment may be periodically or continuously over the course of the patient's disease.

IV. Examples

The following examples are offered to illustrate, but not to limit, the claimed invention.

Example 1: Mitochondrial Complex I Deficiency Leads to Inflammation and Retinal Ganglion Cell Death in the Ndufs4 Mouse This example illustrates the use of rapamycin to treat a mitochondrial disease such as a mitochondrial complex I deficiency. The example also shows that rapamycin suppresses inflammation in an animal model of mitochondrial complex I deficiency.

Abstract

Mitochondrial complex I (NADH dehydrogenase) is a major contributor to neuronal energetics, and mutations in complex I lead to vision loss. Functional, neuroanatomical and transcriptional consequences of complex I deficiency were investigated in retinas of the Ndufs4 knockout mouse. Whole eye ERGs and multielectrode arrays confirmed a major retinal ganglion cell functional loss at P32, and retinal ganglion cells loss at P42. RNAseq demonstrated a mild and then sharp increase in innate immune and inflammatory retinal transcripts at P22 and P33 respectively, which were confirmed with qRT-PCR. Intraperitoneal injection of the inflammogen lipopolysaccharide further reduced retinal ganglion cell function in Ndufs4 KO, supporting the connection between inflammatory activation and functional loss. Complex I deficiency in the retina clearly caused innate immune and inflammatory markers to increase coincident with loss of vision, and RGC functional loss. How complex I incites inflammation and functional loss is not clear, but could be the result of misfolded complex I generating a "non-self" response, and induction of innate immune response transcripts was observed before functional loss at P22, including beta-2 microglobulin and Cx3cr1, and during vision loss at P31 (B2m, Tlr2, 3, 4, C1qa, Cx3cr1 and Fas). These data support the hypothesis that mitochondrial complex I dysfunction in the retina triggers an innate immune and inflammatory response that results in loss of retinal ganglion cell function and death, and suggests novel therapeutic routes to counter mitochondrial defects that contribute to vision loss.

Introduction

Mitochondrial diseases are typically characterized by decreased energy production due to defects in the oxidative phosphorylation (OXPHOS) system. In humans, the most frequent deficiency is in complex I (1). Mitochondrial complex I activity is essential for neuronal homeostasis, and deficiency of complex I causes neurotoxicity. The most common symptoms linked to complex I deficiency include mental and motor retardation, blindness, heart rhythm disturbances, heart failure, exercise intolerance, and hypotonia—clinically presenting as Leigh syndrome (Koene et al., J. Inherit. Metab. Dis., 34, 2011, 293-307).

All mitochondrial complexes (except complex II) are under dual genetic control (mitochondrial and nuclear DNA), in which a mutation in either causes mitochondrial dysfunction (Koene et al., J. Inherit. Metab. Dis., 34, 2011, 293-307). Mitochondrial complex I is by far the most complicated complex of the OXPHOS system. It is comprised of 45 subunits, 38 of which are encoded by nuclear DNA and 7 are encoded by mitochondrial DNA (Tucker et al., IUBMB Life, 2011, 63, 669-677). Human genetic optic neuropathies such as, Leber's hereditary optic neuropathy has been linked to mtDNA point mutations at positions 11778/ND4, 3460/ND1, and 14484/ND6, which affect complex I and leads to a loss of retinal ganglion cells (RGCs) and degeneration of the optic nerve (Carelli et al., Neurochem. Int., 2002, 40, 573-584).

Other genetic mitochondrial defects that indirectly affect complex I is seen in autosomal dominant optic atrophy (DOA), which is caused by a mutation in the OPA1 gene that leads to a reduced rate of mitochondrial ATP synthesis at the level of complex I. The OPA1 gene also interacts with other mitochondrial proteins such as AIF. These interactions lead to apoptotic death of RGCs that further progresses to neurodegeneration and optic atrophy (Zanna et al., Brain, 2008, 131, 352-367).

Rotenone, a known inhibitor of complex I, has been shown to induce neurotoxicity of rat brain areas through astroglial activation and apoptosis (Swarnkar et al., Neurosci., 2013, 230, 172-183), and rotenone administered intravitreally causes RGC loss (Heitz et al., PLOS ONE, 2012, 7, e45182). In another study, subcutaneous injection of rotenone in rats caused a loss of photoreceptors in the outer retina and reduced synaptic connectivity between the remaining photoreceptors and their postsynaptic neurons (Esteve-Rudd et al., Neurobio. of Dis., 2011, 44, 102-115).

These genetic and toxicity studies taken together clearly implicate the role of mitochondrial complex I in visual function. The precise mechanism for how complex I causes neuronal death is not known, however bioenergetic, excitotoxic, and apoptotic mechanisms have been proposed (Koene et al., J. Inherit. Metab. Dis., 34, 2011, 293-307; Carelli et al., Neurochem. Int., 2002, 40, 573-584). We have investigated the consequences of severe complex I deficiency in the retina, using the Ndufs4 KO mice originally developed as a model of Leigh syndrome, an encephalomyelopathic disease resulting from complex I defects in the brain that results in infantile death. This mouse model presents with a loss of vision at postnatal 30 days (P30), relating complex I deficiency to visual function (Kruse et al., Cell Metab., 2008, 7, 312-320). However, the cellular and molecular underpinnings of this complex I dependent visual defect have not been identified.

Our goal for this study was to investigate the functional and neuroanatomical defects in retinas with complex I deficiency. A second goal of this study was to investigate the molecular differences in the retina between knockout and wild type mice, to better understand how complex I deficiency could cause blindness. To accomplish this we examined Ndufs4 mice before, during, and after the onset of pathogenesis. We compared retinas of Ndufs4 KO mice and wild type mice, and showed that the period of visual impairment is accompanied by a prominent innate immune and inflammatory response in the Ndufs4 KO retina that can be further enhanced by lipopolysaccharide (LPS) injection. Thus, complex I deficiency in the retina leads to increase in inflammatory signals and retinal ganglion cell functional decrements and death in the Ndufs4 KO mouse.

Results

Figure 1B:
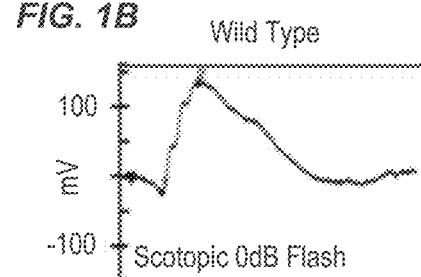
Figure 1C:
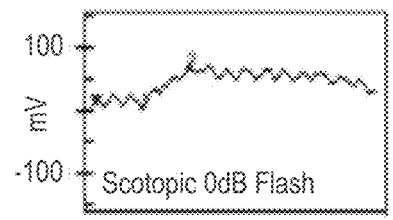

Complex I Defects Result in Decreased Retinal Ganglion Cell Function in Ndufs4 KO Mice Microelectrode Arrays (MEA) specifically measures the physiologic activity of RGCs in living tissue. MEAs were conducted on Ndufs4 KO and wild-type littermate controls; at P16 (P=0.3408) and P25 (P=0.1750) no significant functional defects were observed in RGCs when comparing Ndufs4 KO to wild type (FIG. 1A). By contrast, at P32 (P=0.0325), P35 (P=0.0445), P37 (P=0.0009), and P45 (P=0.0256) there was a significant decrease in RGC firing frequency when comparing Ndufs4 KO to wild type. Retinal mitochondrial activity was measured by Seahorse; Ndufs4 mice had a significant deficit in glutamate/malate driven mitochondrial oxygen consumption (data not shown). These data indicate that complex I defects in the KO mice specifically decrease RGC function. In order to measure overall retinal function in vivo, we also performed ERGs on P34 Ndufs4 KO mice. ERG testing of three Ndufs4 KO mice and three wild type mice showed that all KO mice had a decreased and sometimes absent b-wave at the brightest light stimulus (0 dB) indicating a markedly reduced retinal response to light stimulus (FIGS. 1B and 1C).

Complex I Deficiency Results in Cell Loss in the RGC Layer after 30 Days

To determine if loss of Ndufs4 affected RGC number we performed counts on DAPI-labelled cells within the RGC layer (FIGS. 2A-2F). Compared to wild type littermates Ndufs4 KO mice had significantly reduced numbers of cells in the RGC layer at P31 and P42 (FIG. 2E). Decrease in RGC number was greater at P42 compared to P31. No difference in number of DAPI-labelled cells was observed at P24 suggesting there was a progressive decline over time (FIG. 2E). Because DAPI labels all cells, we performed a similar analysis on cells immunolabeled for the POU domain, class 4, transcription factor 1 (Pou4f1 or Brn3a), which is enriched in a subset of RGCs (Xiang et al., *J. Neurosci.*, 1995, 15, 4762-4785; Quina et al., *J. Neurosci.*, 2005, 25, 11595-11604). There was a significant reduction in number of Brn3a-positive cells at P42 in Ndufs4 KO compared to wild type littermates (FIG. 2F). In contrast to the loss of DAPI-positive cells in the RGC layer, no differences in Brn3a cell number was observed at P16 or P31. Thus, in addition to the early loss of RGC function shown above at P32, there is a clear loss of RGCs in this complex I deficient mouse model at P42, consistent with pathological changes seen in multiple complex I deficient diseases that involve vision loss.

RNAseq Indicates an Increased Inflammatory Response

Figure 3:
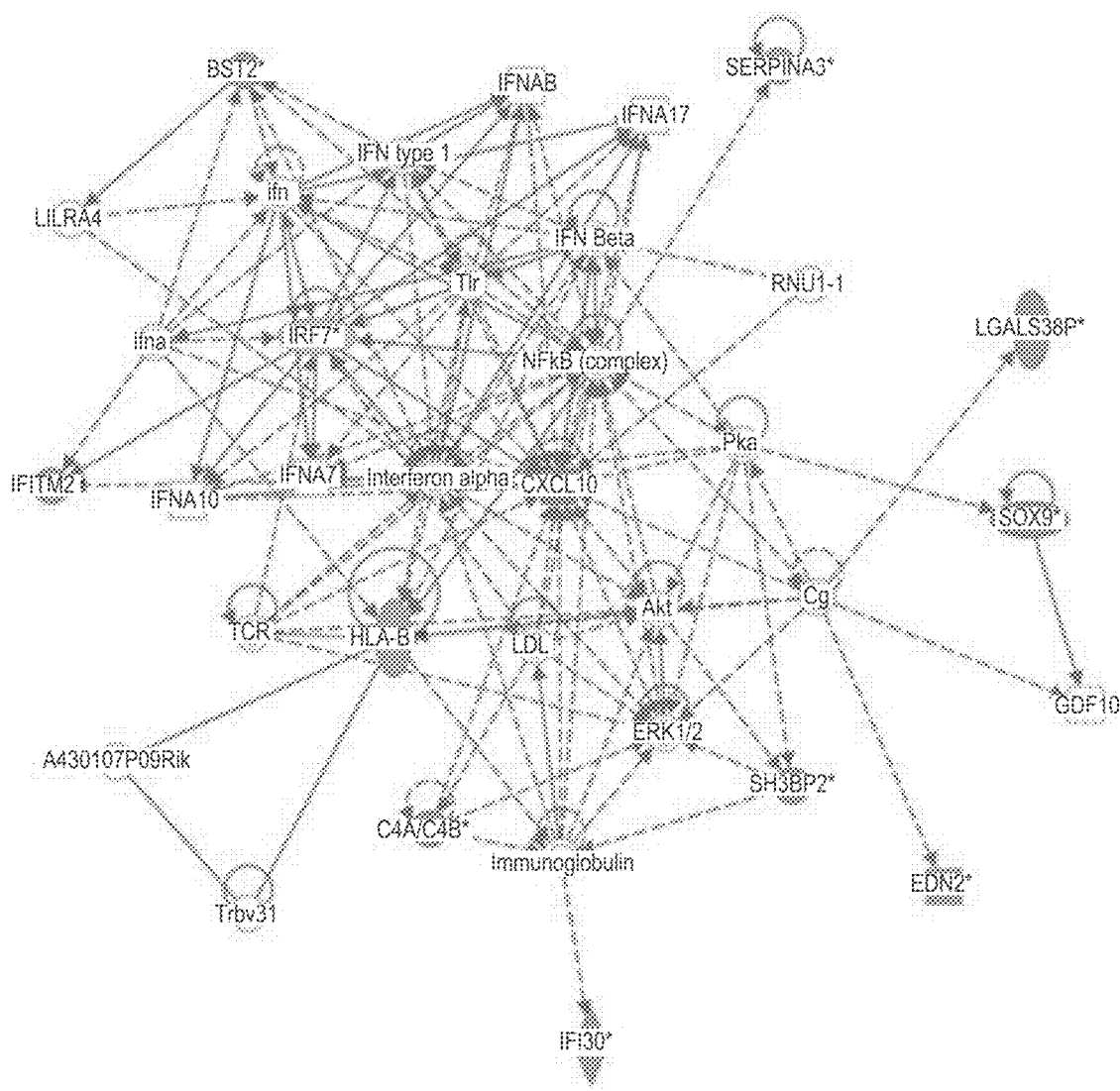
FIG. 3 provides Ingenuity pathway analysis of significantly upregulated genes that appeared in RNAseq analysis of both P33 Ndufs4 mice that underwent ERG and Ndufs4 mice that received no treatment.

To gain insight into pathomechanism of RGC functional and cellular loss in Ndufs4 KO mice, we analyzed global gene expression in retina by RNAseq at P22 (data not shown) and P33 respectively. At P22 only a handful of significant genes showed differences, including Gfap and Nes, which are associated with activation of astrocytes. By contrast, at P33 several hundred genes were significantly induced, and innate immunity and inflammation genes were dominant. For example, in Table 1 (RNAseq of P33 KOs vs. wild types) the top five out of five most significant KEGG pathways were all related to inflammation/immunity. Similarly, in P33 retinas from KO vs. wild type mice that had been subjected to ERG, nine out of 13 of the most significantly induced pathways are inflammatory/immune pathways, and the response is even stronger, presumably because the ERG procedure induced a stronger response (Table 1). In addition, ingenuity pathway analysis provided support for a network of inflammatory/immune genes centered on Cxcl10 (FIG. 3). Thus, complex I deficiency in the retina induces immune and inflammatory transcripts that are further aggravated by the somewhat invasive technique of ERG.

Figure 4:
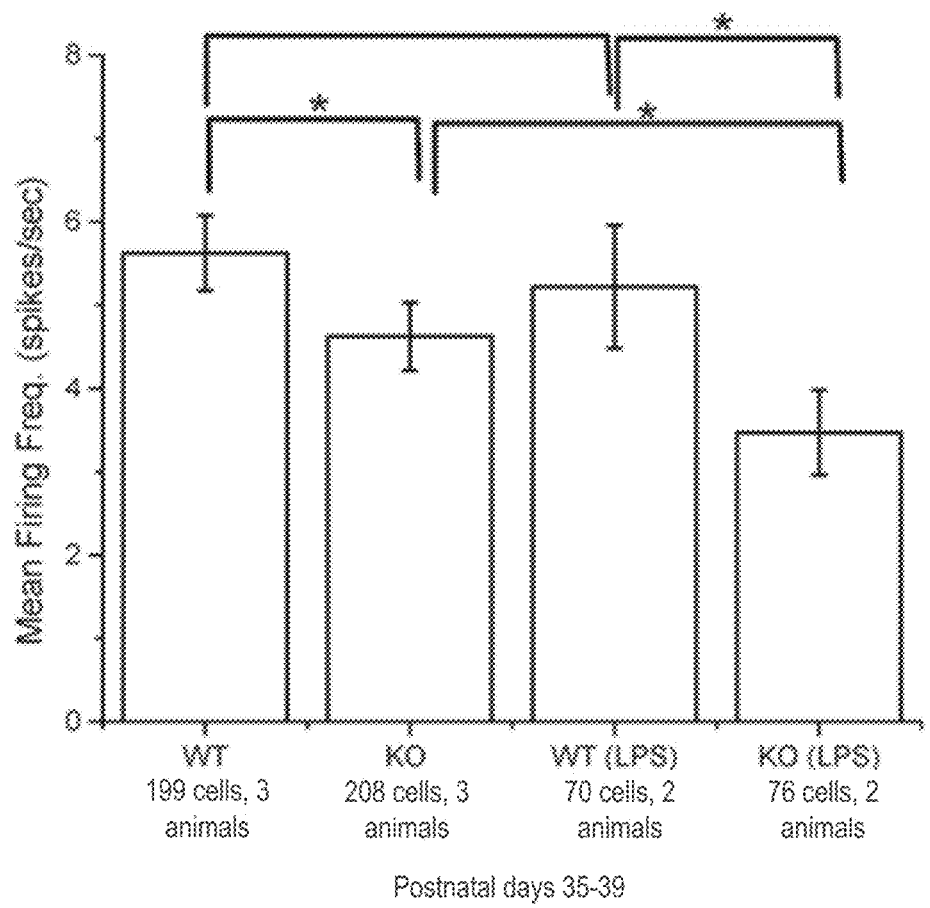
FIG. 4 illustrates a MEA recording of Ndufs4 KO and wild type mice with and without LPS treatment. Statistical significance determined by Kruskal-Wallis ANOVA test. * $P<0.05$.

Experimentally-Induced Inflammation Further Decreases RGC Function in Mutant Mice If increased inflammatory activity observed by RNAseq was the basis for decreased visual function observed by MEA, a further aggravation of inflammatory activity would be predicted to further decrease RGC function. LPS is a commonly used inflammogen known to induce microglial activation (Qin et al., *GLIA*, 2005, 52, 78-84). Ndufs4 KO mice were treated with a 0.5 mg/kg intraperitoneal injection of LPS, and RGC function was measured by MEA the next day. MEA recordings demonstrated that LPS-treated mutants had worse RGC function than LPS-treated wild type animals (P=0.0399) as well as mutant animals not exposed to LPS (P=0.0497), consistent with the idea that complex I defects induces inflammation which is responsible for RGC functional deficits (FIG. 4).

Figure 5A:
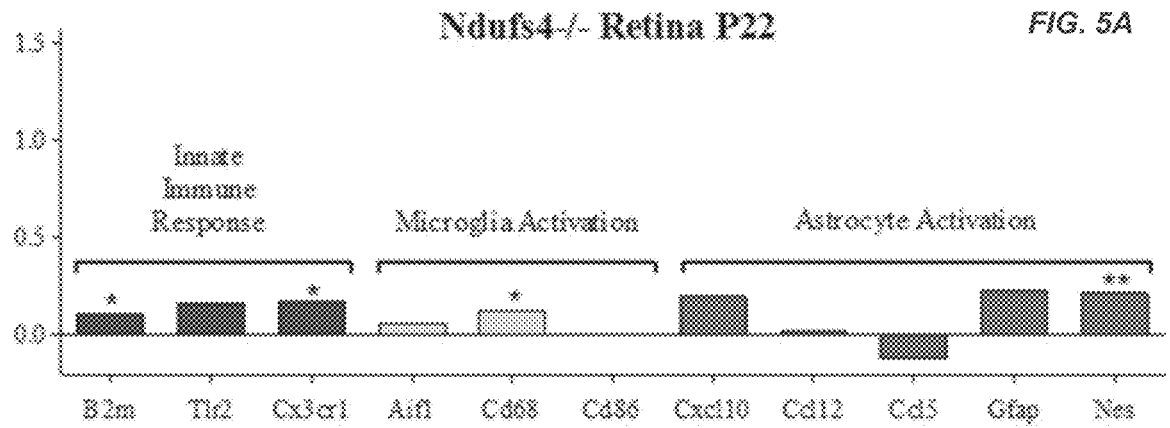
FIGS. 5A-5C show qRT-PCR data. The qRT-PCR results of Ndufs4 KO retina at P22 suggests early onset of microglia activation, astrocyte activation, and cell-mediated immune response genes (FIG. 5A). The data from Ndufs4 KO retinas at P31 suggest further increased genetic markers for microglia and astrocyte activation (FIG. 5B) along with an increase in cell mediated immune response genes (FIG. 5C). Statistical significance determined by student's t-test. * $P<0.05$,  $P<0.01$ * $P<0.001$, **** $P<0.0001$.
Figure 5B:
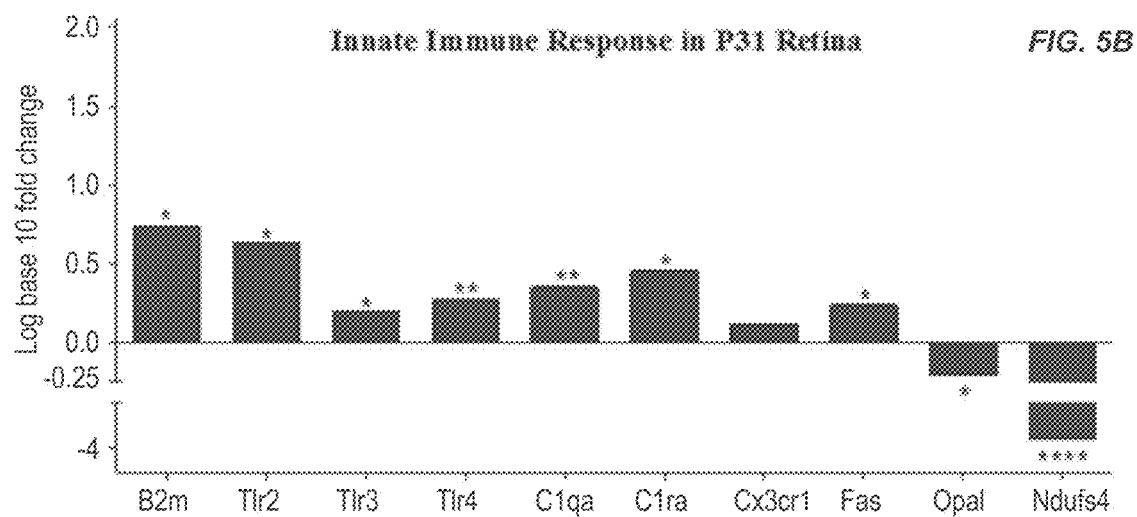
Figure 5C:
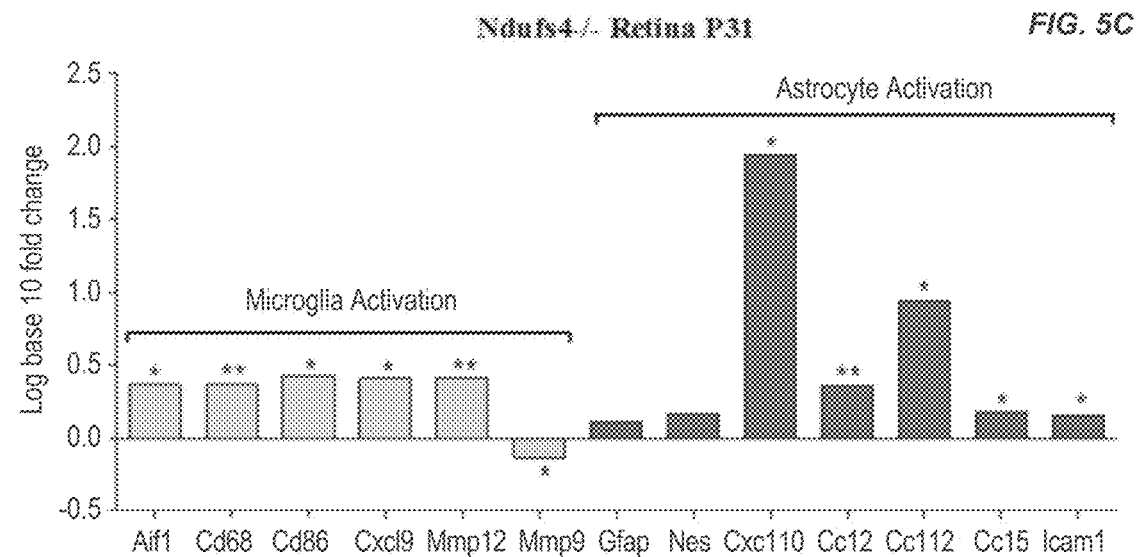

Induction of Innate Immunity, Microglial and Astroglial Markers Precedes Visual Loss in Ndufs4 Mice Since significant functional loss occurs between P20 and P30, these time points were investigated in more detail with respect to the prominent immune markers by qRT-PCR (FIGS. 5A-5C). As seen in the RNAseq data, there were very few significant differences between KO and wild type animals at P22 (FIG. 5A). However, increases in expression of genes associated with innate immunity (B2M; P=0.0220 and Cx3cr1; P=0.0334), microglial activation (Cd68; P=0.0198), and astroglial activation (Nes; P=0.0011) were observed (FIG. 5A). Thus, small increases in innate immunity, microglial and astroglial markers precede visual functional loss.

Strong Induction of Innate Immunity Genes, as Well as Microglial and Astroglial Markers Coincides with Visual Functional Loss in Ndufs4 Mice When retinas from P33 were examined, i.e., the time of visual functional loss, a much more robust set of gene expression changes associated with innate immunity, microglial and astroglial activation was observed between Ndufs4 KO and littermate wild type controls (FIG. 5B). The innate immunity markers induced were B2m (fold change=5.48, P=0.0091), Tlr2 (fold change=4.36, P=0.0037), Tlr3 (P=0.0161), C1qa (P=0.0077), C1ra (P=0.0431), Cx3cr1 (P=0.1433), and Fas (P=0.0426).

In terms of astroglial markers at P33, the chemokines, Cxcl10 (fold change=87.02; P=0.0055), Ccl2 (P=0.0023) and Ccl5 (P=0.0487) are significantly overexpressed and are associated with activated astrocytes, suggesting that the complex I-dependent immune response involves astrogliosis (Oh et al., *Neurovirol.*, 1999, 5, 82-94). Induction of the adhesion molecule, Icam1 (P=0.0266), is also consistent with activation of astrocytes (Oh et al., *Neurovirol.*, 1999, 5, 82-9).

Increases in microglial markers at P33 included Cd68 (P=0.0028), Cd86 (P=0.0179), Aif1 (P=0.0498), and Mmp12 (P=0.0044), observed along with a significant decrease in Mmp9 (P=0.0338) (FIG. 5B).

Rapamycin Inhibits Induction of Inflammatory Genes

Figure 6:
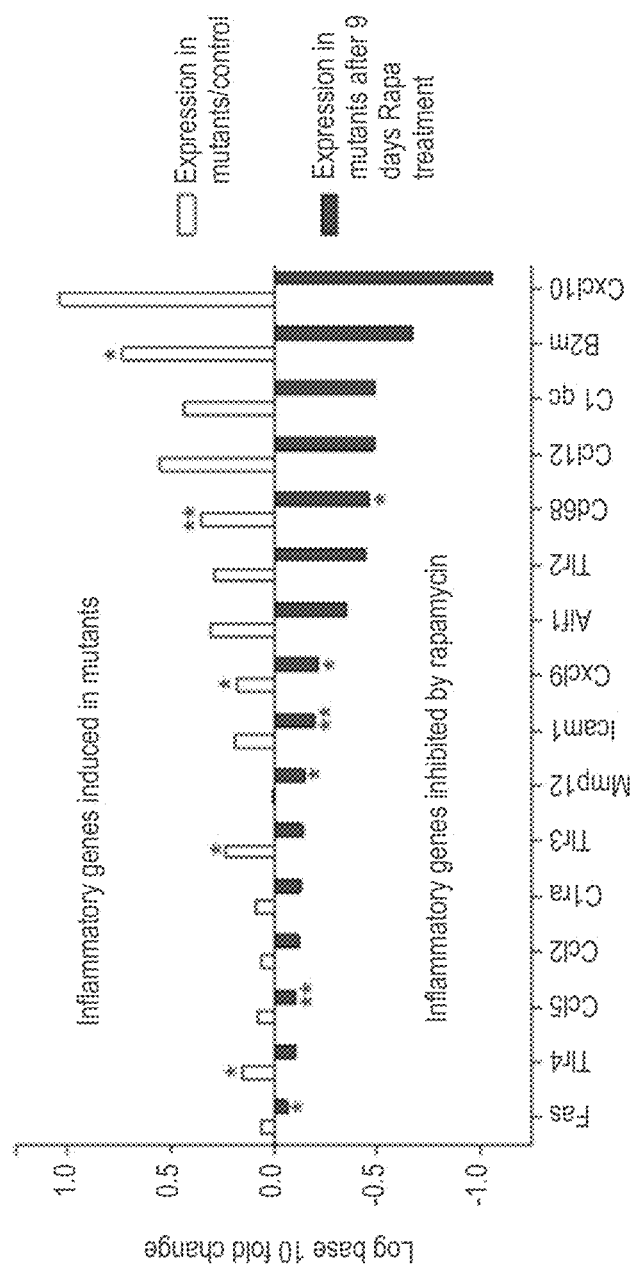
FIG. 6 depicts an experimental reversal of inflammatory gene induction by rapamycin. White bars, a mean increase in transcript level of 16/16 inflammatory markers was observed by qRT-PCR in retinas of Ndufs4 KO mice compared to wild type. Black bars, a uniform inhibition of mean amplitude of induction of inflammatory genes was observed in 16/16 transcripts in retinas of mice dosed intraperitoneally with rapamycin (8 mg/kg) for 9 days compared to vehicle injected Ndufs4 KO mice. Statistical significance determined by student's t test. * $P<0.05$, ** $P<0.01$.

In the rapamycin treatment experiment, the Ndufs4 KO mice showed elevated inflammatory markers compared to wild type control as expected. After nine days of rapamycin treatment Ndufs4 KO mice exhibited an inhibition of inflammatory gene induction with gene expression levels similar to wild type levels (FIG. 6). These data suggest that complex I deficiency triggers the inflammatory response, that is repressible by a known immunosuppressant that has been shown to extend lifespan in this Ndufs4 KO model.

Confirmation of Inflammatory Response at the Protein Level

Immunofluorescent staining and western blot of Ndufs4 KO and wild type retinas at P25-P30 provide supporting evidence for: activation of astrocytes through Cxcl10 and Gfap expression (FIGS. 7B, 7E, and 7H); microgliosis through Cd68 (FIG. 7D) and Iba1 (FIG. 7E) expression; along with innate immune and inflammatory proteins, such as B2m (FIG. 7F) and phosphorylated NF-kB (FIGS. 7C and 7G), respectively. This lends further support to the idea that astrocytes and microglia are activated in the retinal ganglion cell layer at the time of reduced retinal function and RGC loss.

Confirmation of Microglia Activation by Immunofluorescent Staining in KO Mice at Time of Vision Loss The microglial activation suggested by increased Aif1 and Cd68 gene expression at P33 was assessed at the cellular level by immunofluorescent labeling of allograft inflammatory factor 1 (Aif1; or Iba1)(FIGS. 9A-I), which is specifically localized in microglia throughout the brain and in retina. At P24, prior to onset of functional and cellular changes within the RGC layer we found no difference between wild type and Ndufs4 KO mice in the number of Iba1 positive cells in any of the retinal sublamina (FIGS. 9A-9C). Roughly equal numbers of cells were observed in all layers. At P31, however, the number of Iba1 positive cells was significantly increased within the inner nuclear layer (INL) of Ndufs4 KO animals (FIGS. 9D-9F). An increase in Iba1-positive cells was also observed at P42, but not within the INL. Instead, Iba1 was significantly upregulated in the inner plexiform layer (IPL) and the ganglion cell layer (GCL) (FIGS. 9G-9I). The progressive nature of increased Iba1 positive cells from the INL to the IPL and RGC layer over time suggests there could be a migration of microglia from outer to inner retina. Indeed we observed Iba1 positive cells at P31 that seemed to have neurites branching across the INL in a potential migratory pattern (FIG. 9E, arrow). Additionally, at P42, Iba1 positive cells were observed to be colabelled with ChAT, a specific marker of SBACs (FIG. 9H, arrow) suggesting they were enveloping starburst amacrine cells. Taken together, the rise of Iba1 expression in Ndufs4 retinas is consistent with an inflammatory response initiated by damaged SBACs resulting in the migration of Iba1-positive activated microglia that remove dying/dead amacrine cells.

Starburst Amacrine Cell Death Also Occurs as Early as 24 Days in KO Mice

As noted above there was a significant loss of cells in the RGC layer determined by DAPI staining that preceded cell loss measured with the more specific RGC associated factor Brn3a (FIGS. 2A-2F). This suggests another cell type within the RGC layer that may be more vulnerable to complex I deficiency, the loss of which may induce microglial and astroglial activation and inflammation. After RGCs, displaced amacrine cells are the second most numerous cell type within the RGC layer (Jeon et al., *J. Neurosci.*, 1998, 18, 8936-8946). To address potential loss of amacrine cells we examined immunoreactivity for ChAT, which is critical for synthesis of the transmitter acetylcholine and expressed exclusively by starburst amacrine cells (SBACs) (FIGS. 8A and 8B). The number of SBACs stained by anti-ChAT antibody in the ON layer (RGC layer) was significantly decreased at P24, P31, and P42 in the Ndufs4 KO retina (FIG. 8C). In contrast SBACs in the OFF layer (Inner nuclear layer) only showed a significant decrease in the P24 Ndufs4 KO retina (FIG. 8D). To determine whether this reduction in cell number was specific to SBACs we examined immunoreactivity for Gad67, a general marker for all GABA-ergic amacrine cells of which SBACs are a subset (Voinescu et al., *J. Comp. Neurol.*, 2009, 517, 737-750) (FIGS. 8E-8H). A significant loss of Gad67 staining was observed in Ndufs4 retinas, but only at P42, (FIG. 8I). These data suggest that starburst amacrine cells are also sensitive to complex I depletion.

Discussion

Ndufs4 KOs as a Model of Mitochondrial Complex I Deficiency in the Retina

We observed that complex I deficiency in the Ndufs4 mouse induces decreased visual function by ERG and MEA functional tests, and analyzed transcriptomics, protein expression, and neuroanatomy to clarify the mechanism of visual loss. We clearly observe specific RGC functional defects at P32 by MEA, cell loss in the ganglion cell layer at P31, and Brn3a-specific RGC cell loss at P42. These functional defects are preceded by an early (P21) increase in innate immunity, microglial, and astroglial transcripts, which expands to a major increase in these transcripts and protein at P32, the time of visual functional loss. Further incitement of inflammation with LPS produces further decrement of RGC function, as measured by MEA, suggesting that an immune/inflammatory response is critical in the pathomechanism connecting complex I deficiency to vision loss.

Chemokine Expression and Astrogliosis

Chemokines mediate the recruitment and activation of leukocytes and other cells to the site of inflammation during an immune response. The chemokines Cxcl10 and Ccl2 have been reported to be secreted by activated astrocytes (Oh et al., *Neurovirol.*, 1999, 5, 82-94; Bhowmick et al., *Neurosci. Letters*, 2006, 414, 45-50). Cxcl10 transcript was increased greater than 80-fold in Ndufs4 KO retina (FIG. 5C), and Cxcl10 protein expression strongly increased in the ganglion cells layer and inner nuclear layer (FIG. 7B). The increase in Icam1 is a further marker of astrogliosis, as well as the rise in astrocyte-specific GFAP (Oh et al., *Neurovirol.*, 1999, 5, 82-94). These data indicate that reactive astrocytes are playing a role in inflammation downstream of complex I deficiency.

Microglial Activation in Retinas of Ndufs4 KO Mice

Microglial activation is also apparent at P33 in KO retinas as seen from genetic increases in Aif1, Cd68, Cd86, Cxcl9, and Mmp12 expression (FIG. 5C). Immunohistochemical data also support an increase in Iba1 (FIG. 9D), which is the protein encoded by the gene Aif1, and Cd68, another marker of microglial activation (FIG. 7D). Over-activated microglia has been shown to have detrimental neurotoxic effects due to production of superoxide, nitric oxide, and tumor necrosis factor-$\alpha$ (TNF-$\alpha$), which suggests that microglia may have a causative role in neuroinflammation (Block et al., *Nat. Revs. Neurosci.*, 2007, 8, 57-69). LPS is only neurotoxic in the presence of microglia (Block et al., *Nat. Revs. Neurosci.*, 2007, 8, 57-69), thus the differentially larger defect in MEA in Ndufs4 KO mice (FIG. 4) further supports microglial involvement in their functional visual loss. Furthermore Tlr4 is the primary receptor for LPS (Qin et al., *GLIA*, 2005, 52, 78-84), and Tlr4 is overexpressed in Ndufs4 KO retinas at P31 (FIG. 5B).

Innate Immune Response

Further, we observe a strong induction of an innate immune response as seen with increases in transcripts of MHC Class 1 molecule B2m, as well as Tlr2, Tlr3, Tlr4, Icam-1 and Fas in the Ndufs4 KO retina. Binding of Fas ligand or TNF-$\alpha$ to Fas receptor leads to apoptosis. Fas ligand is expressed on activated T cells and natural killer cells and is mainly expressed in immune privileged sites, such as the eye (Brint et al., *Cell. Mol. Life Sci.,* 2013, 70, 4085-4099). The higher level of transcripts associated with innate immunity at P22 is consistent with the pathomechanism described in FIG. 10.

Potential Mechanisms for Complex I-Dependent Inflammation in Ndufs4 KO Mice

Figure 10:
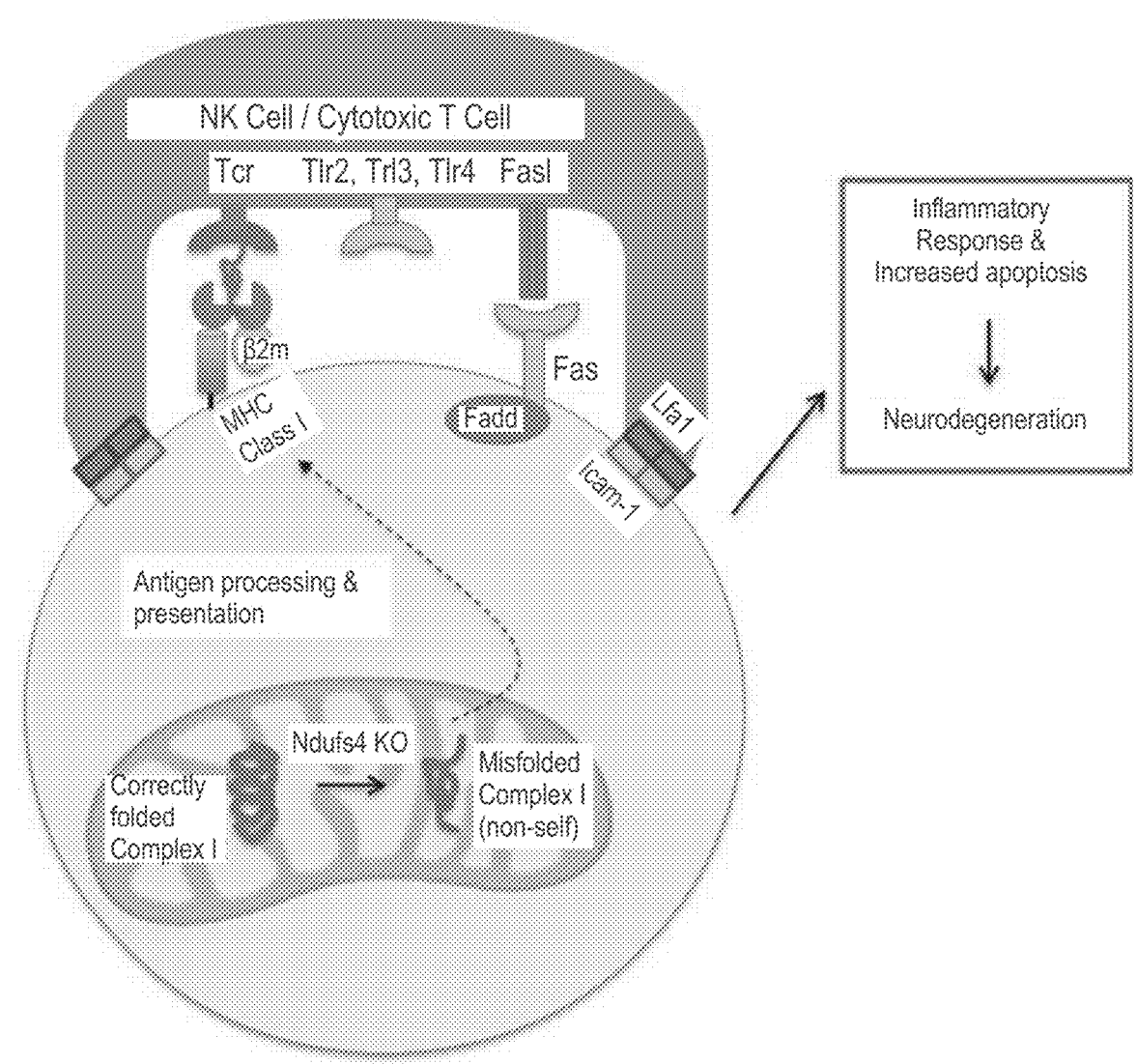
FIG. 10 depicts a schematic diagram of a potential mechanism of Ndufs4-mediated neurodegeneration. Ndufs4 deficiency causes misfolding of complex I, uncovering novel antigens, which are presented at an increased rate through the immune system through increased beta-2-microglobulin (b2m) expression, and the consequences of NK cell activation are further amplified through increased Fas receptor, Tlr2, Tlr3, and Tlr4 expression.

The finding of a massive increase in immune and inflammatory genes coincident with vision loss in KO mice suggests that inflammation is an intermediate between complex I deficiency and vision loss. But how complex I deficiency increases inflammation is less clear. One possible mechanism (Mechanism 1) is that loss of Ndufs4, a major assembly-factor protein for complex I (Calvaruso et al., *Hum. Mol. Genet.,* 2012, 21, 115-120), leads to misfolding and/or aggregation of complex I, which is recognized by the host as 'non-self', activating an inflammatory response (FIG. 10). The misfolded complex I protein is processed and presented as an antigen by MHC class I to MHC class I receptors on T lymphocytes or natural killer cells (Warren H S and Smyth M J, *Immunol. and Cell Biol.,* 1999, 77, 64-75.). Binding of MHC class I receptors would initiate pathways for apoptosis of the target cell and cytokine signaling to other cells.

Consistent with this mechanism 1 in the eye, Jin et al. (*Cell Metab.,* 2014, 20, 483-498) recently reported that complex I deficiency leads to a shift from fatty acid oxidation to glycolysis, which causes an induction of inflammation by the accumulation of fatty acids and lactate. They created a Ndufs4/TLR2/TLR4 triple KO mouse and found that TLR2/TLR4 deletion dampened palmitic acid-stimulated inflammatory gene expression and ROS production, implicating TLR2/TLR4 in complex I deficiency-mediated inflammation.

A second mechanism (Mechanism 2) is that complex I deficiency causes a severe bioenergetic defect selectively in the Starburst Amacrine Cells that start dying at P24 necrotically, inciting a microglial, astrocytic, and innate immune response activation, which further damages retinal ganglion cells. This second mechanism is also a completely novel explanation of complex I-dependent vision loss and RGC death.

Both mechanisms invoke a strong innate immune response as an intermediate between complex I deficiency and cell death. Thus, drugs known to block the innate immune response we expect to be protective. Recently, it was shown that the lifespan and neurological damage of Ndufs4 KO mice could be rescued by rapamycin, a potent MHC/innate immunity response immunosuppressant that is used in transplantation (Johnson et al., *Science,* 2013, 342, 1524-1528), without alteration of mitochondrial function. We find similarly that rapamycin uniformly suppresses the overexpression of every inflammatory gene elevated in Ndufs4 KO retina (FIG. 6). We interpret that rapamycin rescues from neurodegeneration because it suppresses inflammation that is downstream of the mitochondrial dysfunction and upstream of visual loss.

Summary

The Ndufs4 KO mouse is a reasonable model of complex I-dependent decline in RGC function and RGC death. Our data supports the mechanism of complex I deficiency to immune/inflammatory response to RGC functional defects and death. Both mechanisms provide novel insight into the pathophysiology of complex I deficient vision loss. The data suggests rational therapy, including rapamycin and other immunosuppressants in the context of mitochondrial blindness.

Materials and Methods

Animals

All experiments were performed in accordance with the National Institutes of Health and institutional guidelines regarding animal use and were approved by the Animal Care and Use Committee of the University of California, Davis (IACUC). Animals were housed in IACUC approved animal facilities under controlled environmental conditions. Ndufs4 KO mice were provided by Richard Palmiter (University of Washington, Seattle, USA). Phenotypically, these mice appear smaller than wild type and these mice were characterized as having visual deficits at P30 as measured by Morris water maze, visual cliff test, and visual placing (Quintana et al., *PNAS,* 2010, 107, 10996-11001). Mice were sacrificed at P16, P22, P24, P25, P31, P32, P33, P34, P35, P37, P42, and P45. Eighty-four mice were used in the current study; a detailed description of the number of KO and wild type mice, their age, and sex is provided below when describing each experiment. Detailed methods of tissue fixation or storage can be found in supplemental materials.

LPS Injection

Two Ndufs4 KO mice and two littermate wild type mice received intraperitoneal injection of LPS (0.5 mg/kg). As a comparison one Ndufs4 KO and one wild type mouse received intraperitoneal PBS injection as vehicle controls. Mice were within the age of P35-P39. The retinas were removed 12 hours after LPS injection and used for MEA as described below.

Electroretinogram

Eight P33 (four Ndufs4 KO and four littermate control with an equal distribution of male and female mice in each group) mice underwent ERG testing in both eyes (UTAS-EPIC XL; LKC Technologies, Gaitersburg, Md.). The mice were dark-adapted overnight and were anesthetized with Nembutal (50 mg/kg dose). The body temperature of the mice was maintained at 37° C. with a heating unit placed under the mouse. Drops of 1% tropicamide and 2.5% phenylephrine were administered in each eye for dilation. Proparacaine (0.5%) eye drops were applied for topical anesthesia. The eyes were lubricated with 1% methylcellulose. ERG recordings were performed with a mouse gold wire/contact electrode and 30 gauge needle reference electrodes (LKC Technologies, Gaitersburg, Md.). Needle electrodes were inserted under the skin on each side of the cheek as the references and at the base of the tail as the ground. ERGs were generated with the following program: scotopic blue filter (0 dB) at 20 µV/div single flash; scotopic white (0 dB) at 50 µV/div single flash; photopic white (0 dB) 10 µV/div single flash; and photopic white (0 dB) 20 µV/div flicker, average of 10. Five responses evoked by light were averaged in response to each luminance step. After recording, the animals were recovered and sacrificed the next day.

Multi-Electrode Array Recordings

MEA recordings were performed as previously described (Warland et al., *J. Neurosci.,* 2006, 26, 5190-5197; Sun et al., *J. Neurophysiol.,* 2008, 100, 3253-3263) on Ndufs4 KO and wild type mice (18 mice total) at: P16 (two KO; two wild type), P25 (two KO; two wild type), P32 (one KO; one wild type), P35 (one KO; one wild type), P37 (two KO; two wild type), and P45 (one KO; one wild type). Mice were euthanized with a lethal dose of pentobarbital (0.1-0.2 ml) via intraperitoneal injection. The eyes were enucleated and the retinas were removed and stored in buffered and oxygenated media (Eagle's minimum essential medium [MEME], M7278; Sigma-Aldrich, St. Louis, Mo.) at room temperature. A piece of retina was placed ganglion side down onto a 60-channel MEA (Multi-Channel Systems, Tubingen, Germany), and held in place with a piece of dialysis membrane (Spectrapore 132130; Spectrum, Los Angeles, Calif.). The tissue was superfused with buffered MEME at 1-2 ml/min at 37° C. The array electrodes were 30 µm in diameter and arranged in an 8×8 rectilinear grid with an interelectrode spacing of 200 µm. At this distance the signal for a given cell appeared on only one electrode, so each cell isolated was assigned the spatial coordinates of the electrode that recorded its signal. Analog data was acquired at 20 kHz per channel simultaneously from each electrode. After the retina was set up on the MEA, the tissue was allowed to acclimate for 5-20 minutes. Recordings were performed for 15-20 minutes during which time overall firing rates appeared stable. MEA spike identification is described in the supplemental materials. Data were analyzed by applying the Kruskal-Wallis ANOVA test with significance set at $P<0.05$.

Rapamycin Treatment

Rapamycin was dissolved in DMSO to 100 mg/mL. This was diluted in 5% PEG-400/5% Tween-20 (vehicle) to a concentration of 0.6 mg/mL, sterile filtered, and stored at −80 for long-term storage. Rapamycin treated mice were injected with 132 microliters/10 g body weight for a final dose of 8.0 mg/kg (Johnson et al., Science, 2013, 342, 1524-1528). Vehicle mice were injected with equal volume of PBS and DMSO lacking rapamycin. Injections were performed intraperitoneally using a 30 gauge needle. Two Ndufs4 KO and two wild type mice received rapamycin treatment and two Ndufs4 KO and two wild type mice received vehicle injections. Each animal was daily starting from P22 to P31. At P31 the mice were sacrificed and retinas were surgically removed and placed in RNALater and further processed for qRT-PCR as described below.

Gene Expression

Total RNA was extracted from whole retinas using affinity column purification (Qiagen, Valencia, Calif.) and processed by the UC Davis DNA Technologies & Expression Analysis Core for RNAseq. Remaining total RNA was used to generate cDNA template (Bio-Rad, Hercules, Calif.) for validation of candidate genes by qRT-PCR. RNAseq was done on three separate occasions (22 mice total), first with the eight P34 mice (four Ndufs4 KO and four wild type with an equal distribution of male and female mice in each group) that underwent ERG testing, six P33 mice (three Ndufs4 KO [one male and two female] and three wild type [one male and two female]) with no prior testing done, and eight P22 mice (four Ndufs4 KO [three male and one female] and four wild type [one male and three female]) with no prior testing. Detailed RNAseq run and analysis procedures can be found in the supplemental materials.

qRT-PCR was performed with the Roche LightCycler® 480 System (Roche, Indianapolis, Ind.) using select gene primers that were chosen based on the results of the RNAseq data (Table 1).

TABLE 1

Kegg pathways from DAVID analysis of RNAseq data from (A) P31 Ndufs4 KO retina with no prior testing or treatment and (B) P33 Ndufs4 KO retina after ERG testing. Pathways consistent in both RNAseq experiments are bolded.

| | Gene count | P-value |
| --- | --- | --- |
| RNAseq pathway analysis KEGG pathway (A) | | |
| Systemic lupus erythematosus | 4 | 7.70E−03 |
| RIG-I-like receptor signaling pathway | 3 | 3.00E−02 |
| Complement and coagulation cascades | 3 | 3.6E−02 |
| Antigen processing and presentation | 3 | 5.1E−02 |
| Toll-like receptor signaling pathway | 3 | 5.9E−02 |
| RNAseq pathway analysis KEGG pathway (B) | | |
| Antigen processing and presentation | 8 | 1.5E−05 |
| Allograft rejection | 6 | 1.6E−04 |
| Graft-versus-host disease | 6 | 1.6E−04 |
| Viral myocarditis | 7 | 1.8E−04 |
| Toll-like receptor signaling pathway | 7 | 2.4E−04 |
| Type I diabetes mellitus | 6 | 2.4E−04 |
| RIG-I-like receptor signaling pathway | 6 | 3.4E−04 |
| Cell adhesion molecules (CAMS) | 8 | 4.2E−04 |
| Autoimmune thyroid disease | 6 | 4.4E−04 |
| Cytosolic DNA-sensing pathway | 5 | 1.5E−03 |
| Chemokine signaling pathway | 7 | 5.7E−03 |
| Fc gamma R-mediated phagocytosis | 5 | 1.2E−02 |
| Systemic lupus erythematosus | 5 | 1.4E−02 |
| Natural killer cell mediated cytotoxicity | 5 | 2.4E−02 |

Tissues tested include the P22 retina used for RNAseq and eight additional P31 retinas (four KO and four wild type; equal sex distribution in each group). Primers were designed using the NCBI database and created by Integrated DNA Technologies (IDT; Coralville, Iowa). Primers were optimized by running qRT-PCR and validated by inspecting the length of the product using gel electrophoresis and inspecting the melt curve. The reference genes used in this experiment were Mapk1, Gapdh, and Actb. A list of primers can be found in Table 2.

TABLE 2

Forward and Reverse Primers for qRT-PCR of Genes.

| Gene | Forward Primers | SEQ ID NO: | Reverse Primers | SEQ ID NO: |
| --- | --- | --- | --- | --- |
| Actb | ATGTGGATCAGCAAGCAGGA | SEQ ID NO: 1 | GGGTGTAAAACGCAGCTCAG | SEQ ID NO: 27 |
| Aif1 | ATCAACAAGCAATTCCTCGATGA | SEQ ID NO: 2 | CAGCATTCGCTTCAAGGACATA | SEQ ID NO: 28 |
| B2m | CACTGAATTCACCCCCACTGA | SEQ ID NO: 3 | TCTCGATCCCAGTAGACGGT | SEQ ID NO: 29 |
| C1qa | ACAATGGCATGGTGGGCATA | SEQ ID NO: 4 | GCCGTTCTAGTCGGGAAACA | SEQ ID NO: 30 |
| C1ra | GGAGAGCTGAGGACCCAAAA | SEQ ID NO: 5 | CCACCCCATAGAACAGGGTC | SEQ ID NO: 31 |
| Ccl2 | GGCTGGAGAGCTACAAGAGG | SEQ ID NO: 6 | GGTCAGCACAGACCTCTCTC | SEQ ID NO: 32 |
| Ccl5 | TTTGCCTACCTCTCCCTCG | SEQ ID NO: 7 | CGACTGCAAGATTGGAGCACT | SEQ ID NO: 33 |
| Ccl12 | ATTTCCACACTTCTATGCCTCCT | SEQ ID NO: 8 | ATCCAGTATGGTCCTGAAGATCA | SEQ ID NO: 34 |

TABLE 2-continued

Forward and Reverse Primers for qRT-PCR of Genes.

| Gene | Forward Primers | SEQ ID NO: | Reverse Primers | SEQ ID NO: |
|---|---|---|---|---|
| Cd68 | TGTCTGATCTTGCTAGGACCG | SEQ ID NO: 9 | GAGAGTAACGGCCTTTTTGTGA | SEQ ID NO: 35 |
| Cd86 | CACAAGAAGCCGAATCAGCC | SEQ ID NO: 10 | TGTCAGCGTTACTATCCCGC | SEQ ID NO: 36 |
| Cxcl9 | CCAAGCCCCAATTGCAACAA | SEQ ID NO: 11 | AGTCCGGATCTAGGCAGGTT | SEQ ID NO: 37 |
| Cxcl10 | CCAAGTGCTGCCGTCATTTTC | SEQ ID NO: 12 | GGCTCGCAGGGATGATTTCAA | SEQ ID NO: 38 |
| Cx3cr1 | GTCTTCACGTTCGGTCTGGT | SEQ ID NO: 13 | GTCAGTGATGCTCTTGGGCT | SEQ ID NO: 39 |
| Fas | AGCCCGTTGGAGTGATTCAA | SEQ ID NO: 14 | CCCCCTGCAATTTCCGTTTG | SEQ ID NO: 40 |
| Gapdh | TGCACCACCAACTGCTTAG | SEQ ID NO: 15 | GATGCAGGGATGATGTTC | SEQ ID NO: 41 |
| Gfap | AGAAGGGGAAGGCCAAAAGT | SEQ ID NO: 16 | GGCAGGGCTCCATTTTCAATC | SEQ ID NO: 42 |
| Icam1 | TTCTCATGCCGCACAGAACT | SEQ ID NO: 17 | TCCTGGCCTCGGAGACATTA | SEQ ID NO: 43 |
| Mapk1 | CGCCTACTCAAGCACCTGAA | SEQ ID NO: 18 | CACGAGGTACACTTCGCTGA | SEQ ID NO: 44 |
| Mmp9 | CTCTAAGCCTGACCCAAGGC | SEQ ID NO: 19 | CCGTGGGAGGTATAGTGGGA | SEQ ID NO: 45 |
| Mmp12 | TGGTACACTAGCCCATGCTTT | SEQ ID NO: 20 | AGTCCACGTTTCTGCCTCATC | SEQ ID NO: 46 |
| Ndufs4 | GAGCACATCCACTTGGAAGC | SEQ ID NO: 21 | GATGTGCTCTTCTGGAACACC | SEQ ID NO: 47 |
| Nes | AGAGGACCCAAGGCATTTCG | SEQ ID NO: 22 | TGCCTTCACACTTTCCTCCC | SEQ ID NO: 48 |
| Opa1 | CCCAGCTCAGAAGACCTTGC | SEQ ID NO: 23 | CCAATTTGGGACCTGCAGTGA | SEQ ID NO: 49 |
| Tlr2 | CAGTGGCCAGAAAAGATGCG | SEQ ID NO: 24 | CCTCCAGCGTCTGAGGAATG | SEQ ID NO: 50 |
| Tlr3 | GAGCCACAGTGATAGATGGCA | SEQ ID NO: 25 | TCCAGCAGAAGAGACACAACA | SEQ ID NO: 51 |
| Tlr4 | CTCTGGGGAGGCACATCTTC | SEQ ID NO: 26 | TGCTCAGGATTCGAGGCTTT | SEQ ID NO: 52 |

The change in PCR products as the reaction proceeded was monitored by SYBR green dye (Invitrogen, Grand Island, N.Y.). Sample volume was 10 µl and samples were run in technical triplicates. Quantification cycle (Cq) values obtained by the Lightcycler were analyzed by normalizing the values to the reference genes and delta Cq values were calculated to determine relative gene expression values compared to wild type. Delta delta Cq was also calculated to determine the fold change difference between Ndufs4 knockout and wild type. Significance, $p<0.05$ was determined using two sample independent student's t-test statistics with equal sample size and assuming equal variance.

Multiple Immunofluorescent Labeling

All antibodies used in this current study are listed in Table 3.

TABLE 3

Antibodies used for immunohistochemistry study.

| Antigen | Immunogen | Manufacturer | Cat. No. | Species | Working dilution (µg/mL) |
|---|---|---|---|---|---|
| GAD67 | Recombinant feline GAD67 | Chemicon | AB5992 | Rabbit | 2 |
| GAD67 | Recombinant human GAD67 | Millipore | MAB5406, clone 1G10.2 | Mouse | 2 |
| Brn3a | Synthetic peptide, human Brna3a (aa 141-157) | Millipore | AB5945 | Rabbit | 5 |
| Iba1 | Synthetic peptide, human, rat, mouse Iba1 c-terminus | Wako | 019-19741 | Rabbit | 1 |
| ChAT | Human placental enzyme | Millipore | AB144 | Goat | 10 |
| Gfap | Synthetic peptide, Asp395 of human Gfap protein | Cell Signaling | 12389s | Rabbit | 1:500 |

Immunohistochemical labeling was carried out using the indirect fluorescence method. Controls included no primary, and no primary or secondary for each antibody used. Sections were incubated in a blocking buffer containing 10% normal donkey serum, 2% bovine serum albumen (BSA) and 0.5% Triton-X-100 in phosphate buffer saline (PBS, pH 7.2) for 1 hour at room temperature. Sections were incubated overnight at 4° C. in blocking buffer containing primary antibodies. After briefly washing in PBS, secondary antibodies diluted in PBS were applied for 1 hour at room temperature. Secondary antibodies were conjugated to Alexa 488 or Alexa 594 (1:500; Molecular Probes, Eugene, Oreg.). Finally, sections were counterstained with 4',6-diamidino-2-phenylindole (DAPI) (1:500; Kirkegaard & Perry Laboratories, Gaithersburg, Md.) for 1 minute. Sections were coverslipped using either Vectashield (Vector Laboratories, Burlingame, Calif.) mounting media or Prolong Gold Antifade reagent (Life Technologies, Grand Island, N.Y.). Fluorescent images were captured using the Nikon Eclipse E1000 (Melville, N.Y.) and Olympus FV500 (Tokyo, Japan) confocal microscopes.

Cell Counts and Immunofluorescence Quantification

Quantification of cell number and/or immunofluorescence labeling intensity was obtained from 4 animals (2 KO and 2 wild type; 16 total) at the following ages; P16, P25, P31, and P42. A mix of both male and female (75% male, 25% female) mice was used for analyses and we observed no obvious differences in cell number or immunofluorescence between the sexes. Because thickness and cell number varies across the retina (Jeon et al., *J. Neurosci.,* 1998, 18, 8936-8946), sections were chosen for immunohistochemistry and cell counts from regions evenly spaced approximately 150-200 μm apart so as to sample regions from central retina out to the periphery. Conventional inclusion/exclusion criteria were followed (Fox et al., *Toxicol. Appl. Pharmacol.,* 2011, 256, 258-267); any cell touching the left line of the grid was included in the count, any cell touching the right line of the grid was excluded. To be included in the counts immunoreactive cells had to have a nucleus as determined by DAPI staining. Equal numbers of images per age group and condition were analyzed. Values across each section from nasal to temporal portions of the retina were pooled together and included in the averages for each condition. All measures were obtained exclusively from the dorsal half of each retina and this process was identical for each eye examined. Observers were blind to genotype.

For ChAT immunolabeled sections, approximately 450-850 cells, depending on the age and/or genotype, were counted for each condition. These counts were collected from 7-10 images collected from 7-10 evenly spaced sections. Using Neurolucida software, (MicroBrightfield, VV), a grid of 150 μm square was placed in the center of each image and cell counts were made within this region. The same procedure was followed for Iba1 cell counts (between 60 and 200 cells depending on age and/or genotype) using collapsed confocal stack images.

Quantification of Brn3a cell number and GAD67 immunofluorescence levels was done using ImageJ software (Rasband, W S, ImageJ, U.S. National Institutes of Health, Bethesda, Md., USA, 1997; Schenider et al., *Nat. Methods,* 2012, 9, 671-675). For Brn3a, approximately 700-1000 cells, depending on age and/or genotype, were counted for each condition. These counts were collected from 3-4 images from 8-10 sections. Immunopositive cells were counted along a 150-200 μm region from the central portion of each image of the retinal ganglion cell layer. ChAT positive cells that colocalized Brn3a were removed from the counts. For GAD67 labeling, since no discernable somal labeling was detected we measured the intensity of immunofluorescence within the IPL where the dendrites and terminals of amacrine cells reside. To account for potential variability in immunolabeling between samples not related to genotype we normalized IPL values against non-specific background label overlying the outer segments of photoreceptor cells. Measures were made from a similar region and number of sections as those for Brn3a.

Statistical analyses of cell number and immunofluorescence were made in either Origin (OriginLab, Northampton, Mass.) or Excel software (Microsoft Corp., Redmond, Wash.). Significance, $p<0.05$ was determined using two sample independent student's t-test statistics with equal sample size and assuming equal variance.

Western-Blot Analysis

Retinas were homogenized in 2× lysis buffer (Cell Signaling Technology, Danvers, Mass.) and 20 μg of protein per sample were analyzed in 4-12% NuPAGE Bis-Tris gel (Novex, Grand Island, N.Y.). After electrophoresis, proteins were transferred to nitrocellulose membranes using an Iblot dry blotting system (Invitrogen). The membranes were blocked with LI-COR Odyssey (Lincoln, Nebr.) block buffer, and subsequently incubated with anti-GFAP (Cell Signaling) and anti-Tubulin (Developmental Studies Hybridoma Bank, University of Iowa, Iowa City, Iowa) antibodies overnight. The LI-COR Odyssey scanner was used for western blot detection with goat-anti mouse IRDye 680RD and goat-anti rabbit IRDye 800CW secondary antibodies (LI-COR). Image studio (LI-COR) was used to analyze western blot results.

Intensity measurements and quantification of Gfap were made using three wild type and three Ndufs4 KO mice. Using Nikon NIS-elements imaging software, three images of one section of each animal retina were analyzed. Gfap mean staining intensity of the GCL was subtracted from the background mean intensity.

Example 2: Repurposing FDA-Approved Molecules to Identify Potential Leads for a Mitochondrial Blinding Disease This example illustrates that drugs such as papaverine, zolpidem, methoxamine, methenamine, methotrexate, azathioprine, fluorouracil, and zidovudine are useful to prevent, alleviate, attenuate the progression of, or treat mitochondrial diseases including those that can lead to vision loss or blindness.

Abstract

Leber's hereditary Optic Neuropathy (LHON) is one of the commonest inherited mitochondrial diseases, in which mitochondrial complex 1 mutations cause optic atrophy and vision loss. Currently there is no FDA-approved therapy for LHON and few ongoing clinical trials. We took a repurposing approach to LHON by screening FDA-approved drugs for their ability to rescue a LHON-specific cellular defect. We identified a LHON-specific defect in the mutant cells ability for complex I to drive ATP synthesis under stress, and this parameter was reduced in cells bearing the three commonest LHON mutations, 11778, 3460, and 14484, in proportion to their severity. Then, 1600 drugs were screened in an optimized high-throughput assay for their effect to rescue this parameter in LHON 11778(G>A) cells, to identify 34 protective molecules. Of those 34, 2 were consistently protective in six-point concentration-response curves, zolpidem and papaverine. These drugs rescued complex-I driven ATP synthesis in mutants and controls. Thus, these are the first-ever drugs to rescue a LHON-specific defect in cells, and the first-ever demonstration of a small molecule that increases complex-I driven ATP synthesis. Putative mechanisms of papaverine and zolpidem are phosphodiesterase inhibitor and GABAA receptor agonist. Mechanistic experiments suggested that zolpidem was H89-inhibitable, suggesting a mechanism related to cAMP. In conclusion, LHON mutations can cause defects in mitochondrial complex I-mediated ATP synthesis under stress, which can be rescued at the cellular level by zolpidem and papaverine.

Introduction

One of the most common mitochondrial disease is Leber's Hereditary Optic Neuropathy (LHON), whose prevalence is about 1/45,000 in Europe. LHON is initially precipitated by painless and acute unilateral loss of central vision and gradually leading to bilateral total vision loss and blindness. Optic nerve atrophy and demyelination, and loss of retinoganglial cell layer are some of the typical pathologic changes that are observed in LHON. The majority (>90%) LHON cases have been associated with three primary mtDNA mutations, namely: G11778A (ND4 subunit of complex I), G3460A (ND1 subunit of complex I), T14484C (ND6 subunit of complex I) (Mackey et al., American Journal of Human Genetics, 1996, 59, 481-485). These mutations are reported to compromise the complex I-driven ATP synthesis (Baracca et al., Archives of Neurology, 2005 62, 730-736). In addition, the prevalence is highly observed in young adult males (80%) between 15 to 30 years. A correlation between the primary mutations and the clinical outcomes has been observed (Oostra et al., J Med Genet, 1994, 31, 280-286; Riordan-Eva et al., Brain, 1995, 118 (Pt 2), 319-337); Spruijt et al., Am J Ophthalmol, 2006, 141, 676-682). The 11778 (G>A) mutation is the most common and severe among the three primary LHON-associated mutations. Vision loss from this mutation is almost always irreversible and there is only 4% chance of spontaneous visual improvement. The 3460 mutation confers intermediate severity with 20-40% chance of recovery. By contrast, the 14484 (T>C) mutation is the lease severe, and there is 37-65% chance of spontaneous reversal of vision loss. Currently there is no FDA-approved therapy for the treatment of LHON.

The lack of FDA-approved therapy for LHON demonstrates an unmet need in the treatment of this disease. A repurposing approach towards drug discovery is one viable strategy to address this need, and has the advantage drugs are already clinically established. In the current study we identified a rotenone-dependent defect in complex I-driven ATP synthesis in LHON mutant cells that could be measured in high-throughput, and a library of 1600 clinically tested drugs was screened. Drugs were identified that rescued the LHON-dependent defects in ATP synthesis, and they appear to work through demonstrably different mechanisms.

Results

Figure 17:
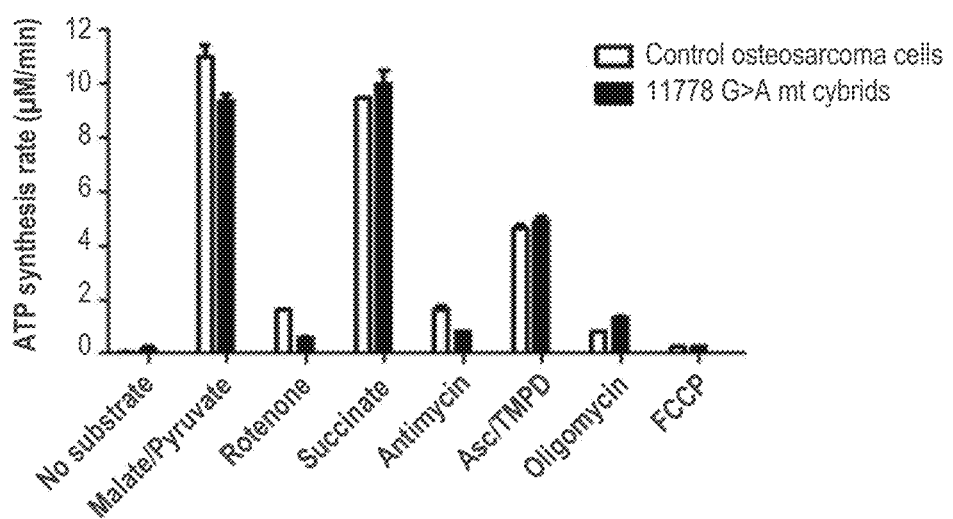
FIG. 17 depicts optimization of high-throughput format complex I-driven ATP synthesis assay in control osteosarcoma cells and LHON mutant (11778 G>A) cells. Cells were permeabilized with streptolysin O and mitochondrial complex I-driven ATP synthesis was measured in (1) the absence; or (2) the presence of complex I substrates [malate (5 mM)/pyruvate (5 mM)]; (3) malate/pyruvate+rotenone (1 μM), (4) malate/pyruvate+rotenone+succinate (5 mM); (5) malate/pyruvate+antimycin A (1 μM); (6) malate/pyruvate+ antimycin A+ascorbate/TMPD; (7) malate/pyruvate+oigomycin (1 μM) and (8) malte/pyruvate+FCCP (5 μM). The data is presented as ATP synthesis rate+standard deviation from one representative experiment.

Optimization of a High Throughput Assay for Mitochondrial Complex I-Driven ATP Synthesis Since it has been previously reported that, LHON has a complex-I-driven ATP synthesis defect (Baracca et al., Archives of Neurology, 2005 62, 730-736), we selected this biochemical parameter to screen on between control and LHON-mutant cells. A luminescence-based assay to measure complex-I-driven ATP synthesis in high throughput was recently demonstrated (Fujikawa et al., Biochemical and Biophysical Research Communications, 2010, 401, 538-543). We improved this previously reported luminescence-based assay to measure complex-I-driven ATP synthesis in a 96-well format, we observed these improvements [decreased # of plate washes] were absolutely essential to reduce variability to (Z'≥0.4). Optimum cell density for the assay was determined to be 50,000 cells/well for the osteosarcoma cytoplasmic hybrids (cybrid). To confirm that the luminescence observed in the assay was from mitochondrial ATP synthesis, we used different substrates and inhibitors of mitochondrial complexes to validate our assay. As expected, rotenone (1 µM), antimycin (1 µM), and oligomycin (1 µM) inhibited the mitochondrial ATP synthesis while succinate (5 mM) and ascorbate/TMPD reversed the rotenone, and antimycin inhibition, respectively (FIG. 17)

Rotenone Discriminates LHON Mutant Complex I Driven ATP Synthesis

Figure 11A:
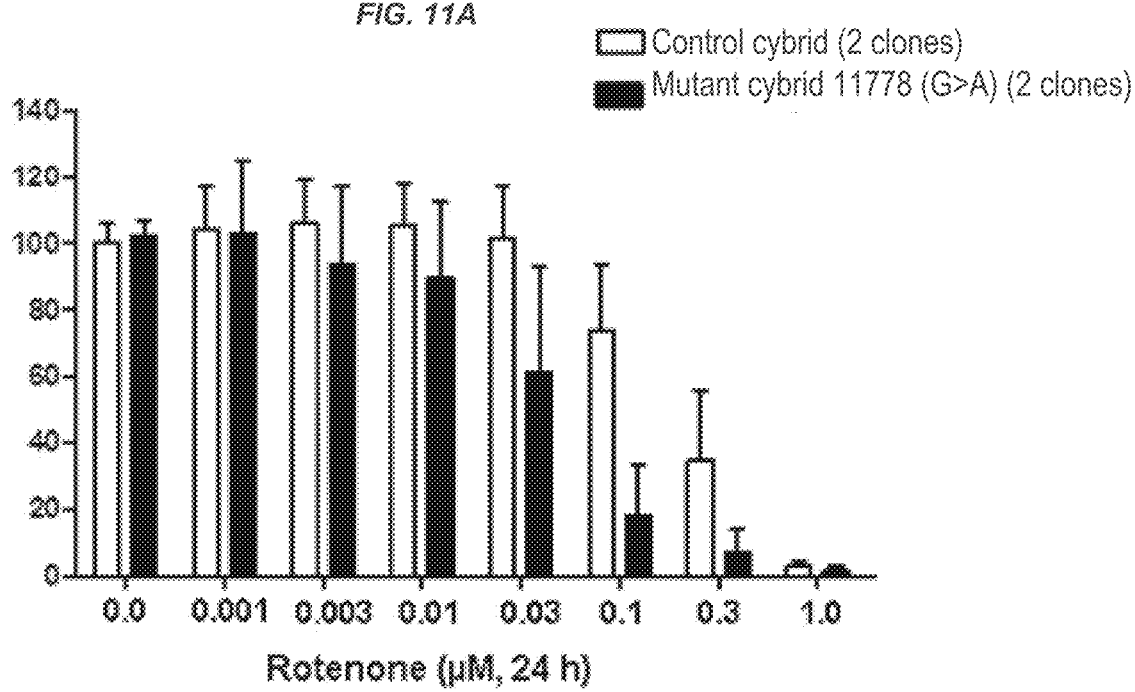

Among the various LHON-associated mutations, 11778 (G>A) mutation encoding ND4 subunit of mitochondrial complex I is the most prevalent and the most severe (Oostra et al., J Med Genet, 1994, 31, 280-286). It has been previously hypothesized that some external stress factors are responsible for the precipitation of vision loss in LHON (Chalmers et al., Biochimica et Biophysica Acta, 1999, 1410, 147-158). To understand the 11778(G>A) mutant mitochondrial functionality under stress, we evaluated the effect of a complex I inhibitor on complex I-driven ATP synthesis using an osteosarcoma cybrid model (FIG. 11A). Two different clones of the mutant (HCT22 and HFF3) and the control (HGA2 and H1959) cybrid cells were treated with rotenone (0.001 µM-1 µM) in half-log increment and complex I-driven ATP synthesis was measured after 24 h. The complex I-driven ATP synthesis in 11778(G>A) mutant cybrids were found to be highly sensitive to rotenone when compared to control. The rotenone treatment, however, did not affect the cell viability of the cybrids within 24 h (data not shown). This was in contrast to the earlier report which observed that 11778(G>A) mutation imparts rotenone resistance on the enzymatic activity of complex (Carelli et al., *Neurology*, 1997, 48, 1623-1632).

Figure 11B:
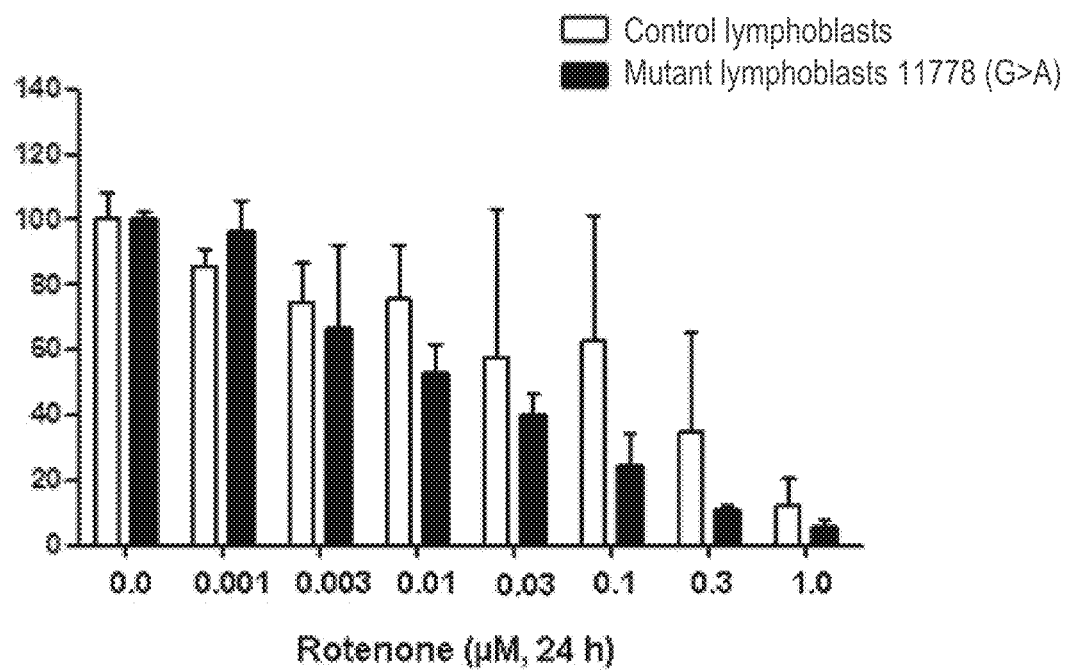

Rotenone Sensitive Complex I Driven ATP Synthesis Defects are a General Consequence of LHON Mutations, and Proportional to Severity To confirm that the enhanced effect of rotenone is not unique to the cybrid model we evaluated the LHON-dependent effects of rotenone in the gender-matched lymphoblasts. The differential effect of rotenone on the 11778(G>A) mutant was clearly reproducible in the lymphoblast model as well (FIG. 11B), thus rotenone-sensitivity is a consistent consequence of LHON mutations across cell types. To determine whether the screening parameters were identifying a biochemical difference that was conferred by LHON mutations, we evaluated rotenone's effects on the 3 most common LHON mutations in cybrids. Interestingly, the effect of the biochemical defect in ATP synthesis was directly in proportion to the severity of the disease in humans, i.e., 11778(G>A) mutation has worst ATP defect, 3460(G>A) intermediate, and 14484(T>C) mildest, just as in human LHON (FIG. 11C).

Screening for Rescue of Sensitivity to LHON-Dependent Defects

Figure 12:
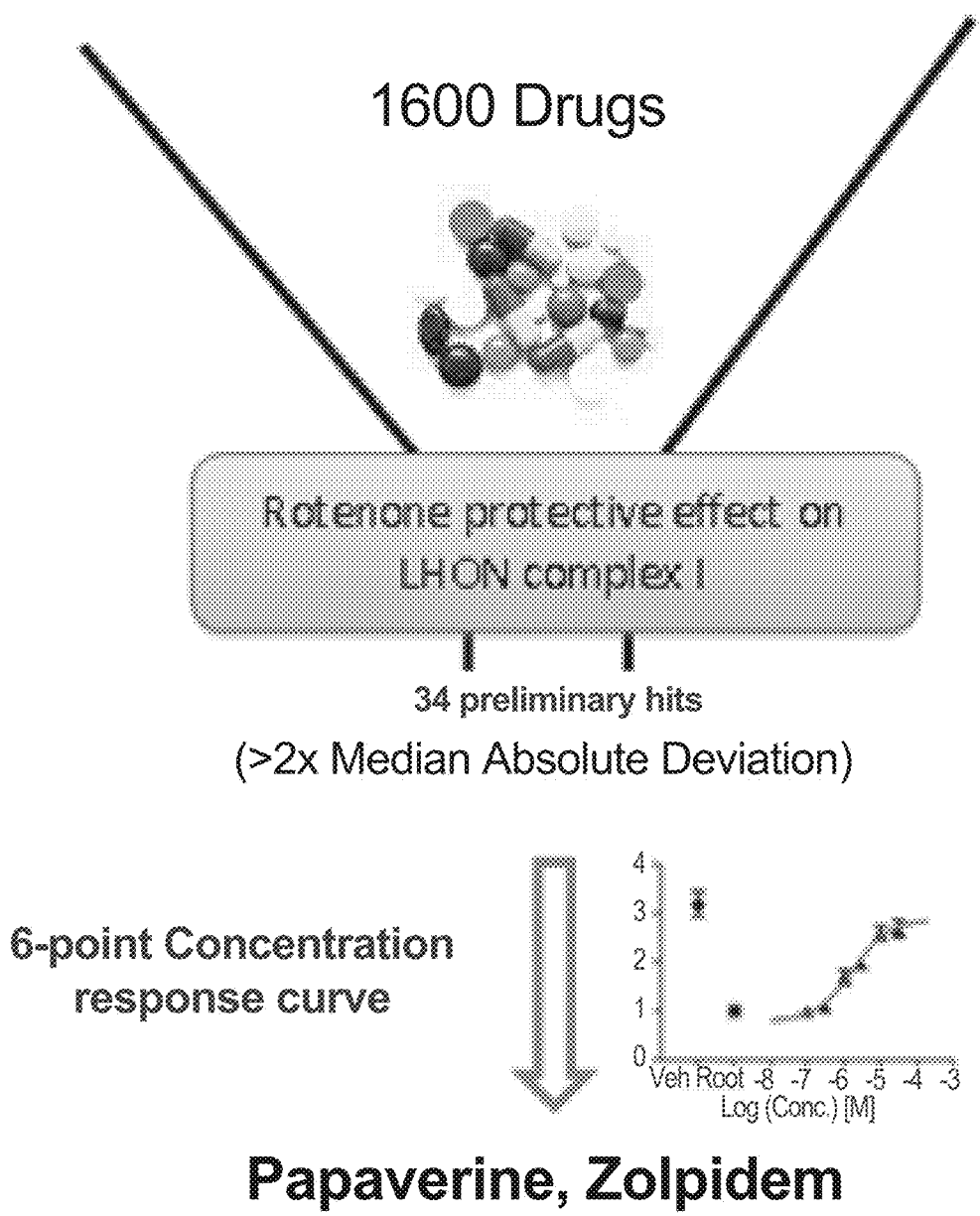
FIG. 12 shows the drug screening procedure and some of the identified drugs.

In order to find a potential therapy for LHON, we used this rotenone-sensitivity in cybrids as our screening model (FIG. 12). We hypothesized that the differential rotenone-responsiveness is due to the mitochondrial complex I defect caused by the genetic mutation and the drugs that can reverse rotenone sensitivity of LHON cybrids, can possibly be used therapeutically to treat LHON. Since the 11778 (G>A) mutation is the most prevalent LHON-associated mutation and it showed the highest ATP synthesis inhibition by rotenone, one of the 11778 clone (HCT) was used as our screening system as it showed higher sensitivity comparatively to the other (FIG. 13B).

Figure 13A:
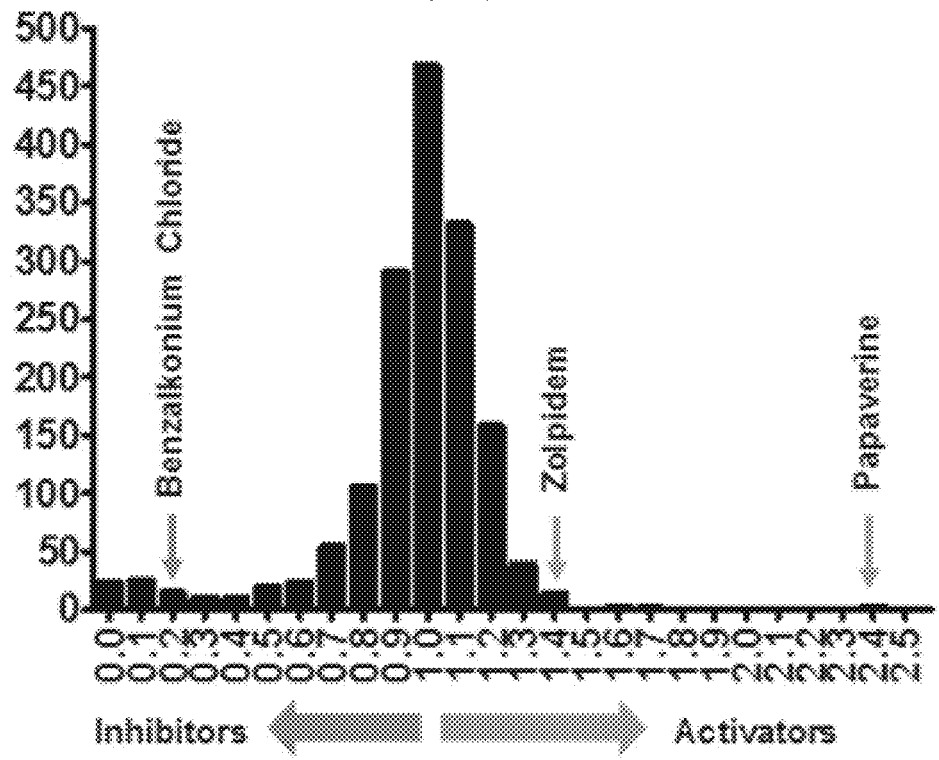
FIGS. 13A and 13B depict histograms of modulators of rotenone-inhibited complex I-driven ATP synthesis in LHON cybrids (11778 G>A) identified by a high-throughput drug screen. The luciferase-based complex I-driven ATP synthesis assay was used to screen a library of 1600 drugs at 10 µM (20 h). The vehicle control was 0.05% DMSO; the negative control was 0.03 µM rotenone.
Figure 13B:
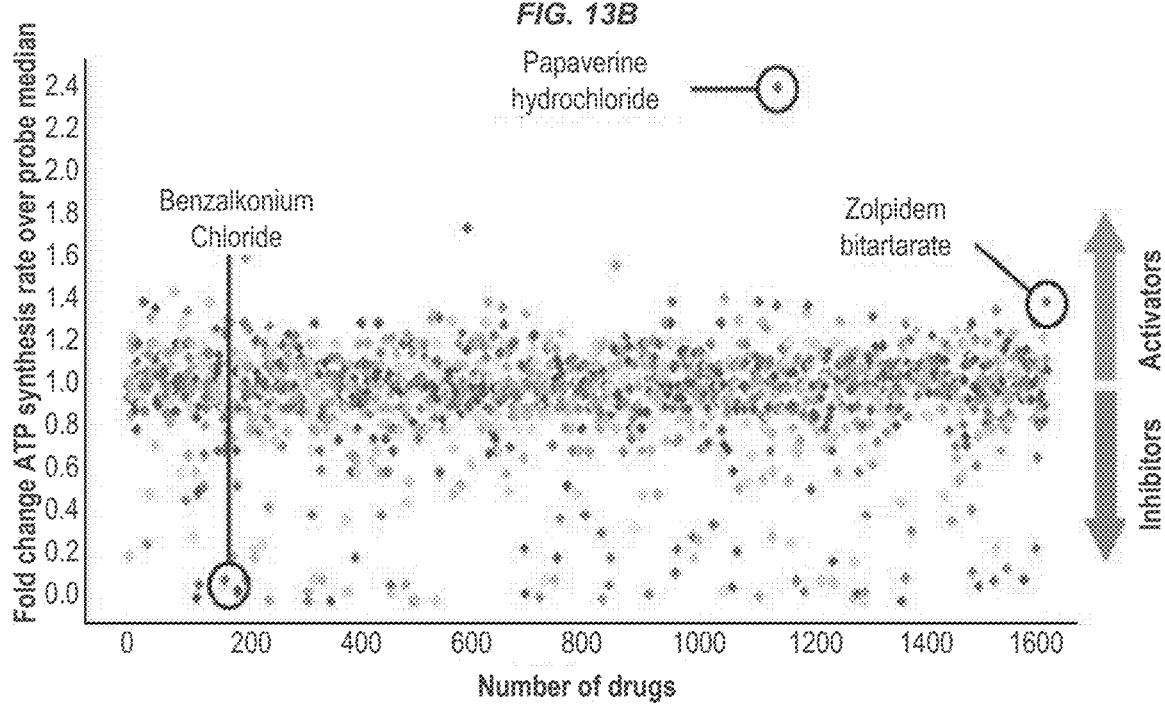

Screening a Drug Library of Clinically-Used Drugs with Known Pharmacokinetics and Safety Profile We screened the Pharmakon™ collection (Microsource Discovery Systems) of 1,600 FDA-approved and/or clinically evaluated drugs (FIG. 13A). The drugs that showed an enhancement of ATP synthesis rate greater than two times of the median absolute deviation (MAD) and were consistent in both the plates, were considered as preliminary hits. The preliminary hits were subject to the same assay in triplicate for reconfirmation. There were 34 preliminary hits including papaverine hydrochloride, methotrexate (+/−+), methoxamine HCL, azathioprine, zolipdem, methenamine, fluorouracil, and zidovudine (e.g., azidothymidine or AZT) (see, Table 4). Two drugs were confirmed in 6-point dose curves, i.e., 0.1 µM to 30 µM at half-log increments. Zolpidem, a γ-aminobutyric acid receptor subtype A (GABAA)-agonist, was found to be the top hit, the other top hit was the phosphodiesterase inhibitor papaverine.

TABLE 4

Top 8 drugs that showed an enhancement of ATP synthesis rate greater than two times the median absolution deviation of (MAD).

| Drug Name | Fold change of ATP synthesis rate greater than 2x Median Absolution Deviation |
|---|---|
| Papaverine hydrochloride | 2.4 |
| Methotrexate | 1.2 |
| Methoxamine HCl | 1.4 |
| Azathioprine | 1.4 |
| Zolpidem | 1.4 |
| Methenamine | 1.3 |
| Fluorouracil | 1.1 |
| Zidovudine | 1.2 |

The Protective Effect of Papaverine and Zolpidem are LHON-Mutation Specific

Figure 14A:
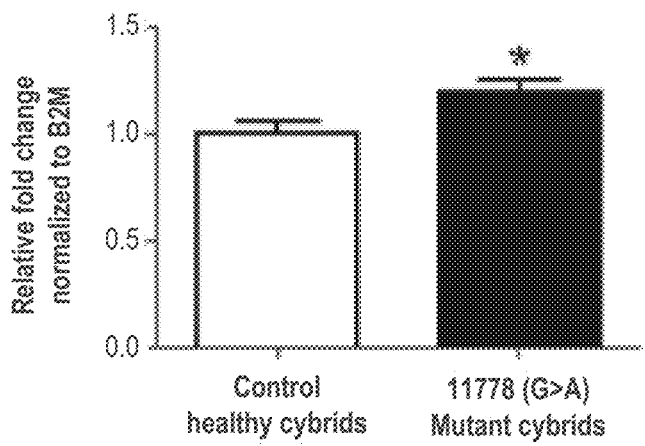
FIGS. 14A-14C illustrate the effect of drugs on the mitochondrial copy number. Difference of mitochondrial copy number between 11778 (G>A) mutant and control cybrids (FIG. 14A). Effect of zolpidem and papaverine on the control healthy cybrid mitochondrial copy number (FIG. 14B) and 11778 (G>A) mutant cybrid mitochondrial copy number (FIG. 14C). Cells were treated with either vehicle or one of the drugs at specified concentration for 24 h. The cells were harvested after 24 h and the ratio between MT-TL1 and B2M was determined. Data is presented as average relative fold change±std. deviation from three independent observations. Statistical significance (p<0.05) is denoted by '*' and was determined by one way ANOVA and Dunett's post hoc test.
Figure 14B:
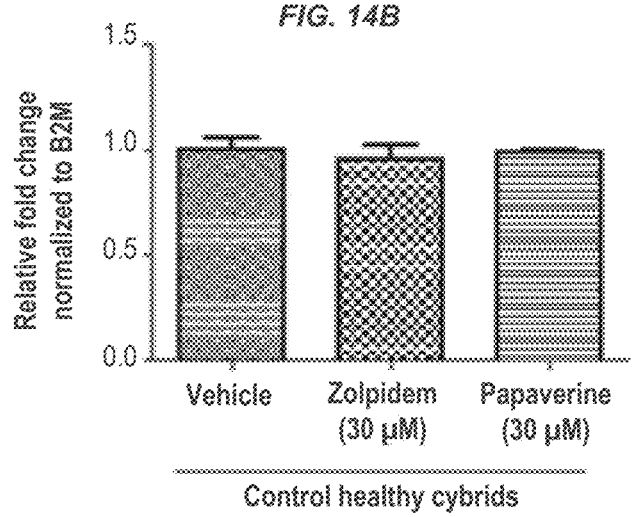
Figure 14C:
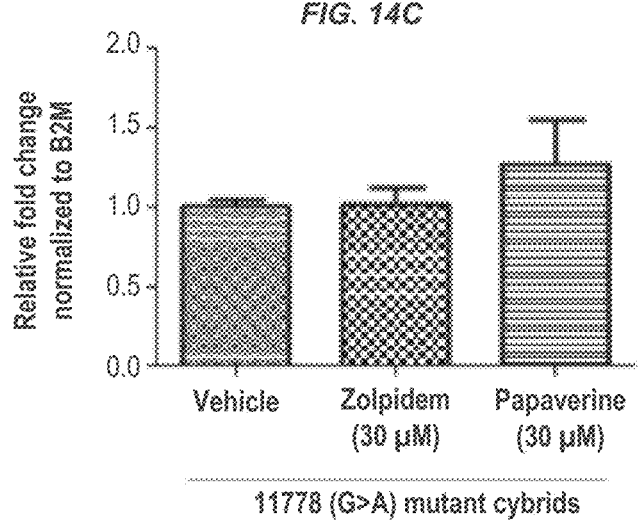

A first question to ask was whether papaverine and zolpidem had a general or LHON-specific effect, and this is addressed in FIG. 12. Mutant cells were observed to have significantly more mitochondria compared to control cells (FIG. 14A). Zolpidem and papaverine do not appear to be mitoproliferative, and in support of that did not significantly change the ratio of mtDNA/nDNA in either control or LHON mutant cells [11778(G>A)] after 24 hrs exposure (FIGS. 14B and 14C).

Studying the Protective Mechanisms of Papaverine

Figure 15A:
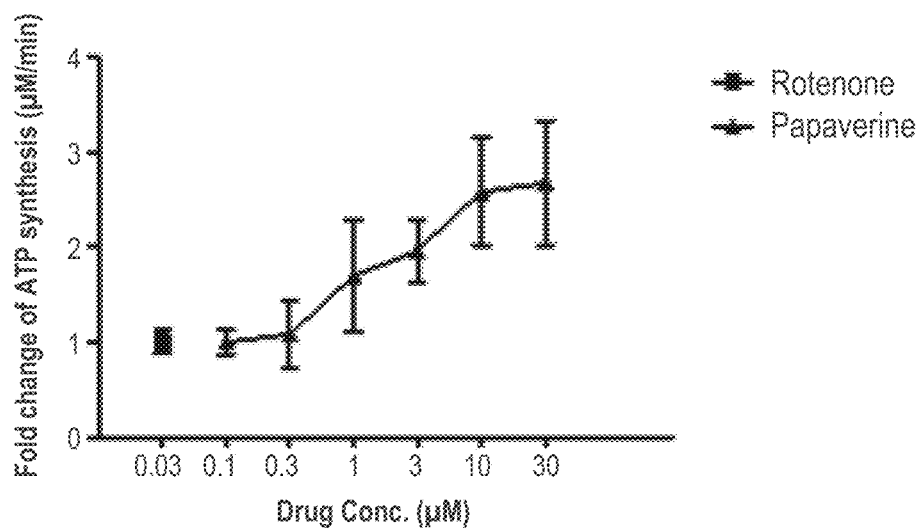
FIGS. 15A and 15B illustrate the concentration-dependent rotenone de-sensitization effect of papaverine or zolpidem on LHON mutant [11778 (G>A)] cells.
Figure 18A:
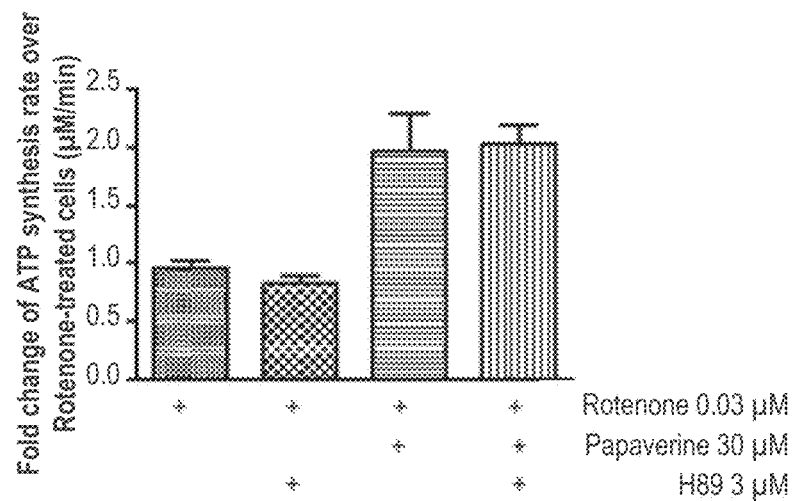
FIGS. 18A and 18B show the activity of papaverine on rotenone-induced ATP synthesis inhibition in LHON mutant (11778 G>A) cells.
Figure 18B:
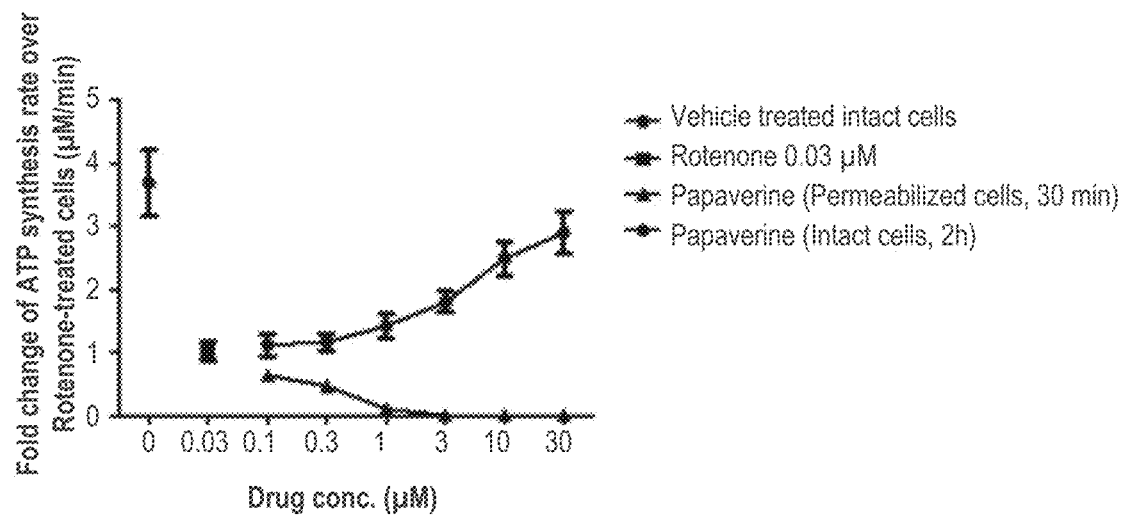
Figure 19A:
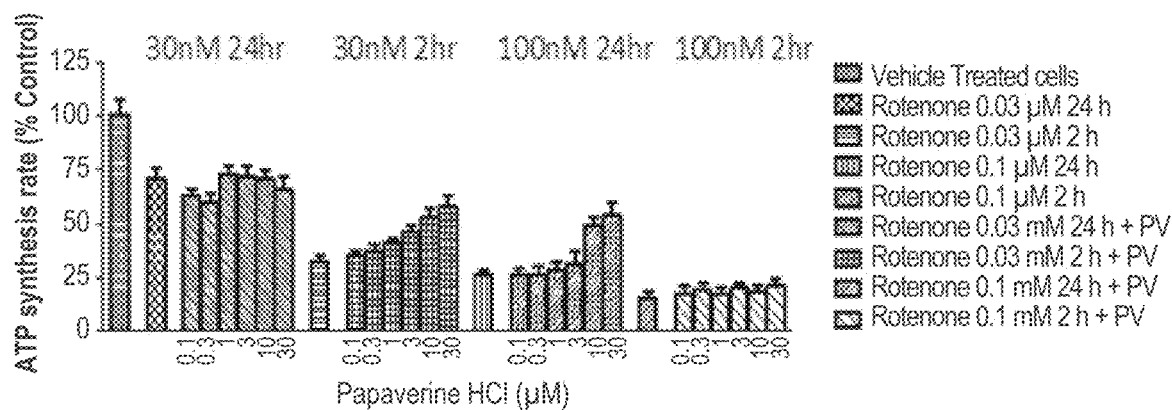
FIGS. 19A and 19B show papaverine dose dependently stimulates complex 1-dependent ATP synthesis in normal cells inhibited by rotenone.
Figure 19B:
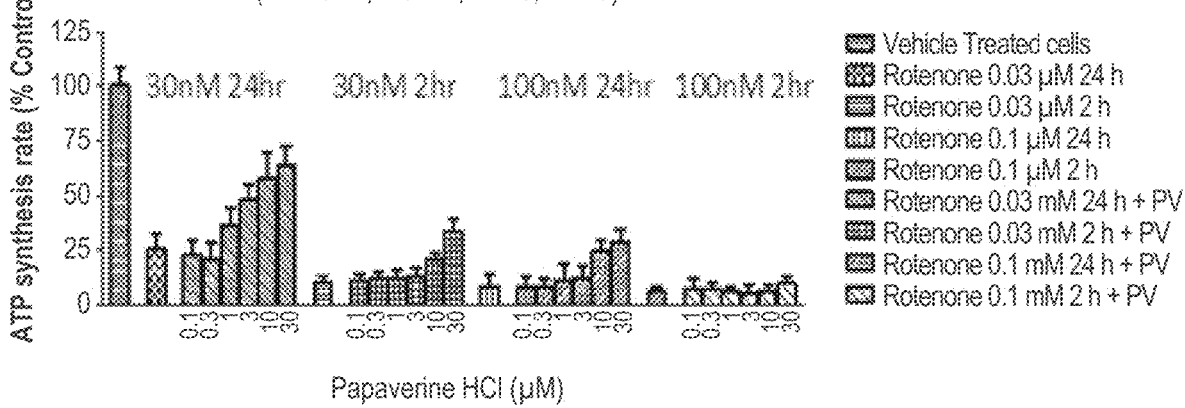

The first hit papaverine, an isoquinoline opium alkaloid, dose-dependently reversed the rotenone sensitivity in the LHON mutant cells [11778(G>A)] (FIG. 15A). Furthermore, the protective effect of papaverine was observed in cells treated for as little as 2 hrs (FIG. 18B) or as much as 24 hrs. The concentration-dependent reversal effect of papaverine on the rotenone-induced ATP synthesis inhibition was stronger than Zolpidem. It was, however observed that when the papaverine treatment was done in permeabilized cells (30 min) instead of intact cells (2 h), papaverine inhibited complex I driven ATP production (FIG. 18B). This indicates that the effect of papaverine requires either some kind of feedback mechanism or cellular metabolism. Papaverine's nominal target is considered to be the inhibition of phosphodiesterase 10 (PDE10) (Chappie et al., Journal of Medicinal Chemistry, 2007, 50, 182-185). Phosphodiesterases degrade cyclic AMP (cAMP), in a desensitization response (Bender et al., Pharmacological Reviews, 2006, 58, 488-520; Moorthy et al., Molecular & Cellular Proteomics: MCP, 2011, 10, M110.002295). Papaverine is a known inhibitor of cAMP/cGMP phosphodiesterases and is known to increase the cellular cAMP levels. This was interesting because traditionally extra-mitochondrial cAMP-PKA signaling axis have been postulated to increase mitochondrial function/biogenesis (Feliciello et al., Cellular Signaling, 2005, 17, 279-287) and recently intra-mitochondrial cAMP has been demonstrated to regulate mitochondrial PKA and be a major regulator of oxidative phosphorylation (Acin-Perez et al., Cell Metabolism, 2009, 9, 265-276; Valsecchi et al., Physiology (Bethesda, Md.), 2013, 28, 199-209). Thus we tested the hypothesis that papaverine's protective effect in LHON cells was through action as a phosphodiesterase inhibitor and subsequently as a stimulator of protein kinase A, which is known to stimulate mitochondrial functions.

Two commonly available tests of the hypothesis are the PKA inhibitor H89 (Gomez-Concha et al., The International Journal of Biochemistry & Cell Biology, 2011, 43, 1402-1411; Valsecchi et al., Physiology (Bethesda, Md.), 2013, 28, 199-209), and the known protein kinase A stimulator forskolin (Li et al., Cell Research, 2008, 18, 311-323). However, the PKA inhibitor H89 did not decrease papaverine's ability to protect from rotenone (FIG. 18A). We also tested forskolin, a known potent stimulator of cellular cAMP production in 11778 cells. Forskolin administration at physiologically relevant doses did not produce any measurable protection (data not shown). Thus our data do not support the idea that papaverine's protective effect is mediated through stimulation of the cAMP-PKA signaling pathway. Thus the mechanism of protective effect of papaverine needs further investigation and is currently not known.

Protective Mechanism of Zolpidem

The GABAA receptor-agonist zolpidem dose-dependently reversed the rotenone-sensitivity of the 11778(G>A) cells (FIG. 14A). Compared to vehicle pre-treated cells, cells pre-treated with zolpidem (3, 10, and 30 µM) show a significantly higher ATP synthesis rate when subsequently treated with rotenone (0.03 µM). The ATP synthesis rate in the zolpidem-treated (30 µM) cells, was 2-times higher than the vehicle-treated cells after being treated with rotenone (0.03 µM).

Figure 16A:
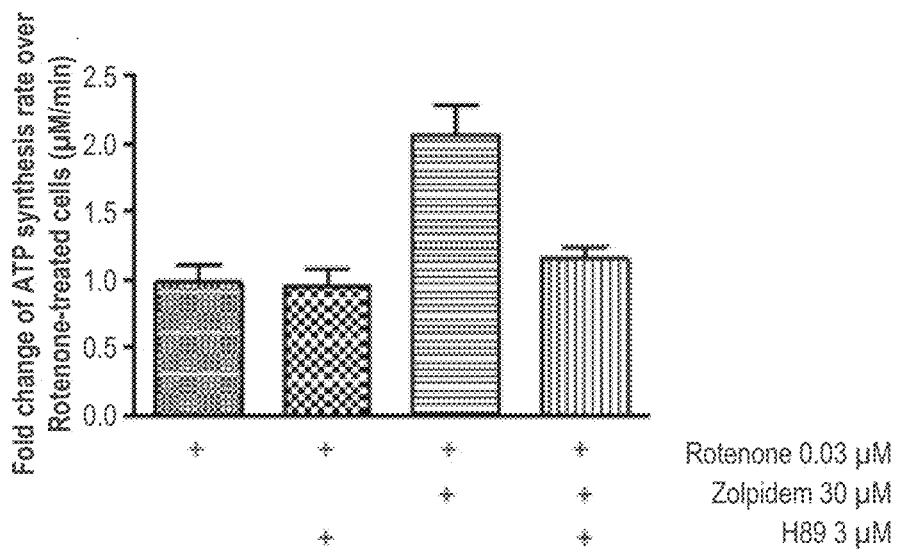
FIGS. 16A and 16B depict the activity of zolpidem on rotenone-induced ATP synthesis inhibition in LHON mutant (11778 G>A) cells when treated with a potential drug inhibitor.
Figure 16B:
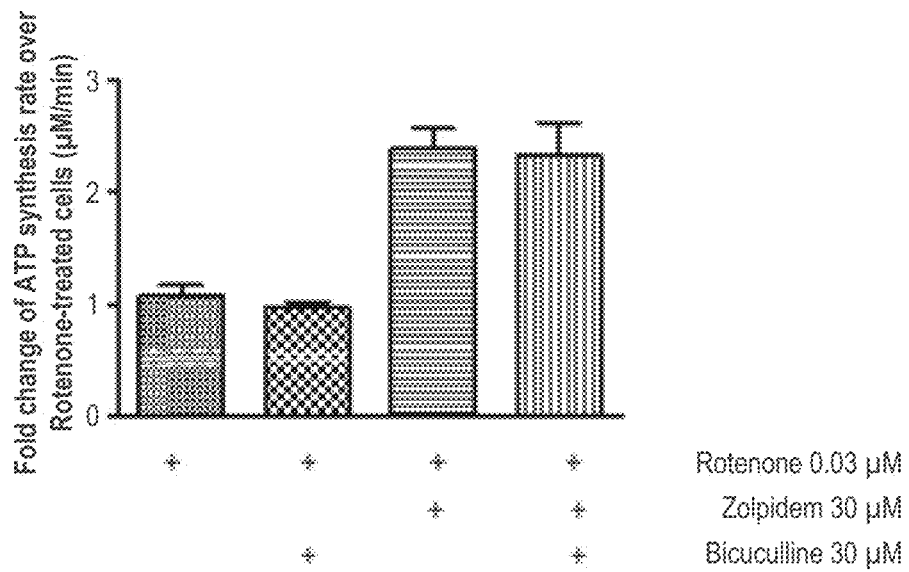

Since zolpidem is a well-known GABAA receptor agonist, it was primarily hypothesized that the effect of zolpidem might be GABAA-mediated. It was, however, observed that a GABAA antagonist bicuculine had no significant effect on the concentration-dependent reversal of rotenone inhibition by zolpidem (FIG. 16B); however it is not known if osteosarcoma cells contain GABAA receptors. Another possible hypothesis is that it might be acting through the mitochondrially located peripheral benzodiazepine receptors (PBR) which needs further investigation.

Figure 15B:
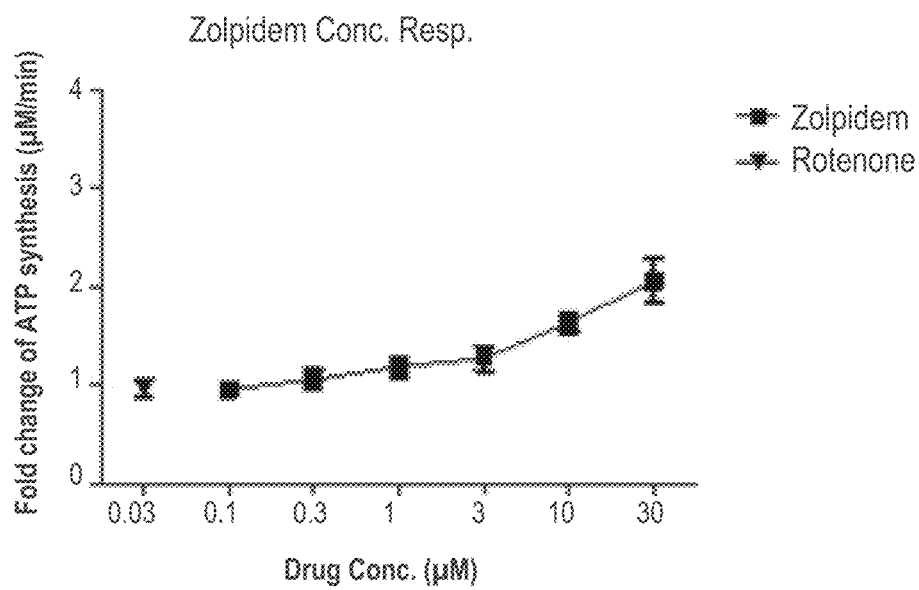

In addition, possible involvement of cAMP-PKA signaling was also evaluated using the H89 experiment. Incubation of H89 (3 µM) with zolpidem (30 µM) reversed the rotenone rescue effect of zolpidem (FIG. 15B). Since the concentration of H89 needed to completely reverse the protective effect of zolpidem is much higher than its PKA inhibitory concentrations (IC$_{50}$ 135 nM) it is likely that the protective effect of zolpidem is mediated through some other kinases for which further investigation is necessary.

Summary and Conclusions

Leber's hereditary optic neuropathy-targeted drug discovery efforts are needed urgently as the current treatments for LHON are based on anecdotal evidence. In this study we have discovered the LHON mutant cells are more sensitive to complex I driven ATP synthesis by rotenone. Subsequently, we also developed a new method in which the differential effect of complex I-inhibitor rotenone on the complex I-driven ATP synthesis of healthy control and LHON mutant cybrid cells can be utilized to screen and identify small molecules with potential benefits in LHON. We screened 1600 small molecules which are either FDA-approved drugs or undergoing clinical trials by using our newly developed screening method. We screened them in duplicate and found 34 hits which shown stimulation of rotenone-inhibited complex I-driven ATP synthesis in LHON mutant. Out of these 34 hits, the top two hits were confirmed and showed a dose dependent response. These two hits were identified as zolpidem and papaverine. It is predicted that the effect of zolpidem is mediated through a kinase while the effect of papaverine is not. In addition, neither of these molecules engages the PDE-cAMP-PKA pathway.

Materials and Methods

Cells: Control and LHON mutant cybrids were cultured in Dulbecco's Modified Eagle's Medium (DMEM) containing 2 mM glutamine and 100 mM sodium pyruvate, under 5% carbon dioxide at 37° C. The medium was further supplemented with 10% fetal bovine serum, 50 µg/mL uridine and antibiotics (penicillin/streptomycin).

Chemicals: Chemicals were obtained from Sigma-Aldrich.

Measurement of complex I-driven ATP synthesis: The cybrid cells were seeded at 50000 cells/well in 100 µL of medium, in a white, opaque-bottom, 96-well plate coated with poly-D-lysine (Corning) and was incubated at 37° C. overnight. The drugs were dissolved in serum-free medium and 100 µL of 2× drug solution was added to the cells. After the drug-treated cells were incubated for 22 hr at 37° C., 100 µL of conditioned media were removed from the wells and 100 µL of medium containing rotenone (2×) was added to the cells. After 2 hr incubation at 37° C., the medium from the plates were aspirated using an automatic plate washer (Biotek) and complex I-driven ATP synthesis was measured following the protocol of Yoshida and Fujikawa (Fujikawa et al., Biochemical and Biophysical Research Communications, 2010, 401, 538-543). The plate washing steps were minimized to prevent cell loss and assay variability.

For the lymphoblasts, drug-treated cells were centrifuged and resuspended at a concentration of $2 \times 10^6$ cells/mL, in the permeabilization buffer containing activated streptolysin O (Sigma). After 10 min incubation at 4° C., the cells were centrifuged and resuspended in transfer buffer at the same concentration. The cells were then incubated at 37° C. for 10 min followed by centrifugation and resuspension in buffer A containing malate (5 mM, Sigma), sodium pyruvate (5 mM, Sigma) and high purity ADP (200 µM, Apollo Scientific). Subsequently, 50 µL of buffer A containing 100,000 cells were plated in each wells of a 96-well plate. After 20 min of incubation at the room temperature the complex I-driven ATP synthesis was measured by using ATP Bioluminescence Assay Kit CLS II (Roche) following manufacturer's instruction.

Example 3: Testing Papaverine, Zolpidem, and Rapamycin in Ndufs4 Knockout Mice, a Mouse Model of Leber's Hereditary Optic Neuropathy (LHON) and Similar Mitochondrial Diseases This example illustrates the use of papaverine, zolpidem, and rapamycin to prevent, alleviate, attenuate the progression of, or treat a mitochondrial disease with clinical features that include vision loss or blindness. The drugs were evaluated using a mouse model of Leber's hereditary optic neuropathy (LHON), Ndufs4 knockout mice.

Methods

Drug Formulation.

Wild type and Ndufs4 knockout mice were placed in one of five groups: vehicle, papaverine (20 mg/kg), zolpidem (20 mg/kg), rapamycin (8 mg/kg), or idebenone (200 mg/kg). For papaverine, zolpidem, and rapamycin, drug was dissolved in DMSO which was diluted in 5% PEG-400/5% Tween-20 in PBS. Vehicle contained all components except for the drug. The solution was then sterile filtered and intraperitoneal injections were performed using a 30 gauge needle. Idebenone was administered as a jelly and consumed orally.

Visual Cliff Test.

Mice performed a visual cliff test prior (P21) to two weeks of drug/vehicle treatment and post-treatment (P35). The visual cliff apparatus is made of clear acrylic and elevated 1 meter of the ground. One third of the clear box has a checkerboard pattern and the border between the checkboard pattern and the clear acrylic is what stimulates the 'cliff' Once the mouse reached and detected the edge we counted the number of edge detections within a maximum one minute period (shorter time if mouse crossed edge without returning). We counted the number of edge detections which was then divided by seconds as a measure of the presence or absence of visual function.

Results

Visual Cliff.

Figure 20:
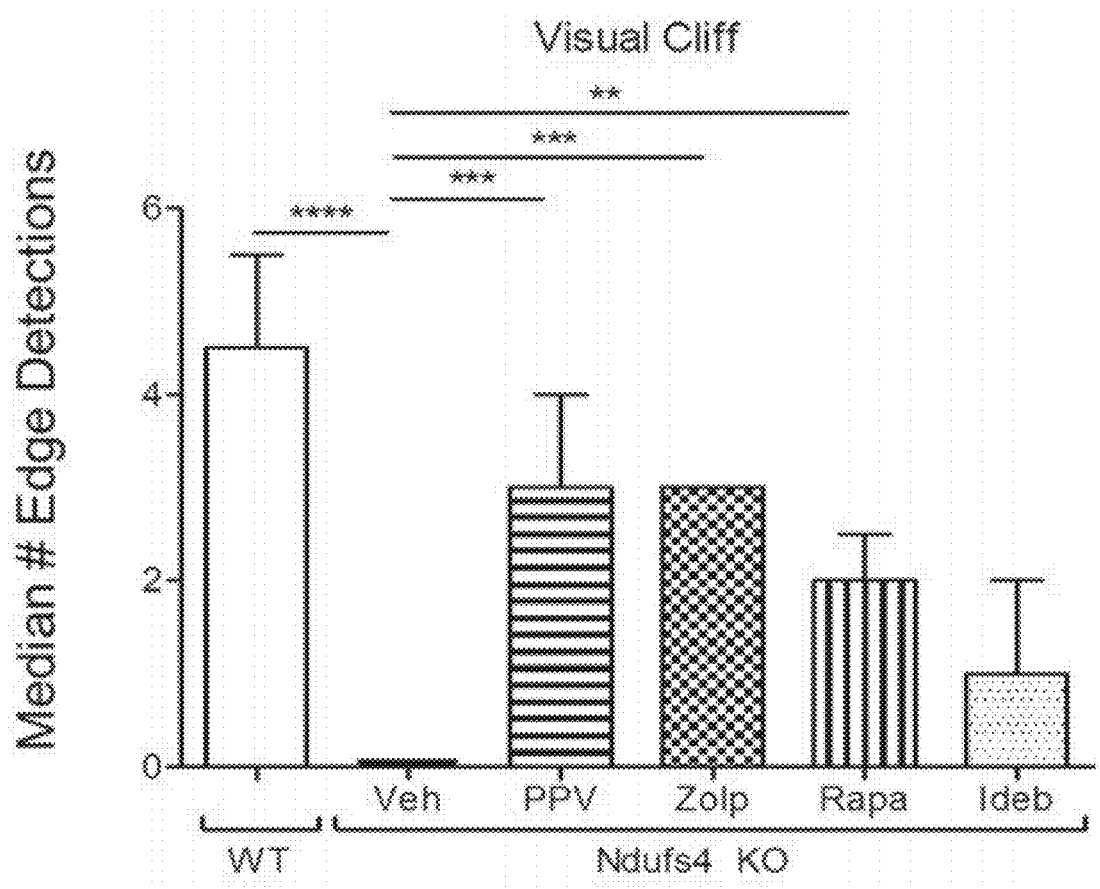
FIG. 20 provides post-treatment (P35) visual cliff data of wild type (WT) and Ndufs4 knockout (KO) mice with vehicle (Veh), papaverine (PPV), zolpidem (Zolp), rapamycin (Rapa), and idebenone (Ideb) treatment. After two weeks (P21-P35) of intraperitoneal drug treatment, papaverine, zolpidem, and rapamycin were able to significantly protect the Ndufs4 KO mice from developing vision loss. A graphical representation of the median number of edge detections performed by wild type and vehicle or drug treated Nudfs4 KO mice is shown. Error bars represent median absolute deviation. Statistical significance was determined by two-tailed student's t test. * P<0.05,  P<0.01 * P<0.001, **** P<0.0001.

Visual cliff testing at postnatal day 21 prior to receiving any treatment reveals that both wild type and Ndufs4 KO mice had visual function intact. After two weeks of treatment, the Ndufs4 KO group receiving vehicle injections lost their visual capacity based on median # edge detection, which is consistent with previous results from non-treated P35 Ndufs4 KO mice. However, Ndufs4 KO mice that received papaverine, zolpidem, or rapamycin had median # edge detections that indicated that their visual function was preserved, whereas the variability in visual response with idebenone treatment was not significant (FIG. 20). The lower median # edge detection as seen in FIG. 20 in the drug treatment groups is not indicative that their visual function decreased. Rather, this is a test that validated the presence or absence of visual function. The lower median value can be explained by less ambulatory movement from the Ndufs4 KO in general.

Gene Expression.

We have previously shown that inflammatory gene expression of Aif1, Tlr2, B2m, Cc15, and Cxc110 are all elevated in the Ndufs4 KO mouse compared to wild type by more than 3-fold, indicating an inflammatory pathomechanism of mitochondrial blindness (Yu et al., Proc Natl Acad Sci USA, 2015, 112(42): E5689-98). These results indicated that there was an innate immune and inflammatory response that is spontaneously occurring in the retina of these mice around postnatal day 32. Papaverine, zolpidem, rapamycin, and idebenone were administered to Ndufs4 KO mice to determine whether their protection of vision (FIG. 20) was through an anti-inflammatory mechanism of action. Ndufs4 KO mice treated with all four drugs significantly inhibited a portion of the innate immune/inflammatory response (FIGS. 21A-21E). Thus, papaverine, zolpidem, and rapamycin appear to protect mitochondrial loss of vision through an antiinflammatory mechanism.

Protection of Startburst Amacrine Cell Loss.

Ndufs4 KO mice present with a significant loss of starburst amacrine cells starting at postnatal 24 days. After two weeks (P21-P35) of intraperitoneal injections of rapamycin and zolpidem, there was a significant protection of startburst amacrine cells from apoptosis. Additionally, papaverine treatment showed less cell loss than vehicle-treated Ndufs4 KO mice. See, FIGS. 22A-22F.

Inhibition of Microglia Activation.

Ndufs4 KO mice have an elevated innate immune and inflammatory response at P30. After two weeks (P21-P35)

of intraperitoneal treatment with papaverine, there was a significant inhibition of microglia activation. Additionally, zolpidem treatment showed a decrease in microglia activation. See, FIGS. 23A-23F.

We have shown that papaverine, zolpidem, and rapamycin are effective in preserving visual function in the Ndufs4 KO mouse with mitochondrial blindness, and that these drugs are effective in inhibition of the innate immune and inflammatory response that occurs immediately prior to or during the period of vision loss in these mice. These data support the use of papaverine, zolpidem, and rapamycin as therapeutic agents in mitochondrial blindness, such as Leber's hereditary optic neuropathy (LHON), and in mitochondrial disease in general.

The data presented in the examples described herein indicate that drugs such as papaverine, zolpidem, rapamycin, methoxamine, methenamine, methotrexate, azathioprine, zidovudine, and fluorouracil or their analogs are useful for preventing, alleviating, attenuating the progression of, or treating mitochondrial disease in general, and LHON in particular. There is currently no FDA-approved therapy for any mitochondrial disease.

V. Exemplary Embodiments

Exemplary embodiments provided in accordance with the presently disclosed subject matter include, but are not limited to, the claims and the following embodiments:

1. A method for preventing, alleviating, attenuating the progression of, or treating a mitochondrial disease in a subject in need thereof, comprising administering to the subject a therapeutically effective amount of a drug selected from the group consisting of papaverine, zolpidem, a nucleotide metabolism inhibitor, methoxamine, methenamine, pharmaceutically acceptable salts thereof, analogs thereof, and combinations thereof.
2. The method of embodiment 1, wherein the nucleotide metabolism inhibitor is selected from the group consisting of methotrexate, azathioprine, fluorouracil, zidovudine, pharmaceutically acceptable salts thereof, analogs thereof, and combinations thereof.
3. The method of embodiment 1 or 2, wherein the drug is administered orally, ocularly, topically, systemically, intravenously, subcutaneously, intraperitoneally, intramuscularly, transdermally, or transmucosally.
4. The method of any one of embodiments 1 to 3, wherein the therapeutically effective amount of the drug is an amount sufficient to stimulate mitochondrial ATP synthesis and/or to inhibit the induction of one or more inflammatory genes.
5. The method of any one of embodiments 1 to 4, further comprising administering a therapeutically effective amount of rapamycin, a pharmaceutically acceptable salt thereof, or an analog thereof.
6. The method of embodiment 5, wherein rapamycin is administered orally, ocularly, topically, systemically, intravenously, subcutaneously, intraperitoneally, intramuscularly, transdermally, or transmucosally.
7. The method of embodiment 5 or 6, wherein the therapeutically effective amount of rapamycin is an amount sufficient to inhibit the induction of one or more inflammatory genes.
8. The method of any one of embodiments 1 to 7, further comprising administering a therapeutically effective amount of idebenone, a pharmaceutically acceptable salt thereof, or an analog thereof.
9. The method of embodiment 8, wherein the therapeutically effective amount of idebenone is an amount sufficient to stimulate mitochondrial ATP synthesis and/or to inhibit the induction of one or more inflammatory genes.
10. The method of any one of embodiments 1 to 9, wherein the mitochondrial disease leads to vision loss or blindness.
11. The method of any one of embodiments 1 to 10, wherein the mitochondrial disease is selected from the group consisting of Leigh syndrome; Leber's hereditary optic neuropathy (LHON); Alpers-Huttenlocher syndrome; ataxia neuropathy syndromes (ANS); chronic progressive external opthalmoplegia (CPEO); diabetes mellitus and deafness (DAD); dominant optic atrophy (DOA); Friedreich's ataxia (FRDA); infantile myopathy and lactic acidosis; Kearns-Sayre Syndrome (KSS); myoclonic epilepsy with ragged red fibers (MERRF); mitochondrial myopathy, encephalomyopathy, lactic acidosis, stroke (MELAS); myoclonic epilespy myopathy sensory ataxia (MEMSA); mitochondrial neurogastrointestinal encephalopathy (MNGIE); neuropathy, ataxia, retinitis pigmentosa, and ptosis (NARP); Pearson syndrome; and Sengers syndrome.
12. The method of any one of embodiments 1 to 11, wherein the mitochondrial disease is Leigh syndrome or Leber's hereditary optic neuropathy (LHON).
13. The method of any one of embodiments 1 to 12, wherein the subject has a likelihood of having or developing the mitochondrial disease.
14. The method of any one of embodiments 1 to 13, wherein the subject has at least one genetic mutation associated with the mitochondrial disease.
15. The method of any one of embodiments 1 to 13, wherein the subject is clinically asymptomatic.
16. The method of any one of embodiments 1 to 13, wherein the subject has at least one clinical symptom of the mitochondrial disease.
17. The method of embodiment 16, wherein the at least one clinical symptom comprises vision loss or blindness.
18. A method for preventing, alleviating, attenuating the progression of, or treating a mitochondrial disease in a subject in need thereof, comprising administering to the subject a therapeutically effective amount of rapamycin, a pharmaceutically acceptable salt thereof, or an analog thereof,
wherein the mitochondrial disease is selected from the group consisting of Leber's hereditary optic neuropathy (LHON); Alpers-Huttenlocher syndrome; ataxia neuropathy syndromes (ANS); chronic progressive external opthalmoplegia (CPEO); diabetes mellitus and deafness (DAD); dominant optic atrophy (DOA); Friedreich's ataxia (FRDA); infantile myopathy and lactic acidosis; Kearns-Sayre Syndrome (KSS); myoclonic epilepsy with ragged red fibers (MERRF); mitochondrial myopathy, encephalomyopathy, lactic acidosis, stroke (MELAS); myoclonic epilespy myopathy sensory ataxia (MEMSA); mitochondrial neurogastrointestinal encephalopathy (MNGIE); neuropathy, ataxia, retinitis pigmentosa, and ptosis (NARP); Pearson syndrome; and Sengers syndrome.
19. The method of embodiment 18, wherein the mitochondrial disease is Leber's hereditary optic neuropathy (LHON).
20. The method of embodiment 18 or 19, wherein rapamycin is administered orally, ocularly, topically, systemically, intravenously, subcutaneously, intraperitoneally, intramuscularly, transdermally, or transmucosally.
21. The method of any one of embodiments 18 to 20, wherein the therapeutically effective amount of rapamycin is an amount sufficient to inhibit the induction of one or more inflammatory genes.
22. The method of any one of embodiments 18 to 21, further comprising administering a therapeutically effective amount of a drug selected from the group consisting of papaverine, zolpidem, a nucleotide metabolism inhibitor, methoxamine, methenamine, idebenone, pharmaceutically acceptable salts thereof, analogs thereof, and combinations thereof.
23. The method of embodiment 22, wherein the nucleotide metabolism inhibitor is selected from the group consisting of methotrexate, azathioprine, fluorouracil, zidovudine, pharmaceutically acceptable salts thereof, and analogs thereof.
24. The method of embodiment 22 or 23, wherein the drug is administered orally, ocularly, topically, systemically, intravenously, subcutaneously, intraperitoneally, intramuscularly, transdermally, or transmucosally.
25. The method of any one of embodiments 22 to 24, wherein the therapeutically effective amount of the drug is an amount sufficient to stimulate mitochondrial ATP synthesis and/or to inhibit the induction of one or more inflammatory genes.
26. The method of any one of embodiments 18 to 25, wherein the subject has a likelihood of having or developing the mitochondrial disease.
27. The method of any one of embodiments 18 to 26, wherein the subject has at least one genetic mutation associated with the mitochondrial disease.
28. The method of any one of embodiments 18 to 27, wherein the subject is clinically asymptomatic.
29. The method of any one of embodiments 18 to 27, wherein the subject has at least one clinical symptom of the mitochondrial disease.
30. The method of embodiment 29, wherein the at least one clinical symptom comprises vision loss or blindness.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

| Informal Sequence Listing | |
|---|---|
| Forward primer for Actb<br>ATGTGGATCAGCAAGCAGGA | SEQ ID NO: 1 |
| Forward primer for Aif1<br>ATCAACAAGCAATTCCTCGATGA | SEQ ID NO: 2 |
| Forward primer for B2m<br>CACTGAATTCACCCCCACTGA | SEQ ID NO: 3 |
| Forward primer for C1qa<br>ACAATGGCATGGTGGGCATA | SEQ ID NO: 4 |
| Forward primer for C1ra<br>GGAGAGCTGAGGACCCAAAA | SEQ ID NO: 5 |
| Forward primer for Ccl2<br>GGCTGGAGAGCTACAAGAGG | SEQ ID NO: 6 |
| Forward primer for Ccl5<br>TTTGCCTACCTCTCCCTCG | SEQ ID NO: 7 |
| Forward primer for Ccl12<br>ATTTCCACACTTCTATGCCTCCT | SEQ ID NO: 8 |
| Forward primer for Cd68<br>TGTCTGATCTTGCTAGGACCG | SEQ ID NO: 9 |
| Forward primer for Cd86<br>CACAAGAAGCCGAATCAGCC | SEQ ID NO: 10 |
| Forward primer for Cxcl9<br>CCAAGCCCCAATTGCAACAA | SEQ ID NO: 11 |
| Forward primer for Cxcl10<br>CCAAGTGCTGCCGTCATTTTC | SEQ ID NO: 12 |
| Forward primer for Cx3cr1<br>GTCTTCACGTTCGGTCTGGT | SEQ ID NO: 13 |
| Forward primer for Fas<br>AGCCCGTTGGAGTGATTCAA | SEQ ID NO: 14 |
| Forward primer for Gapdh<br>TGCACCACCAACTGCTTAG | SEQ ID NO: 15 |
| Forward primer for Gfap<br>AGAAGGGGAAGGCCAAAAAGT | SEQ ID NO: 16 |
| Forward primer for Icam1<br>TTCTCATGCCGCACAGAACT | SEQ ID NO: 17 |
| Forward primer for Mapk1<br>CGCCTACTCAAGCACCTGAA | SEQ ID NO: 18 |
| Forward primer for Mmp9<br>CTCTAAGCCTGACCCAAGGC | SEQ ID NO: 19 |
| Forward primer for Mmp12<br>TGGTACACTAGCCCATGCTTT | SEQ ID NO: 20 |
| Forward primer for Ndufs4<br>GAGCACATCCACTTGGAAGC | SEQ ID NO: 21 |
| Forward primer for Nes<br>AGAGGACCCAAGGCATTTCG | SEQ ID NO: 22 |
| Forward primer for Opa1<br>CCCAGCTCAGAAGACCTTGC | SEQ ID NO: 23 |

| Informal Sequence Listing | |
|---|---|
| Forward primer for Tlr2<br>CAGTGGCCAGAAAAGATGCG | SEQ ID NO: 24 |
| Forward primer for Tlr3<br>GAGCCACAGTGATAGATGGCA | SEQ ID NO: 25 |
| Forward primer for Tlr4<br>CTCTGGGGAGGCACATCTTC | SEQ ID NO: 26 |
| Reverse primer for Actb<br>GGGTGTAAAACGCAGCTCAG | SEQ ID NO: 27 |
| Reverse primer for Aif1<br>CAGCATTCGCTTCAAGGACATA | SEQ ID NO: 28 |
| Reverse primer for B2m<br>TCTCGATCCCAGTAGACGGT | SEQ ID NO: 29 |
| Reverse primer for C1qa<br>GCCGTTCTAGTCGGGAAACA | SEQ ID NO: 30 |
| Reverse primer for C1ra<br>CCACCCCATAGAACAGGGTC | SEQ ID NO: 31 |
| Reverse primer for Ccl2<br>GGTCAGCACAGACCTCTCTC | SEQ ID NO: 32 |
| Reverse primer for Ccl5<br>CGACTGCAAGATTGGAGCACT | SEQ ID NO: 33 |
| Reverse primer for Ccl12<br>ATCCAGTATGGTCCTGAAGATCA | SEQ ID NO: 34 |
| Reverse primer for Cd68<br>GAGAGTAACGGCCTTTTTGTGA | SEQ ID NO: 35 |
| Reverse primer for Cd86<br>TGTCAGCGTTACTATCCCGC | SEQ ID NO: 36 |
| Reverse primer for Cxcl9<br>AGTCCGGATCTAGGCAGGTT | SEQ ID NO: 37 |
| Reverse primer for Cxcl10<br>GGCTCGCAGGGATGATTTCAA | SEQ ID NO: 38 |
| Reverse primer for Cx3cr1<br>GTCAGTGATGCTCTTGGGCT | SEQ ID NO: 39 |
| Reverse primer for Fas<br>CCCCCTGCAATTTCCGTTTG | SEQ ID NO: 40 |
| Reverse primer for Gapdh<br>GATGCAGGGATGATGTTC | SEQ ID NO: 41 |
| Reverse primer for Gfap<br>GGCAGGGCTCCATTTTCAATC | SEQ ID NO: 42 |
| Reverse primer for Icam1<br>TCCTGGCCTCGGAGACATTA | SEQ ID NO: 43 |
| Reverse primer for Mapk1<br>CACGAGGTACACTTCGCTGA | SEQ ID NO: 44 |
| Reverse primer for Mmp9<br>CCGTGGGAGGTATAGTGGGA | SEQ ID NO: 45 |
| Reverse primer for MMp12<br>AGTCCACGTTTCTGCCTCATC | SEQ ID NO: 46 |
| Reverse primer for Ndufs4<br>GATGTGCTCTTCTGGAACACC | SEQ ID NO: 47 |
| Reverse primer for Nes<br>TGCCTTCACACTTTCCTCCC | SEQ ID NO: 48 |
| Reverse primer for Opa1<br>CCAATTTGGGACCTGCAGTGA | SEQ ID NO: 49 |
| Reverse primer for Tlr2<br>CCTCCAGCGTCTGAGGAATG | SEQ ID NO: 50 |
| Reverse primer for Tlr3<br>TCCAGCAGAAGAGACACAACA | SEQ ID NO: 51 |
| Reverse primer for Tlr4<br>TGCTCAGGATTCGAGGCTTT | SEQ ID NO: 52 |

What is claimed is:

1. A method for attenuating the progression of a mitochondrial disease that leads to vision loss or blindness in a subject in need thereof, comprising administering to the subject a therapeutically effective amount of a drug selected from the group consisting of zolpidem, a pharmaceutically acceptable salt thereof, and an analog thereof, wherein inhibition of Aif1, Tlr2, B2m, Cc15, or Cxc110 inflammatory gene expression is detected after administration of the drug.

2. The method of claim 1, wherein the drug is administered orally, ocularly, topically, systemically, intravenously, subcutaneously, intraperitoneally, intramuscularly, transdermally, or transmucosally.

3. The method of claim 1, wherein the therapeutically effective amount of the drug is an amount sufficient to stimulate mitochondrial ATP synthesis and/or to inhibit the induction of one or more inflammatory genes.

4. The method of claim 1, further comprising administering a therapeutically effective amount of rapamycin, a pharmaceutically acceptable salt thereof, or an analog thereof.

5. The method of claim 4, wherein rapamycin is administered orally, ocularly, topically, systemically, intravenously, subcutaneously, intraperitoneally, intramuscularly, transdermally, or transmucosally.

6. The method of claim 4, wherein the therapeutically effective amount of rapamycin is an amount sufficient to inhibit the induction of one or more inflammatory genes.

7. The method of claim 1, further comprising administering a therapeutically effective amount of idebenone, a pharmaceutically acceptable salt thereof, or an analog thereof.

8. The method of claim 7, wherein the therapeutically effective amount of idebenone is an amount sufficient to stimulate mitochondrial ATP synthesis and/or to inhibit the induction of one or more inflammatory genes.

9. The method of claim 1, wherein the mitochondrial disease is Leber's hereditary optic neuropathy (LHON).

10. The method of claim 1, wherein the subject has a family history of the mitochondrial disease.

11. The method of claim 1, wherein the subject has at least one genetic mutation associated with the mitochondrial disease.

12. The method of claim 1, wherein the subject is clinically asymptomatic.

13. The method of claim 1, wherein the subject has at least one clinical symptom of the mitochondrial disease.

14. The method of claim 13, wherein the at least one clinical symptom comprises vision loss or blindness.

15. The method of claim 1, wherein the drug is administered by intravitreal injection.

* * * * *